United States Patent
Cone et al.

(10) Patent No.: US 6,485,970 B1
(45) Date of Patent: Nov. 26, 2002

(54) IMMUNOINTERACTIVE ANTIBODY

(76) Inventors: Robert E. Cone, 16 Green Woods La., Unionville, CT (US) 06085; George M. Georgiou, 55 Hudson Street, Fawkner, Victoria (AU), 3060; Colin H. Little, 602-604 Waverly Road, Glen Waverley, Victoria (AU), 3150

(*) Notice: Subject to any disclaimer, the term of this patent is extended or adjusted under 35 U.S.C. 154(b) by 0 days.

(21) Appl. No.: 09/508,701
(22) PCT Filed: Sep. 16, 1998
(86) PCT No.: PCT/AU98/00765
  § 371 (c)(1),
  (2), (4) Date: May 10, 2000
(87) PCT Pub. No.: WO99/14243
  PCT Pub. Date: Mar. 25, 1999

Related U.S. Application Data
(60) Provisional application No. 60/059,047, filed on Sep. 16, 1997.

(30) Foreign Application Priority Data
Sep. 11, 1998 (AU) .............................................. PP5850

(51) Int. Cl.⁷ ........................... C12N 5/12; C07K 16/18; A61K 39/395
(52) U.S. Cl. ................. 435/335; 530/387.1; 530/387.5; 530/388.1; 530/388.2; 530/388.7; 530/388.73; 530/388.75; 530/388.85; 530/388.25; 530/388.23; 424/130.1; 424/137.1; 424/141.1; 424/152.1; 424/153.1; 424/154.1; 424/156.1; 424/158.1; 424/172.1; 424/173.1; 424/178.1; 435/325; 435/326; 435/329; 435/332; 435/337; 435/343; 435/343.1; 435/343.2; 435/344.1; 435/346
(58) Field of Search ........................... 530/387.1, 387.3, 530/387.5, 388.1, 388.2, 388.25, 388.7, 388.23, 388.73, 388.75, 388.85, 389.1, 389.3, 389.6; 424/130.1, 137.1, 133.1, 141.1, 152.1, 153.1, 154.1, 156.1, 158.1, 172.1, 173.1, 178.1; 435/325, 326, 329, 332, 335, 337, 343, 343.1, 343.2, 344.1, 346

(56) References Cited

U.S. PATENT DOCUMENTS 5,368,854 A * 11/1994 Rennick

OTHER PUBLICATIONS

Ferguson et al. 1986 J. Immunol. 136:2896–2903.*
Radic and Seal Methods: A Companion to Methods in Enzymology 11:20–26 1997.*
Zola "Monoclonal Antibodies: A Manual of Techniques", CRC Press, Boca Raton, Florida 1987, pp. 1–11.*
Beaman, Kenneth D., et al. (1984) Messenger RNA for an antigen–specific binding molecule from an antigen–specific T–cell hybrid. *Proc. Natl. Acad. Sci. USA* vol. 81:1524–1528.
Beaman, Kenneth D., et al. (1984) Production and Purification of Monoclonal T Lymphocyte Antigen Binding Molecules (TABM). *Biochemical and Biophysical Research Communications* vol. 125, No. 2:475–483.
Cone, Robert E., et al. (1988) T Cell–Derived Antigen Binding Molecules (TABM): Molecular and Functional Properties. *Intern. Rev. Immunol.* 3:205–228.
Cone, Robert E., et al. (1985) Antigen–Binding Molecules of T–Cells: Charge Heterogeneity and Structural Lability. *Molecular Immunology* vol. 22, No. 4:399–406.
Cone, Robert E., et al. (1986) Phenotypic Similarity Between T–Cell Antigen Binding Molecules. *Expl. Clin. Immunogenet* 3:208–218.
Cone, Robert E., et al. (1987) Quantitation of T Cell Antigen–Binding Molecules (TABM) in the Sera of Non-immunized, Immunized, and Desensitized Mice. *The Journal of Immunology* vol. 138:234–239.
Cone, Robert E., et al. (1991) T Cell Non–MHC–Restricted Antigen–Binding Molecules Secreted or Associated with the Cell Membrane Are Antigenically Distinct. *Cellular Immunology* 137:529–538.
Cone, Robert E., et al. (1993) Partial Amino Acid Sequence of Monoclonal Extracellular Antigen–Specific T Cell Proteins. *Immunological Investigations* 22(8):541–552.
Cone, Robert E., et al. (1998) Extracellular (Soluble) Antigen–Specific T Cell Proteins Related to the T Cell Receptor for Antigen (sTCRr): Serologic and Primary Amino Acid Sequence Similarity to T Cell Receptor Alpha Chains and Association with Cytokines. *Journal of Interferon and Cytokine Research* 18:55–67.
DiBrino, Marianne, et al. (1991) T Cell Derived Proteins from Normal Human Sera and Their Relationship to T Cell Antigen Binding Molecules. *Clinical Immunology and Immunopathology* 59:271–287.
Garssen, Johan, et al. (1994) T Cell–derived Antigen Binding Molecules Play a Role in the Induction of Airway Hyperresponsiveness. *Am J Respir Crit Care Med.* 150:1528–1538.
Hadjikouti, Christina A., et al. (1995) Intracameral Injection of Antigen Potentiates the Production of Antigen–Specific T Cell Proteins in Serum After the Induction of Delayed–type Hypersensitivity. *Investigative Ophthalmology & Visual Science* vol. 36 No. 7:1470–1476.
Parmentier, H. K., et al. (1989) Antigen–Specific T–Cell Factors Induce Isotype–Like Suppression of Mast Cell and Eosinophil–Rich T–Cell–Dependent Inflammation in the Intestine of Mice Infected with *Trichinella spiralis*. *Int Arch Allergy Appl Immunol* 90:144–154.

(List continued on next page.)

Primary Examiner—Phillip Gambel
Assistant Examiner—Jessica H. Roark
(74) *Attorney, Agent, or Firm*—Greenlee Winner and Sullivan, PC

(57) ABSTRACT

The present invention relates generally to immunointeractive molecules and their use *inter alia* in the detection and/or purification of T-cell antigen binding molecules (TABMs). The ability to determine the presence and levels of particular TABMs provides a useful diagnostic procedures for a variety of disease conditions.

5 Claims, 60 Drawing Sheets

OTHER PUBLICATIONS

Rellahan, Barbara L., et al. (1989) Expression of Non–MHC–Restricted T Cell Antigen–Binding Molecules by Thymic Lymphocytes. *Cellular Immunology* 123:166–176.

Rellahan, Barbara L., et al. (1990) Ontogeny and Expression of Non–MHC–Restricted T Cell Antigen–Binding Molecules by Thymocytes and Peripheral T Cell Subsets. *Cellular Immunology* 130:176–185.

Urbanski, Marianne, et al. (1992) Appearance of T Lymphocyte–Derived Proteins Specific for the Immunizing Antigen in Serum During a Humoral Immune Response. *The Journal of Immunology* 148:2840–2844.

Urbanski, Marianne, et al. (1994) T Cell–Derived Antigen–Specific Humoral Immune Response. *Cellular Immunology* 153:131–141.

Wang, Y., et al. (1995) High–Dose Cyclophosphamide Inhibits Anterior Chamber–Associated Immune Deviation (ACAID) and the Production of Extracellular Antigen–Specific T Cell Proteins Induced by Trinitrophenylated (TN) Spleen Cells. *Cellular Immunology* 165:284–288.

Wang, Y., et al. (1997) Serum TABM Produced During Anterior Chamber–Associated Immune Deviation Passively Transfers Suppression of Delayed–type Hypersensitivity to Primed Mice. *International Immunology* vol. 9 No. 2:211–218.

* cited by examiner

28k →

Dilution of serum bound to plate 1/X hTABM: 500 250 125 62 31 0 ng/ml

23k →

I   II

25K→

IMMUNOINTERACTIVE ANTIBODY

CROSS-REFERENCE TO RELATED APPLICATIONS

This application is a national phase application of Patent Cooperation International Application PCT/AU98/00765, filed Sep. 16, 1998, which application claims priority from Australian Patent Application No. PP5850/98, filed Sep. 11, 1998, and from United States Provisional Application No. 60/059,047, filed Sep. 16, 1997.

FIELD OF THE INVENTION

The present invention relates generally to immunointeractive molecules and their use *inter alia* in the detection and/or purification of T-cell antigen binding molecules (TABMs). These molecules are also called T-cell derived antigen binding molecules. The ability to determine the presence and levels of particular TABM provide a useful diagnostic monitoring procedure for a variety of disease or other physiological conditions which are associated directly or indirectly with TABM including a range of allergies, immunological status, immunological dysfunction, neuropeptide release, infection, cancer, autoimmune disease or vaccination status. The immunointeractive molecules of the present invention are also useful in a range of conditions including modulating aspects of an immune response such as but not limited to cell mediated immunity.

BACKGROUND OF THE INVENTION

Bibliographic details of the publications numerically referred to in this specification are collected at the end of the description.

The rapidly increasing knowledge of the immune system is greatly facilitating the rationale design of therapeutic and diagnostic procedures based on modulating aspects and compounds of the immune system. Our understanding of the immune system is predicated in part on the identification and characterization of immune system components and determining how various components interact. Although a substantial focus of the research over the years has been on studying immunoglobulins, other immunointeractive molecules such as TABM have received less attention. This has been due, in part, to the inability to purify large amounts of these immunointeractive molecules.

TABM are antigen binding molecules generally located in the serum, derived from T-cells TABM can be regarded as immunoproteins which are antigen specific and, hence, are analogous to immunoglobulins.

TABM are, however, distinct from immunoglobulins. For example, TABM recognise different epitopes to immunoglobulins. TABM are present in serum in multimetric form, the monomer having an apparent molecular weight on a 10–15% w/v SDS polyacrylamide gel of about 24,000–30,000 daltons. In polymeric form, the molecular weight may be greater than 1,000,000 daltons. The high molecular weight of TABM and their non-polar, hydrophobic nature have made the study of these molecules very difficult.

TABM are present in the serum at a concentration of between 10–50 $\mu$g/ml. The monomeric units share some homology with the C$\alpha$ chain of the T-cell receptor (TCR). However, TABM are not soluble forms of TCR and exhibit physiological and biochemical properties distinct from TCR.

There appears to be several types of TABM with different functions. One particularly important function is their involvement in immuno-regulation. For example, some TABM initiate delayed type hypersensitivity while other types appear to inhibit cell-mediated immunity. The latter type of TABM are associated with cytokines and in particular interleukin 10 (IL-10) and transforming growth factor beta (TGF-$\beta$). It is thought that these TABM "focus" the cytokines to where the antigen is localised to suppress the cell-mediated immune response to the antigen.

It is likely, therefore, that TABM are involved in a number of clinical disorders or others physiological conditions involving suppression or activation of immune processes. However, as TABM are present in serum in only minute amounts, it has hithertofore been impractical to measure TABM levels or to use TABM in diagnostic protocols.

In work leading up to the present invention, the inventors sought monoclonal antibodies to TABM. The isolation of such monoclonal antibodies enables the purification of large quantities of TABM and the development of diagnostic assays based on identification of specific TABM or amounts of specific TABM as well as the development of therapeutic protocols based on modulating TABM levels.

SUMMARY OF THE INVENTION

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

One aspect of the present invention provides an immunointeractive molecule comprising a portion which is capable of specifally interacting with TABM.

Another aspect of the present invention is directed to a hybridoma cell line producing a monoclonal antibody comprising a binding portion specific to TABM.

Yet another aspect of the present invention contemplates a hybridoma cell line having the characteristics of cell line MG3C9-1A12 producing a monoclonal antibody capable of interacting with TABM.

Cell line MG3C9-1A12 was deposited under the provisions of the Budapest Treaty with the American Type Culture Collection, 10801 University Boulevard, Manassas, Va. 20110-2209 on Oct. 21, 1998. Accession No. HB-12589 was assigned to this deposited cell line.

Still yet another aspect of the present invention contemplates a method of detecting TABM in a biological sample from a subject said method comprising contacting said biological sample with an immunointeractive molecule specific for TABM or their derivatives or homologues for a time and under conditions sufficient for an immunointeractive molecules-TABM complex to form and then detecting said complex.

Another aspect of the present invention provides a composition comprising an immunointeractive molecules specific for TABM.

Yet another aspect of the present invention contemplates a method for determining assessing or otherwise monitoring the immunological status of an individual said method comprising screening for the pressure or level of TABM in a biological sample from said individual.

—■— OD ANTI-TABM
—■— OD ANTI-KAPPA
—○— OD ANTI LAMBDA
—▲— OD ANTI ALBUMIN

B) monoclonal anti-human TcR α chain. β chain and (controls): anti-murine LyT-2, anti-H-2K.

—□— ANTI-ALPHA
—▲— ANTI-BETA
—○— ANTI LYT-2
—△— ANTI-H2K

C) affinity purified anti-TGF-β1, TGF-β2, TGF-β3. Bound antibody was developed with alkaline phosphatase-conjugated to anti-immune or rabbit IgG.

Figure 1A:
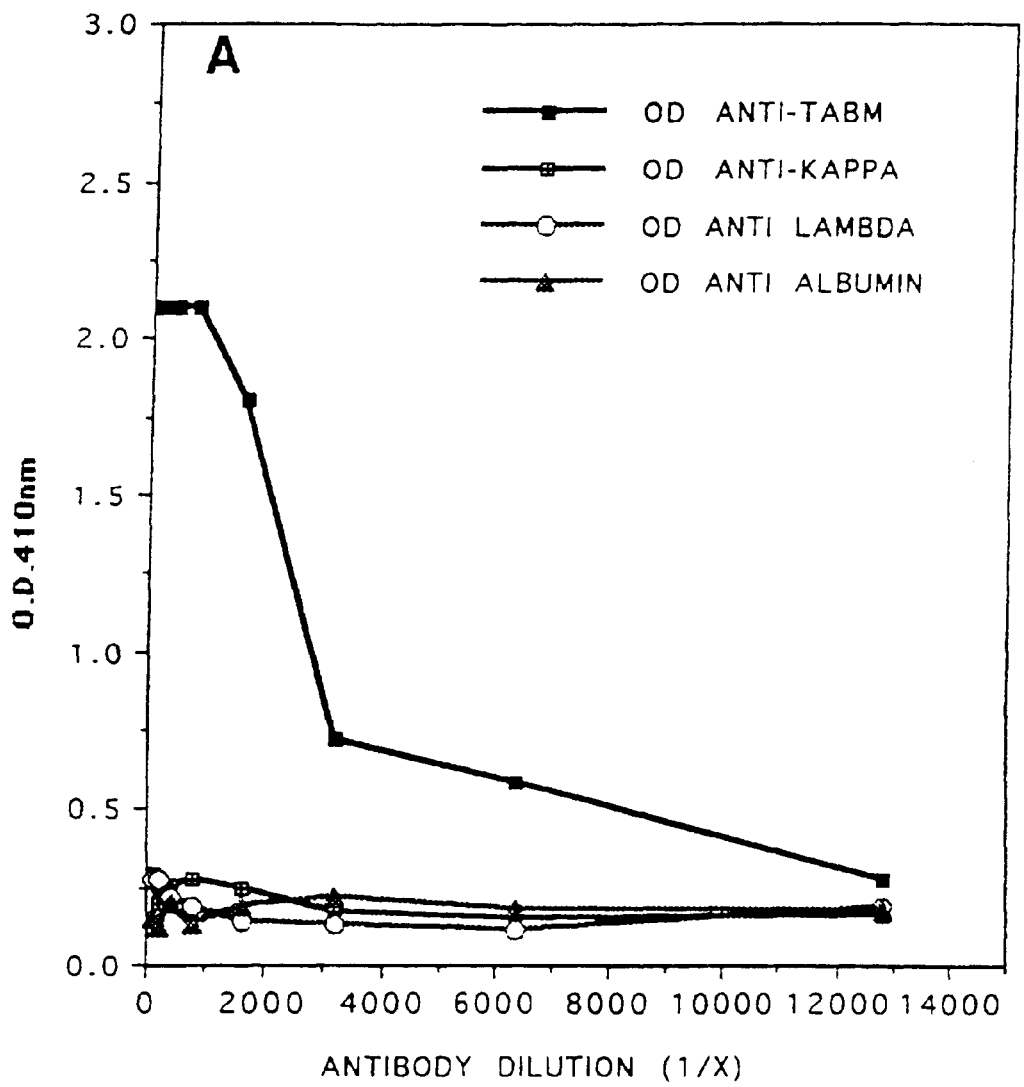
FIGS. 1A–1C are a graphical representation of an ELISA of Cohn Fraction III TABM. One hundred ng of Cohn Fraction III TABM were coated to microtiter trays and assayed with dilutions of A) rabbit anti-human TABM R28, anti-immunoglobuin κ chain, λ chain or albumin.
Figure 1B:
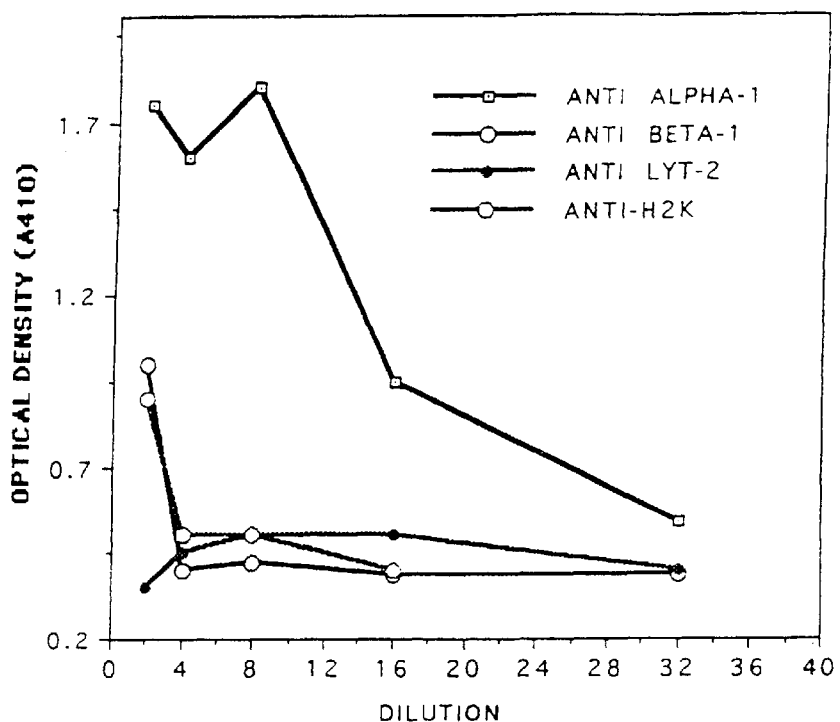
Figure 1C:
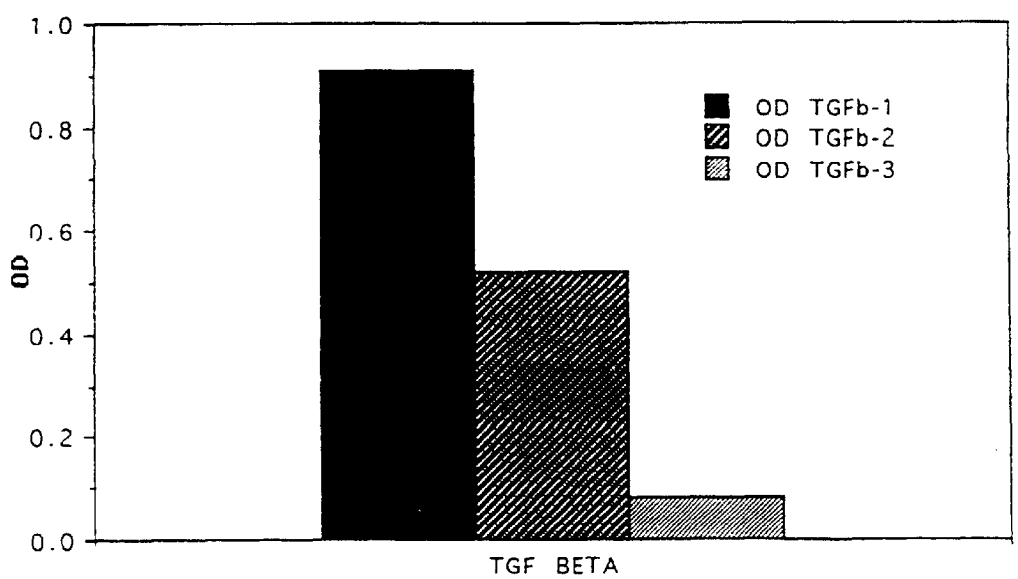
Figure 2:
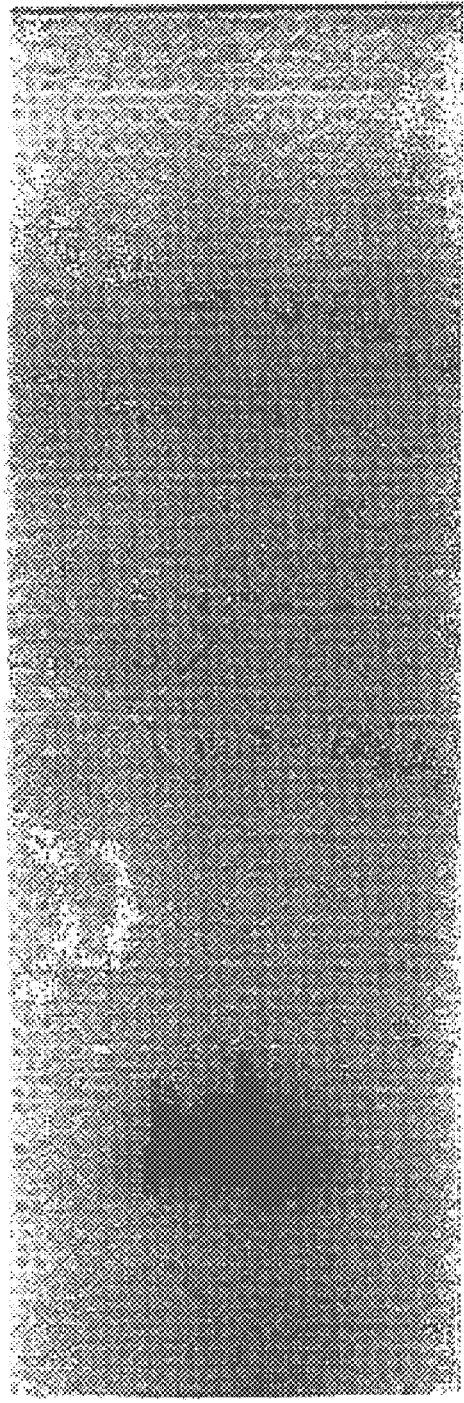

FIG. 2 is a photographic representation showing resolution of Cohn Fraction III TABM. Purified TABM (FIG. 1) were reduced with 5% v/v β2-mercaptoethanol and 400 ng resolved by SDS-PAGE in an 10–15% w/v polyacrylamide gradient gel. Proteins were visualised by silver stain. Molecular weights were determined by the mobility of pre-stained standard proteins.

Figure 3:
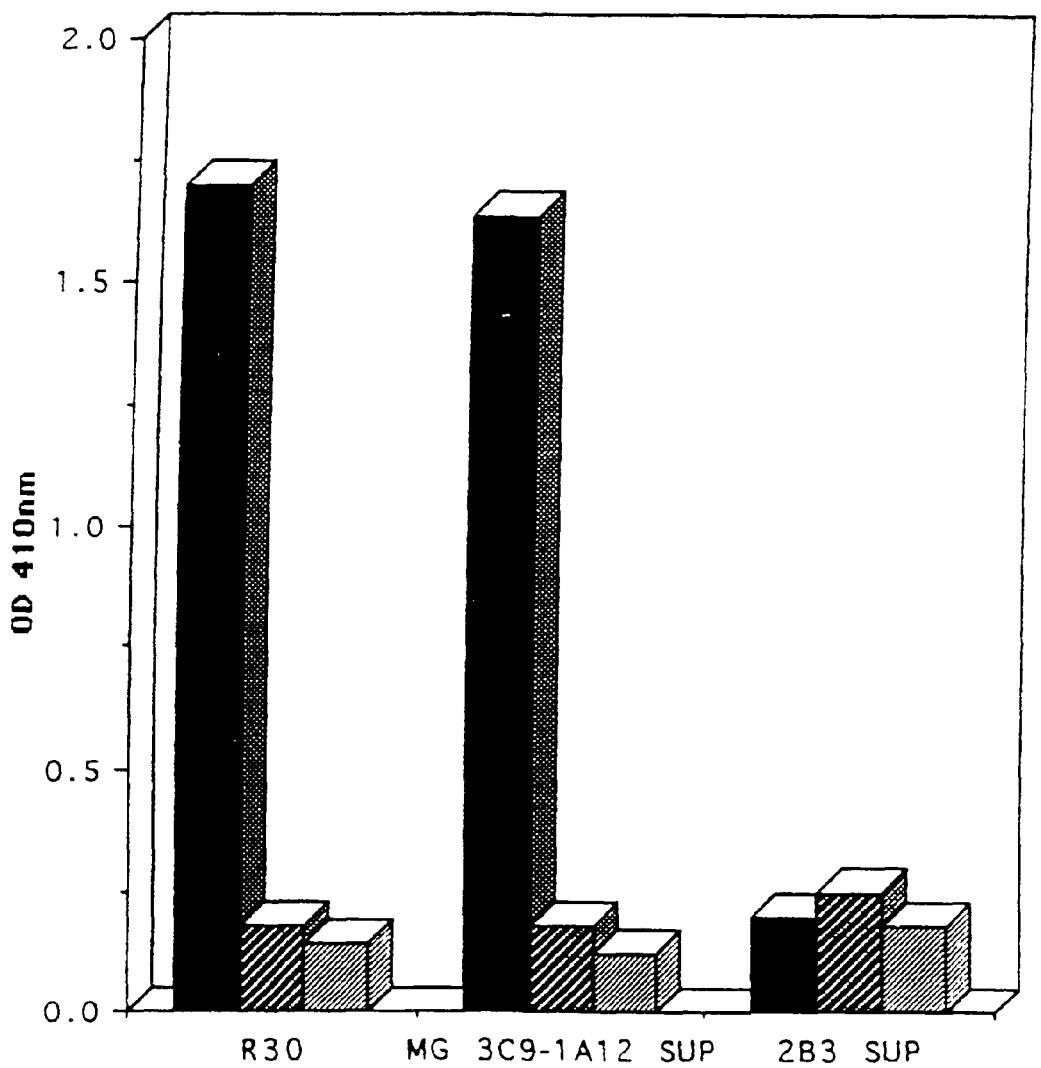

FIG. 3 is a graphical representation showing that monoclonal antibody MG3C9-1A12 binds TABM. Microtiter trays were coated with 500 ng TABM, IgG or IgM, and 100 μl 1:300 rabbit anti-TABM (R30), or 1:100 culture supernatant from clone MG3C9-1A12 or 2B3 was added to the wells. Bound antibodies were developed with alkaline phosphatase-conjugated goat anti-rabbit or mouse IgG.

Figure 4A:
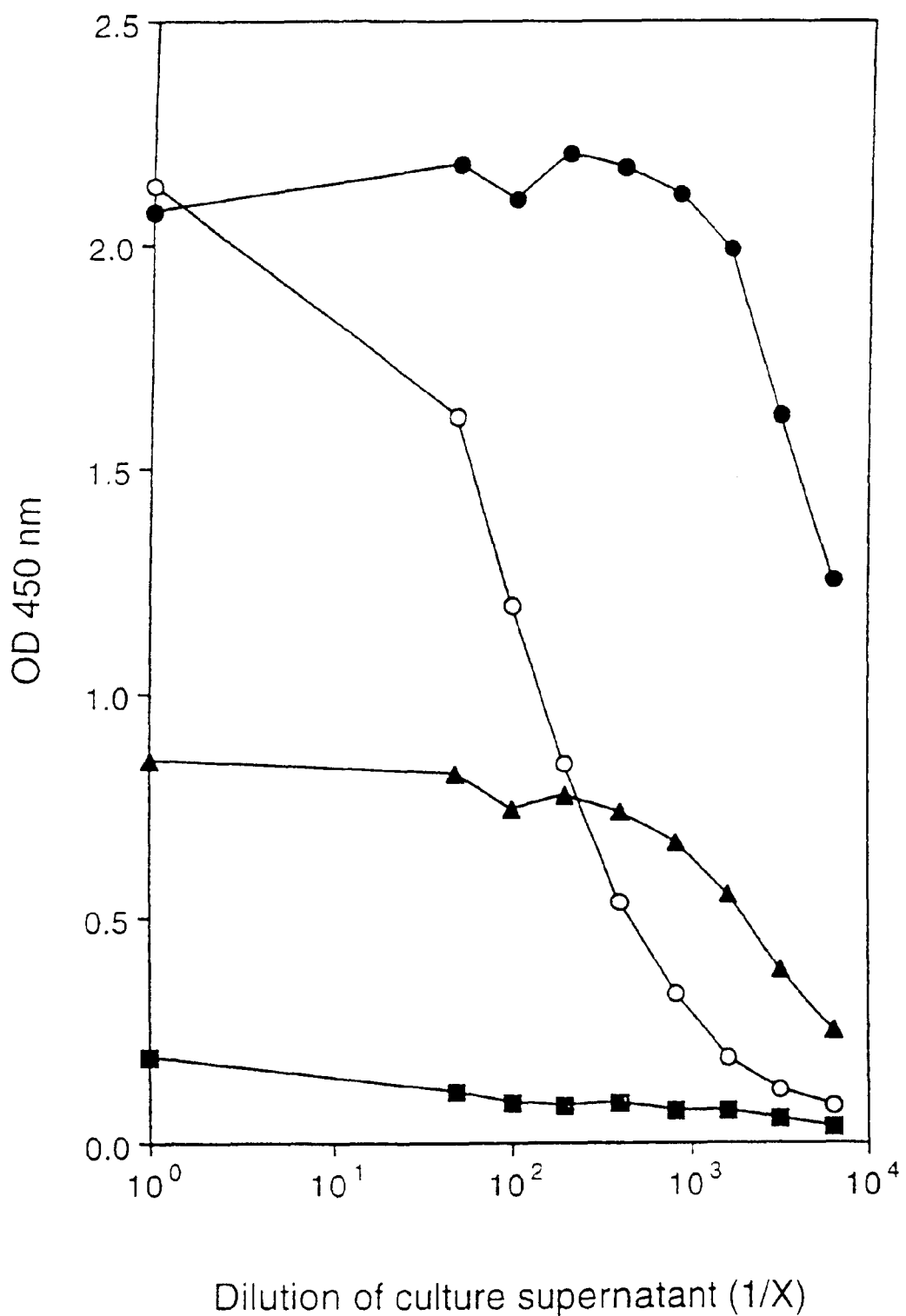
Figure 4B:
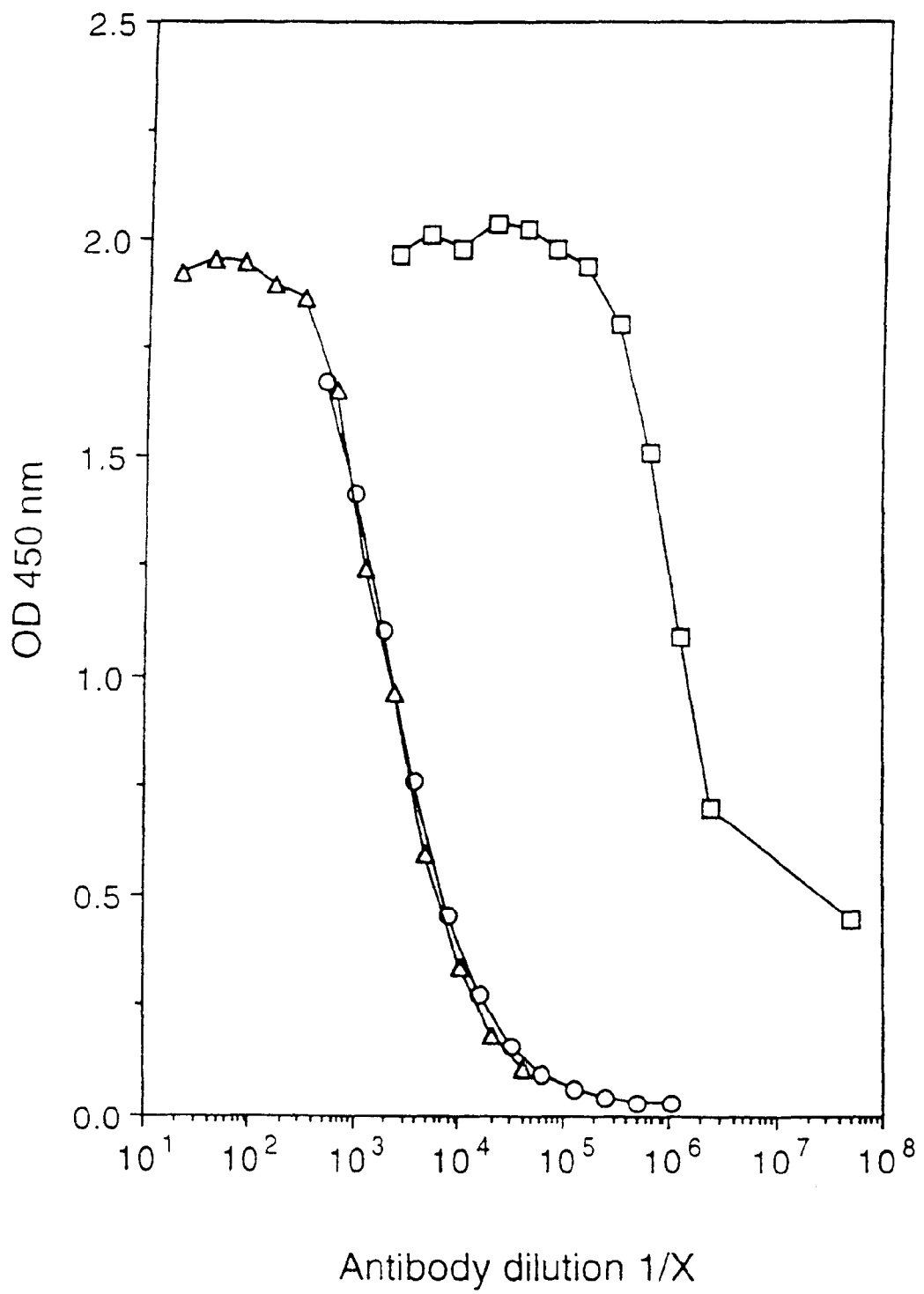

FIGS. 4A–4B are a graphical representation of the titration of monoclonal antibodies MG3C9-1A12 and sub-clone MG3C9-1A12. Microtiter trays were coated with 5–500 ng TABM/well and dilutions of antibody, culture supernatants or ascites added to the wells. Bound antibody was developed with peroxidase-conjugated goat anti-mouse IgG. A) Activity of pre-cloning "parent" hybridoma MG33C9 and sub-clones.

—○— MG3C9, 500 ng/well hTABM
—●— CLONE 1A12, 500 ng/well h TABM
—▲— CLONE 1A12, 50 ng/well h TABM
—■— CLONE 1A12, 5 ng/well h TABM B) Activity of MG3C9-1A12 culture supernatant, protein G-purified antibody and ascitic fluid. The curves show overlap, because "all" antibody was isolated by protein G, then taking into account the concentration of the purified antibody, the curves overlapped.

—○— Supernatant MG3C9-1A12
—△— Prot-G punfied MG3C9-1A12 supernatant
—□— Mouse ascites, MG3C9-1A12

Figure 4C:
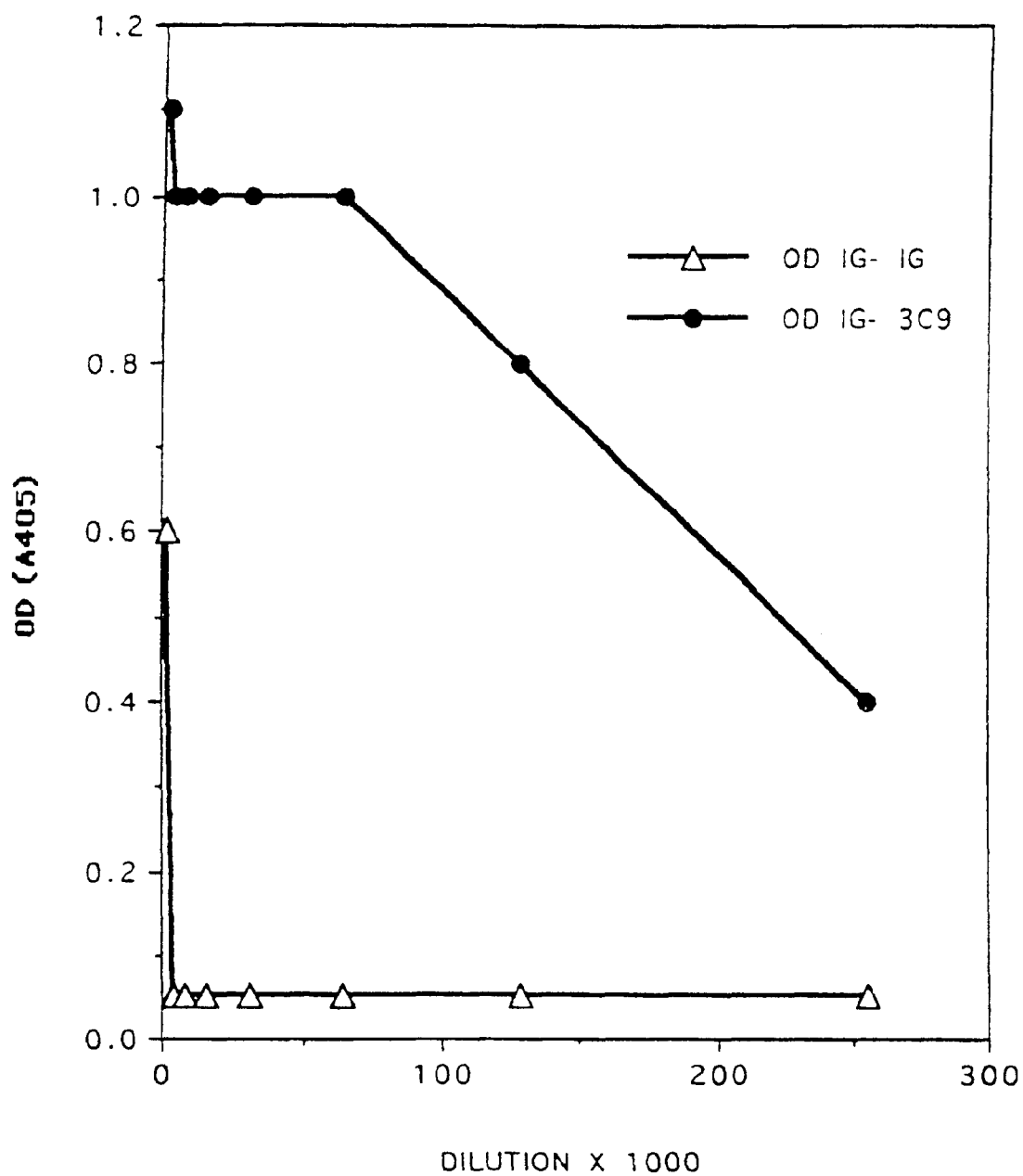

FIG. 4C is a graphical representation of dilutions of human Immunoglobulin negative serum coated to microtiter trays and then assayed for TABM using MG-b 3C9-1A12 (1:1000). The serem has a TABM "titer" of >256,000 and no immunoglobulin (Ig-,Ig) was detected in this serem.

—△— OD IG- IG
—●— OD IG- 3C9

Figure 5:
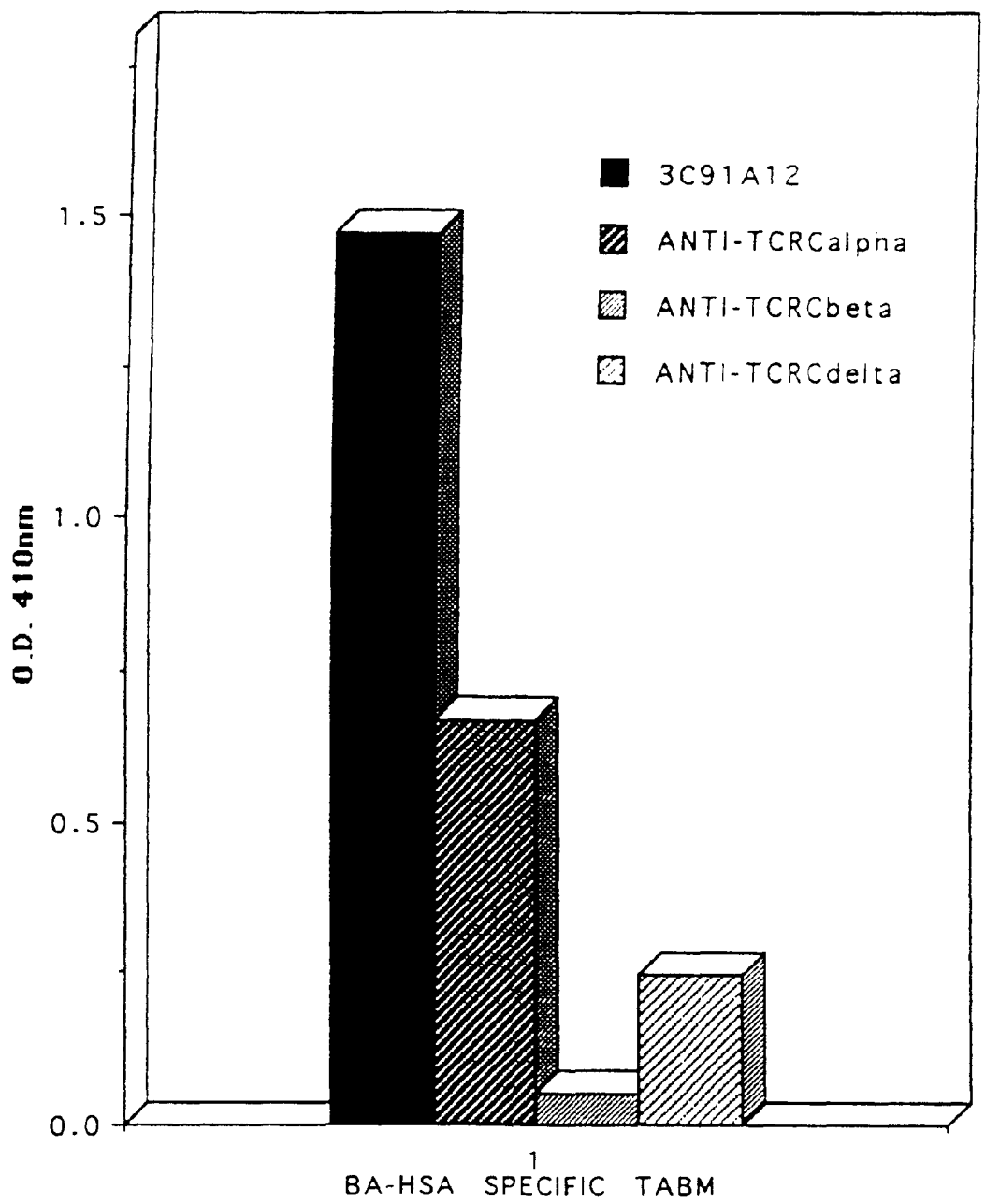

FIG. 5 is a graphical representation showing that BA-Specific, MG3C9-1A12+TABM bear TcRα epitopes. Serum from a patient with a high titer of TABM to BA-HSA individual was absorbed to MG3C9-1A12-sepharose beads. The beads were eluted, and the eluate proteins absorbed to BA-HSA-sepharose beads. The eluted proteins were coated to microtiter wells at 200 ng/well. Monoclonal MG3C9-1A12, anti-TcR Cα-1, Cβ-1, or Cδ-1 (1:100) was added to the wells, and bound antibody detected with alkaline phosphatase-conjugated goat anti-mouse IgG.

Figure 6:
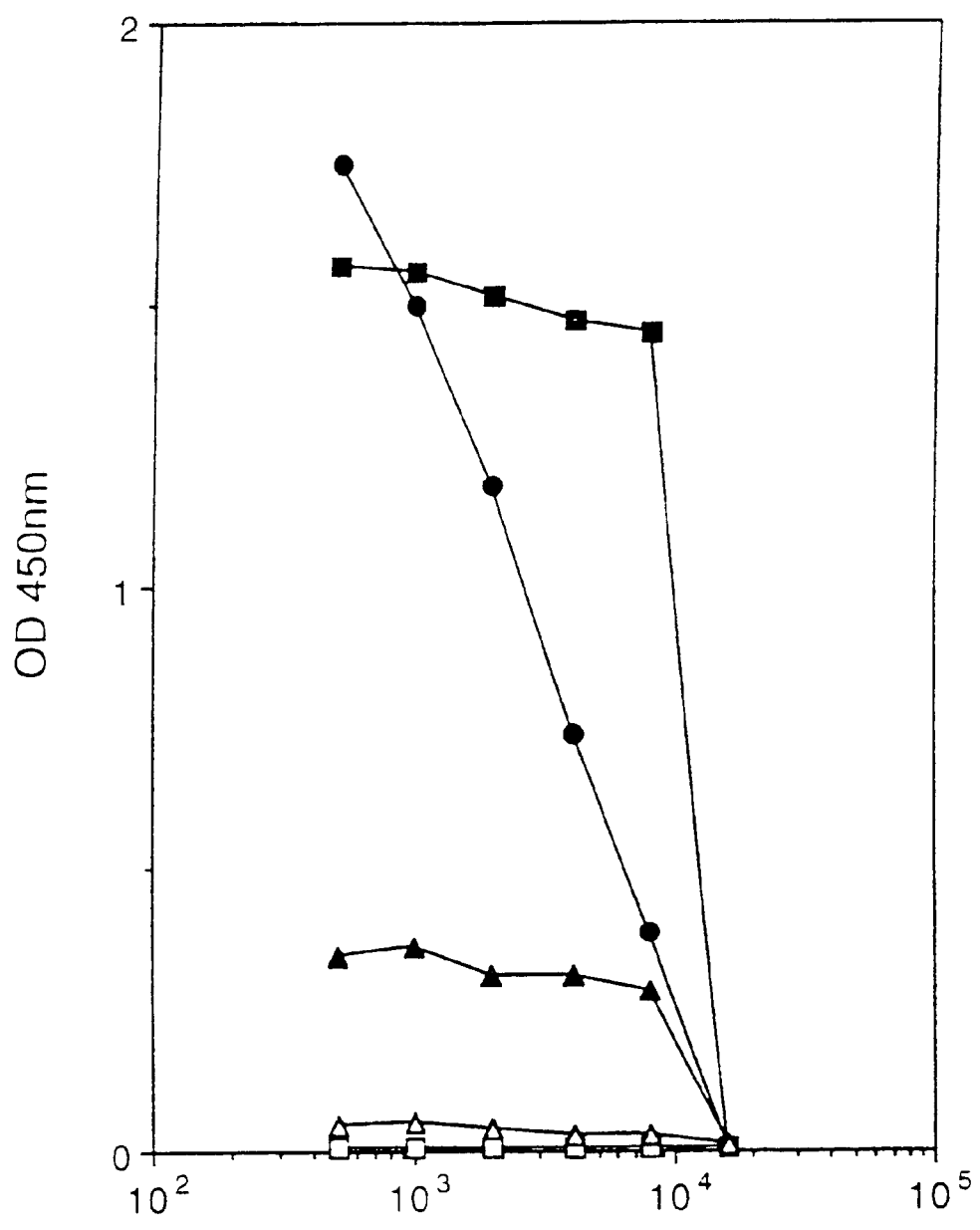

FIG. 6 is a graphical representation showing the MG3C9-1A12 antibody detects TABM in human and primate serum. Human (Cohn Fraction III) TABM (hTABM) or 100 μl of dilutions of fetal calf serum (FCS), cynomologous monkey or sheep and human serum were coated to wells of microtiter trays. A 1:1000 dilution of protein G-purified monoclonal MG3C9-1A12 was added, and bound antibody detected with peroxidase-conjugated sheep anti-mouse IgG.

—●— hTABM
—□— FCS
—▲— MONKEY
—■— HUMAN
—△— SHEEP

Figure 7:
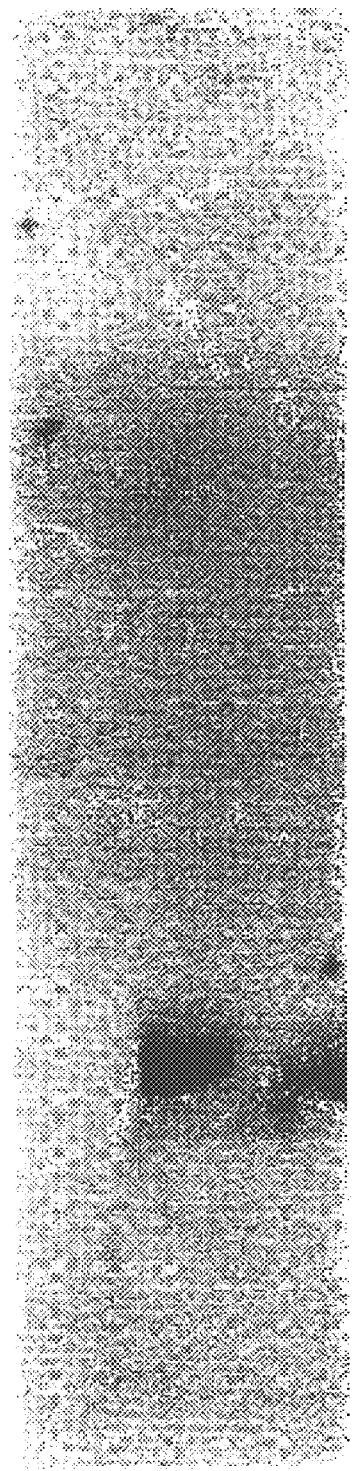

FIG. 7 is a photographic representation of immunoblotting of TABM and serum with monoclonal MG3C9-1A12. Two hundred fifty μl of a 1:50 dilution of normal human serum, and 15 μg of Cohn Fraction III TABM were reduced with 5% v/v β2-mercaptoethanol, and 4 μl of a 1:50 dilution of serum or 240 ng TABM were resolved in an 8–25% w/v polyacrylamide gel. Proteins in the electrophoresed gel was transferred to an immobilon membrane and blotted with 10 ml of a 1:1000 dilution of protein G-purified MG3C9-1A12. Molecular weights were determined by the mobilities of pre-stained standard proteins.

Figure 8:
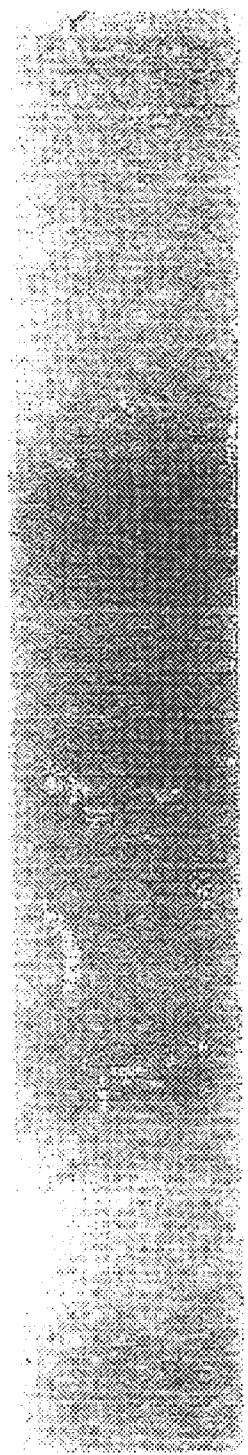
Figure 8:
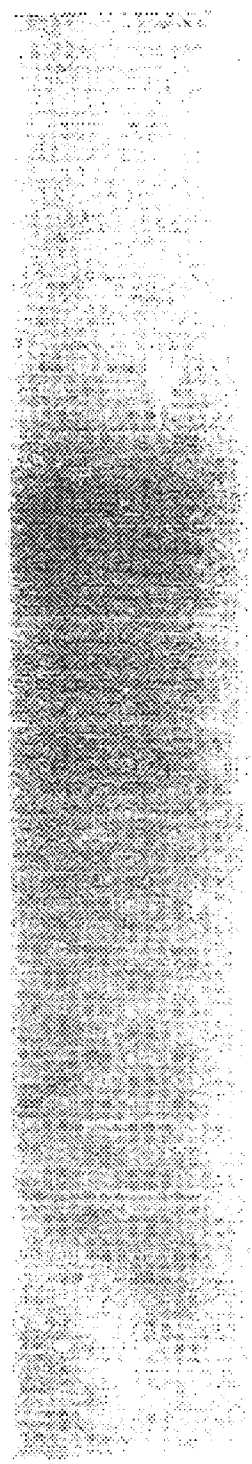

FIG. 8 is a photographic representation of a resolution of Jurkat proteins bound by Monoclonal MG3C9-1A12. $1 \times 10^7$ Jurkat (T) or A1 (B) cells were lysed with 1 ml 1.0% v/v Triton X-100. The lysate was absorbed with 200 μl monoclonal MG3C9-1A12-sepharose beads. The washed beads were eluted with 0.5 ml SDS-PAGE sample buffer and reduced by the addition of 5% v/v β₂-mercaptoethanol. Four μl of the eluate was resolved in an 8–25% v/v polyacrylamide gradient. 1:Jurkat, 2:A1 proteins are silver stained. Molecular weights were determined by the mobilities of pre-stained molecular weight standards.

Figure 8B:
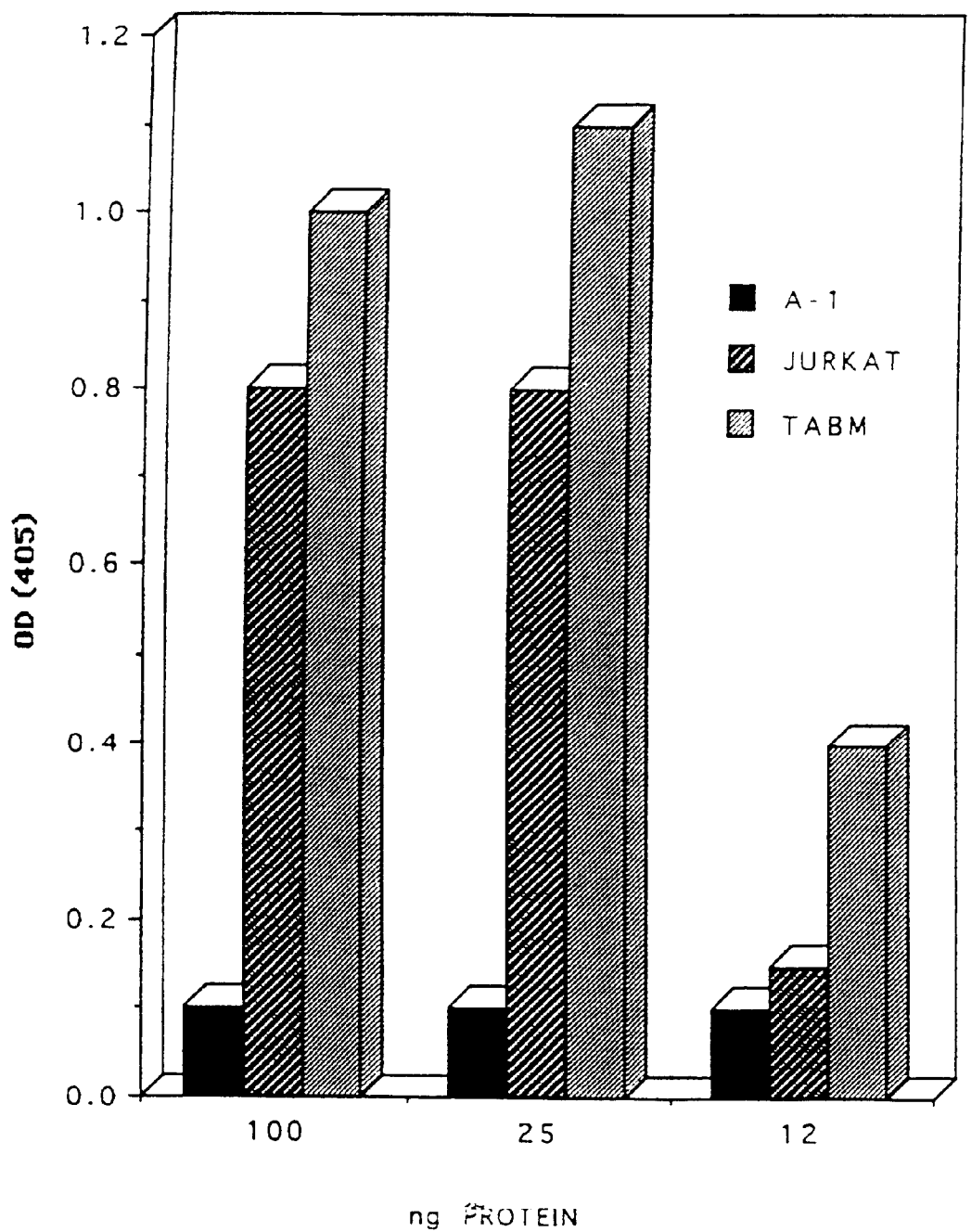

FIG. 8B is a graphical representation of detergent lysdates of the human T-cell line Jurkat and the B-cell (leukaemia) line A-1 absorbed to MG3C9-1A12-Sepharose and the column eluted with 0.1 M $NaCO_3$. The eluates were used to coat microtiter trays and assayed with MG3C9-1A12. The B-cell line is negative for TABM.

■ A-1
■ JURKAT
■ TABM

Figure 9:
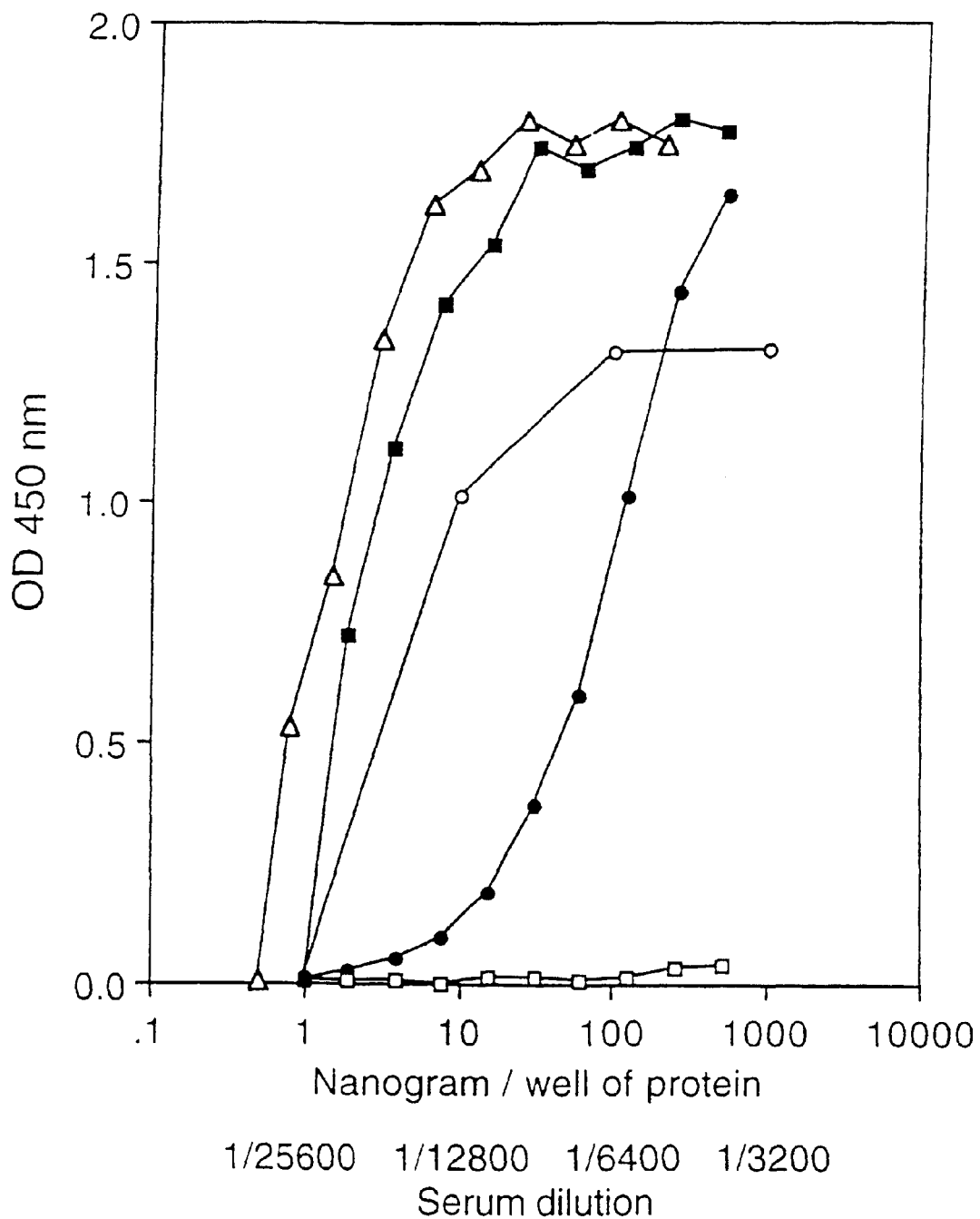

FIG. 9 is a graphical representation showing the presence of TABM in different fractions. Patient serum and different TABM preparations were serially diluted and plated onto ELISA plates. The amount of TABM was determined using the mouse monoclonal anti-human TABM antibody (MG3C9-1A12).

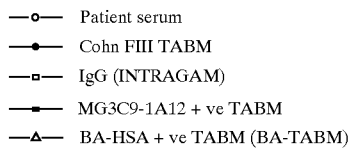

Figure 10A:
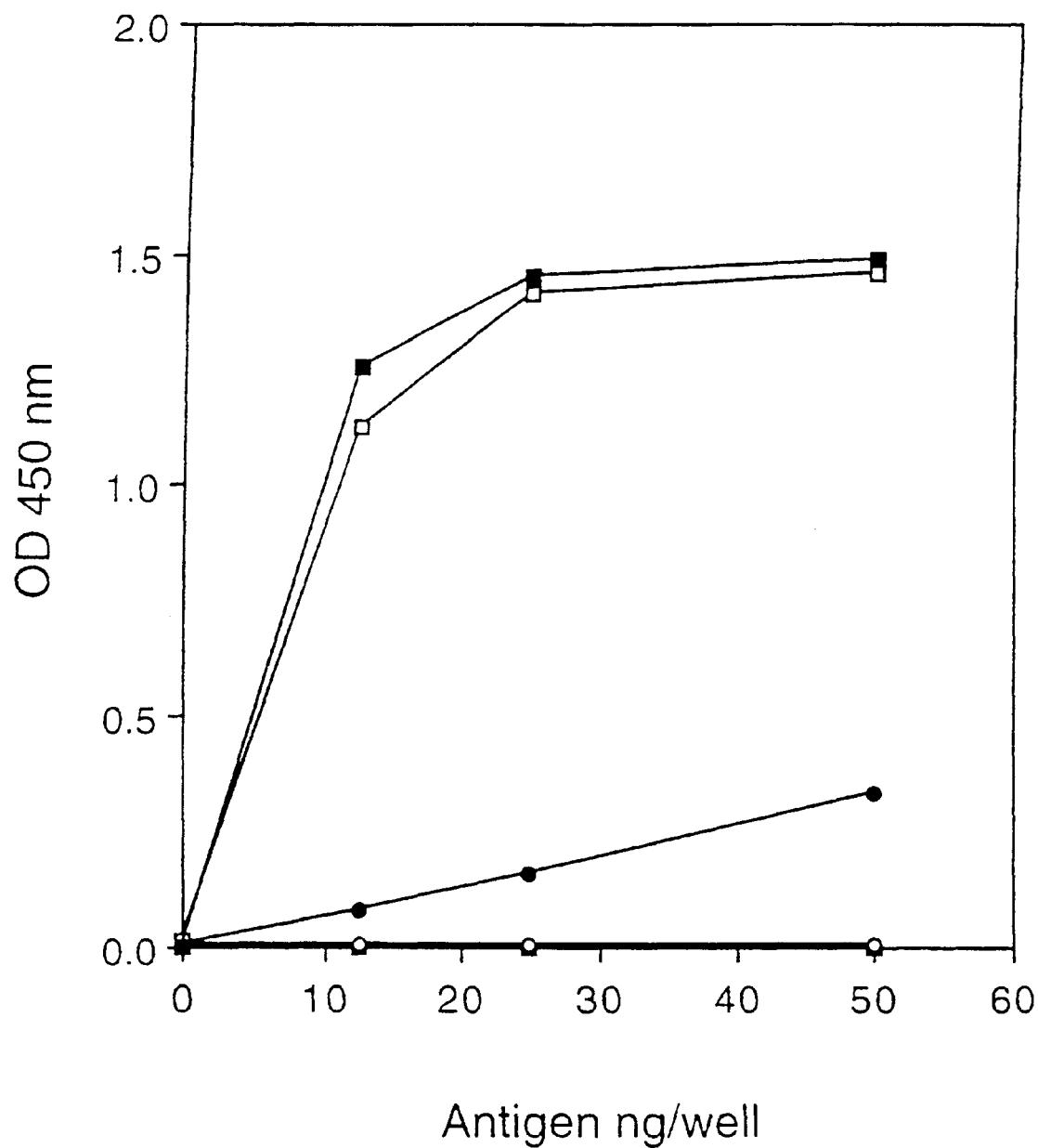
Figure 10B:
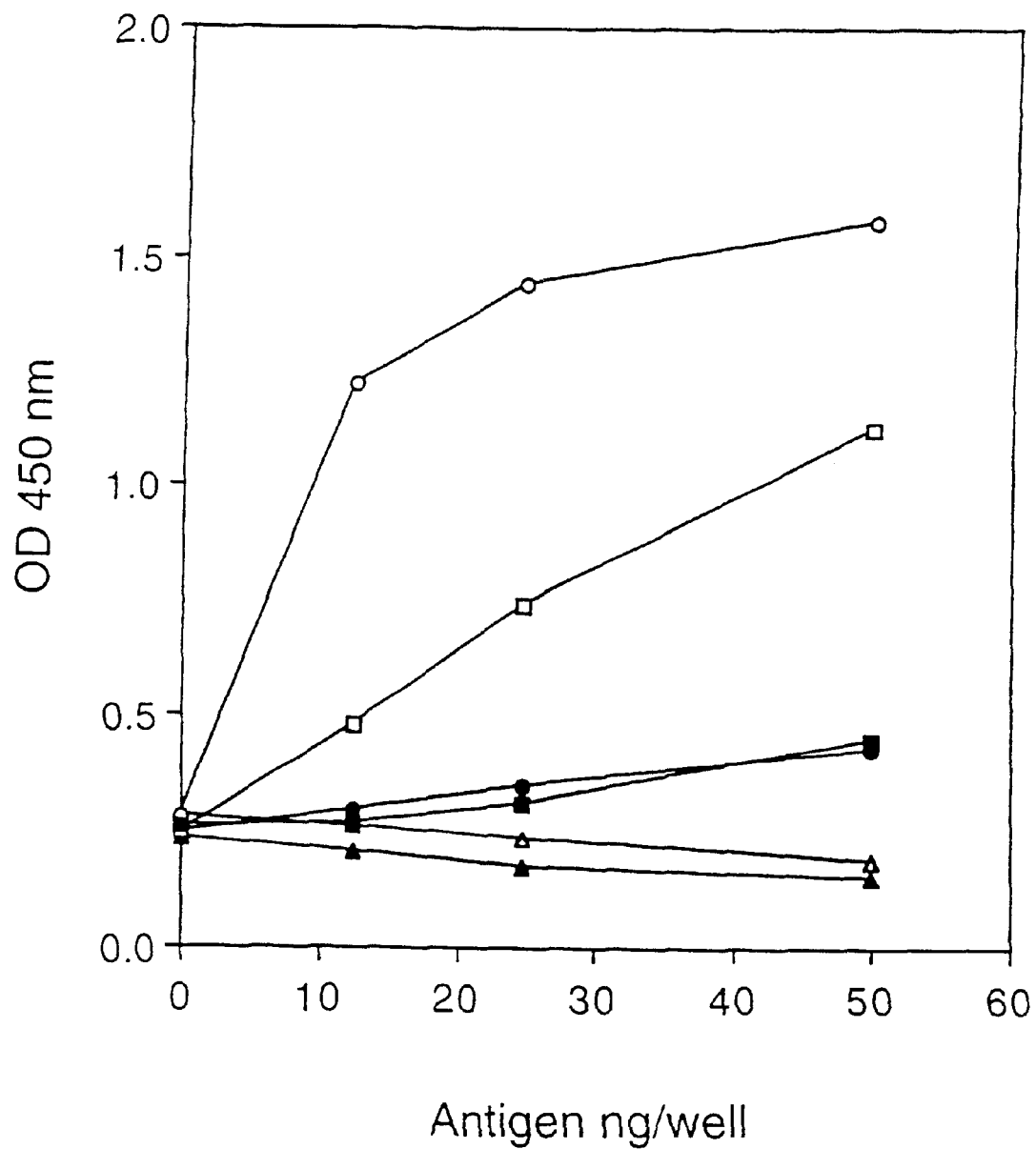

FIGS. 10A–10B are a graphical representation showing the determination of TABM and IgG levels in different fractions. Different amounts of TABM were coated directly onto ELISA plates and (A) the presence of TABM was detected using the monoclonal anti-human TABM antibody. The presence of IgG (B) was detected using a peroxidase labelled sheep anti-human IgG.

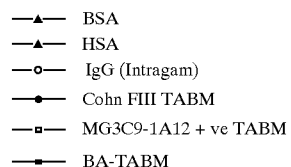

Figure 11A:
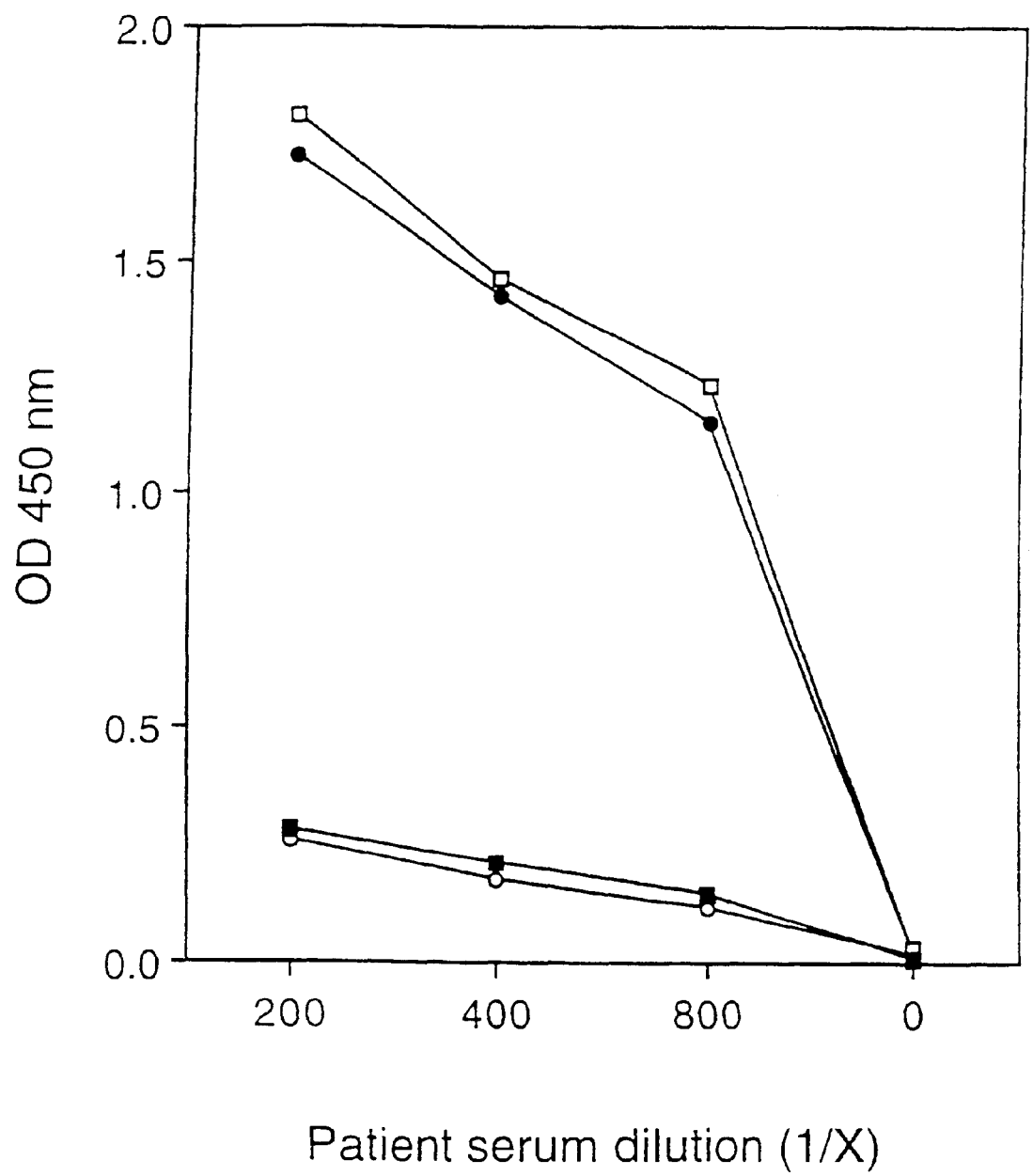
Figure 11B:
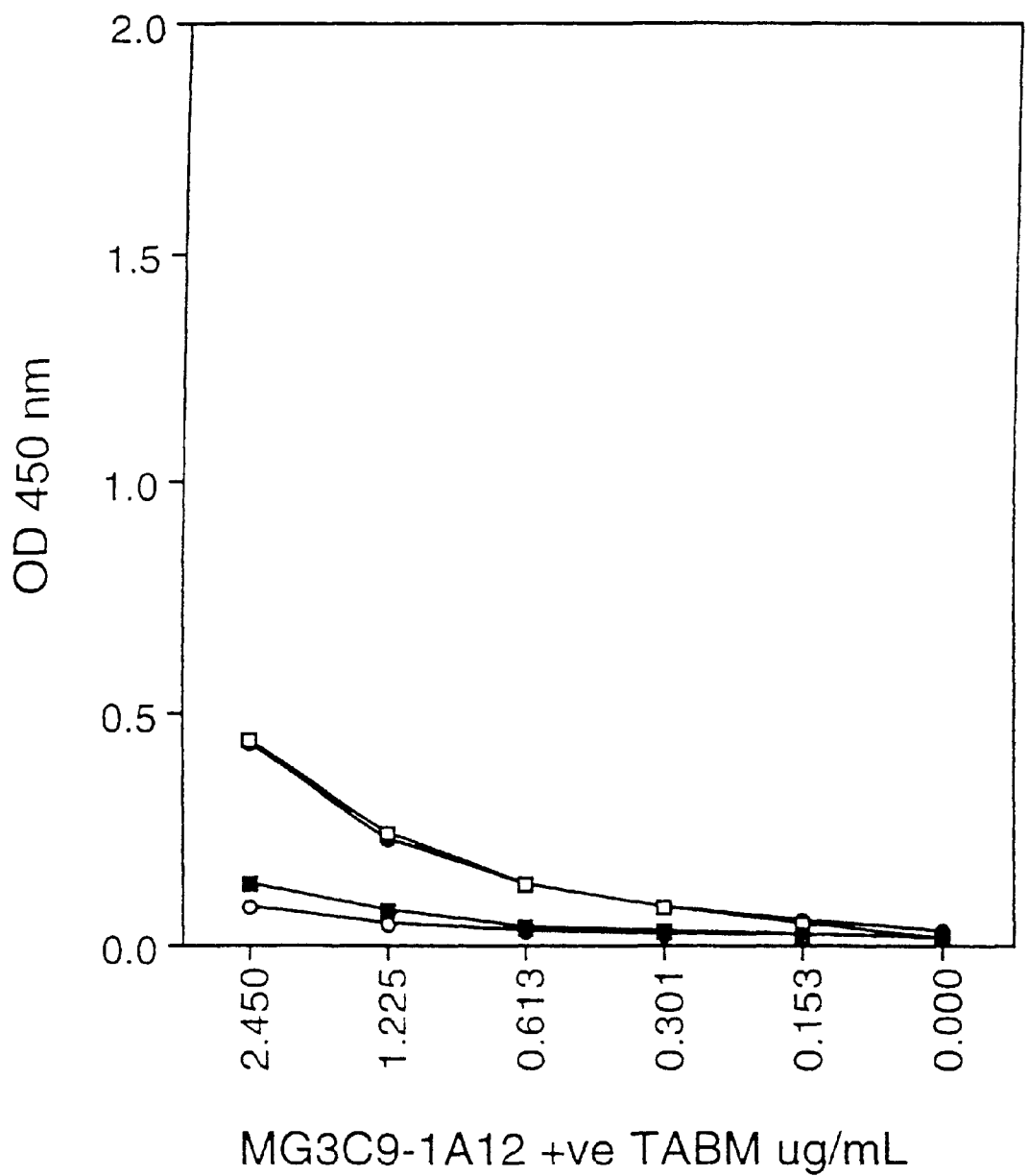
Figure 11C:
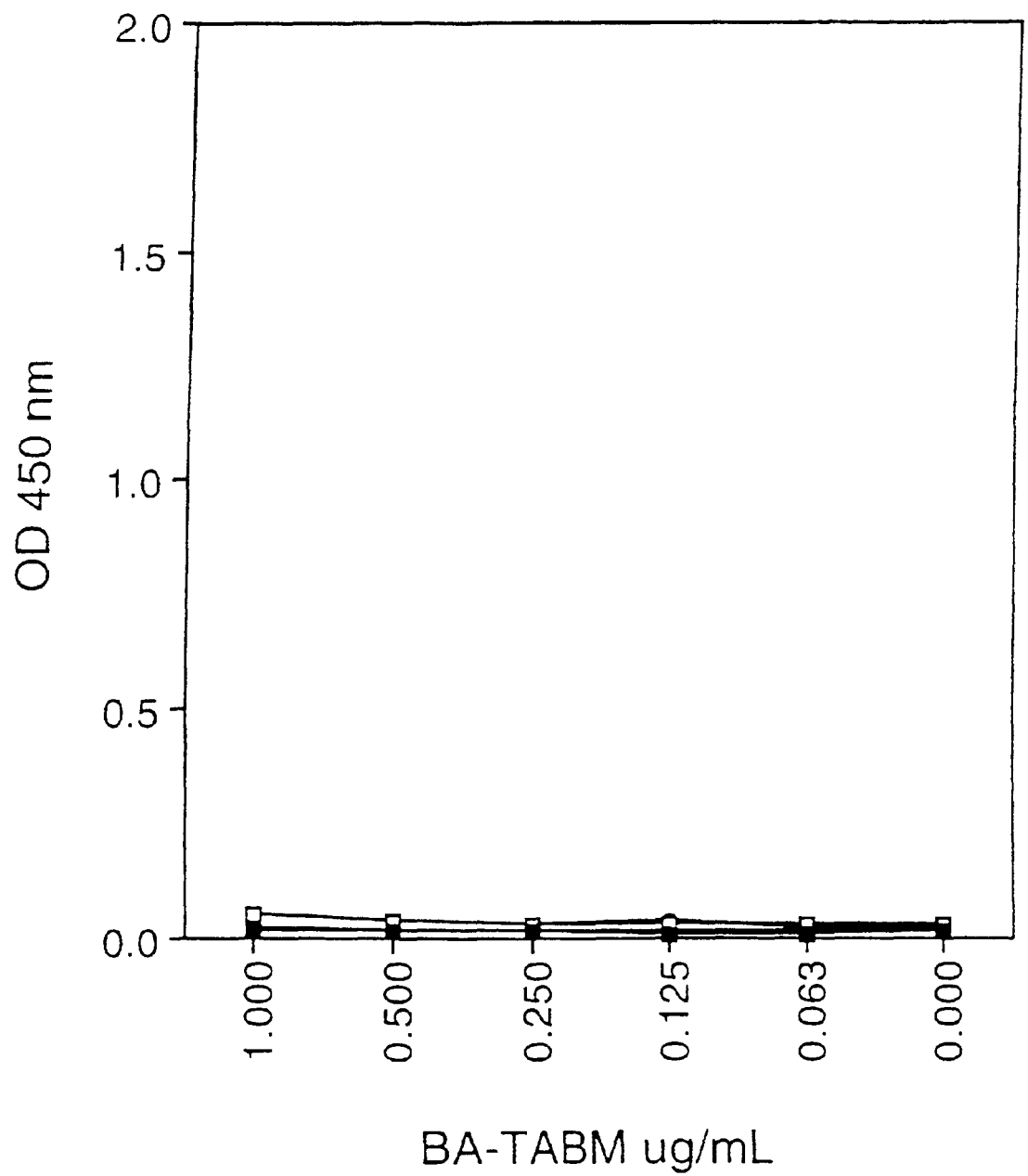

FIGS. 11A–11C are a graphical representation of the determination of antigen specific IgG in various samples to different haptens. Various haptens were coated onto ELISA plates at 250 ng/well. The patient serum (A), MG3C9-1A12+ve TABM (B) and the purified BA-HSA specific TABM, BA-TABM (C) were serially diluted and tested for IgG to the haptens.

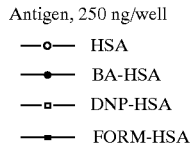

Figure 12A:
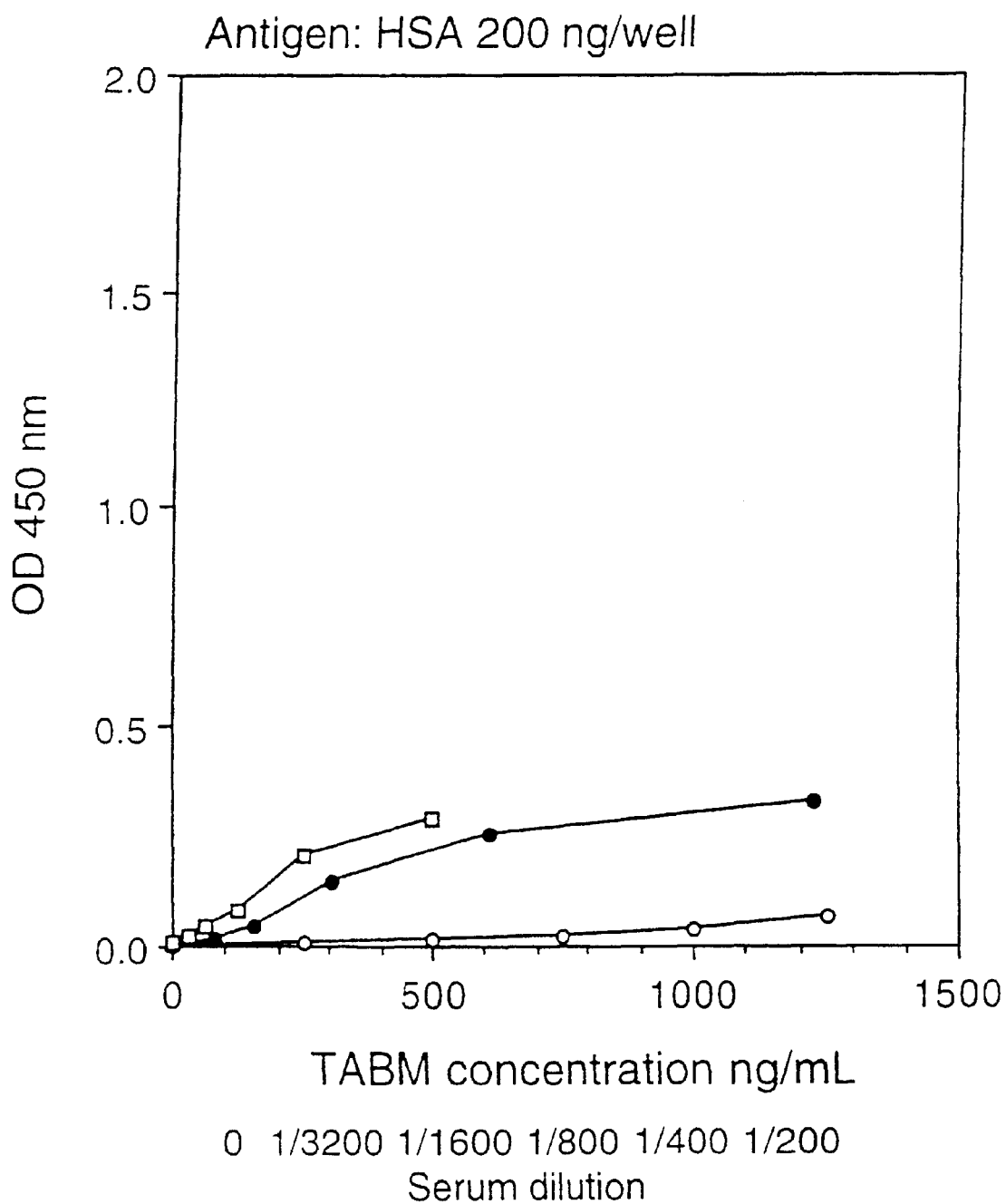
Figure 12B:
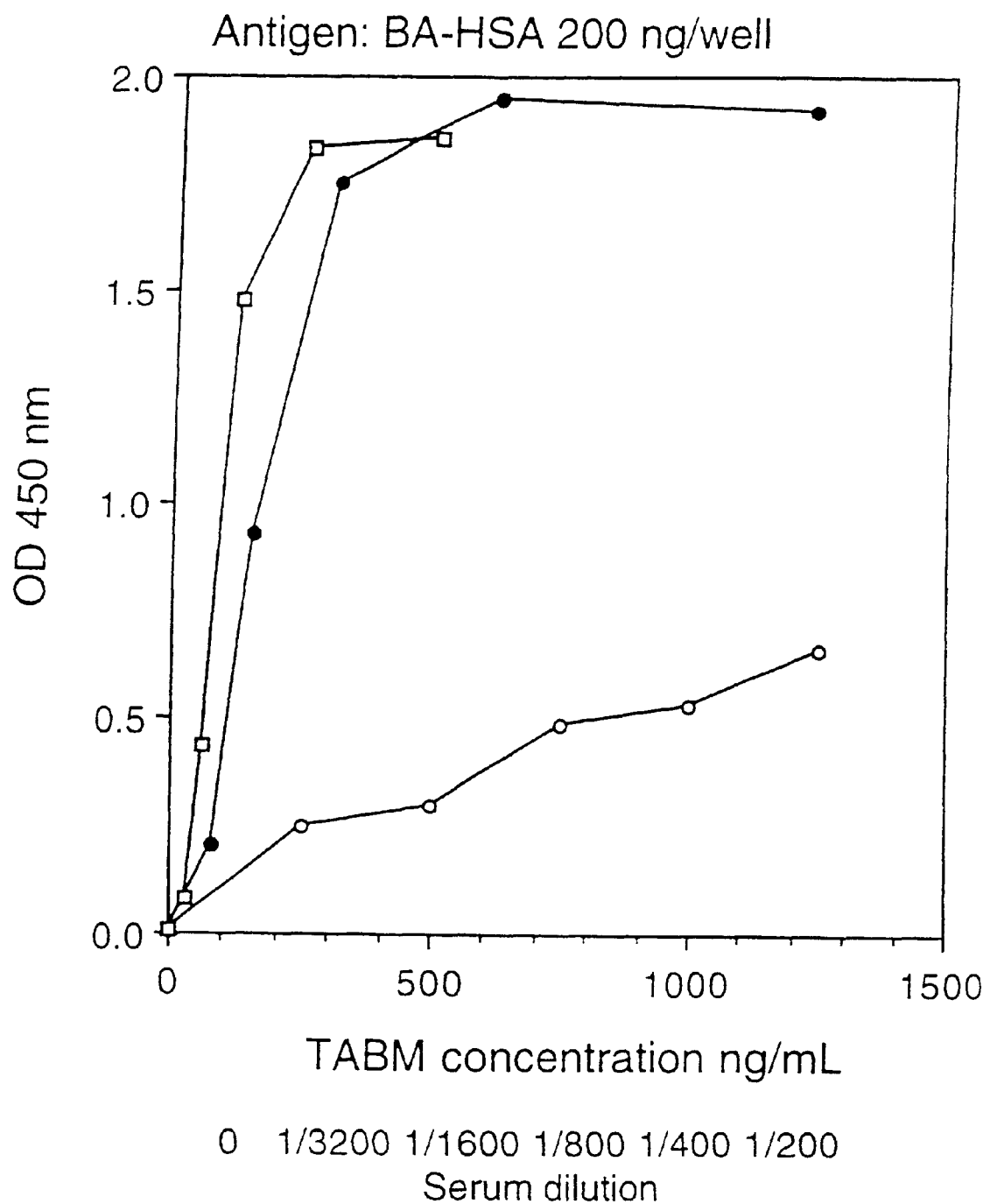

FIGS. 12A–12B are a graphical representation showing detection of antigent specific TABM in different fractions. HSA (A) and BA-TABM (B) were coated onto ELISA plates. The patient serum and TABM preparations were serially diluted and tested for the presence of antigen specific TABM using the mouse monoclonal anti-human TABM antibody (MG3C9-1A12).

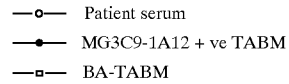

Figure 13:
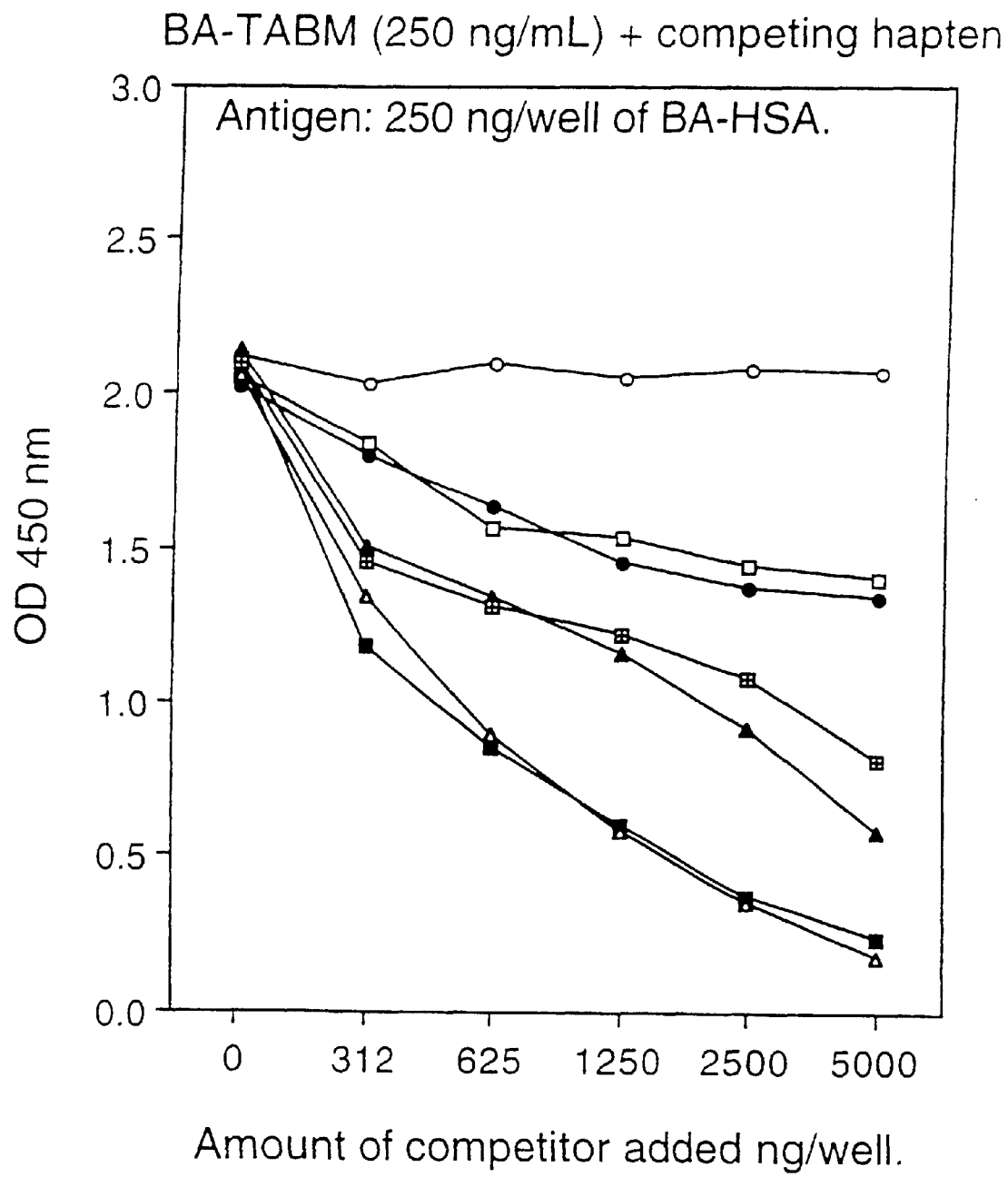

FIG. 13 is a graphical representation of competitive inhibition ELISA between BA-TABM and various haptens. Purified BA-TABM was diluted and pre-mixed with various haptens. The mixture was put onto an ELISA plate coated with the hapten BA-HSA and incubated. The amount of TABM binding as determined using the mouse monoclonal anti-human TABM antibody (MG3C9-1A12).

COMPETITOR:

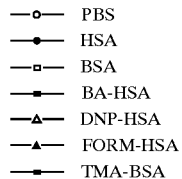

Figure 14:
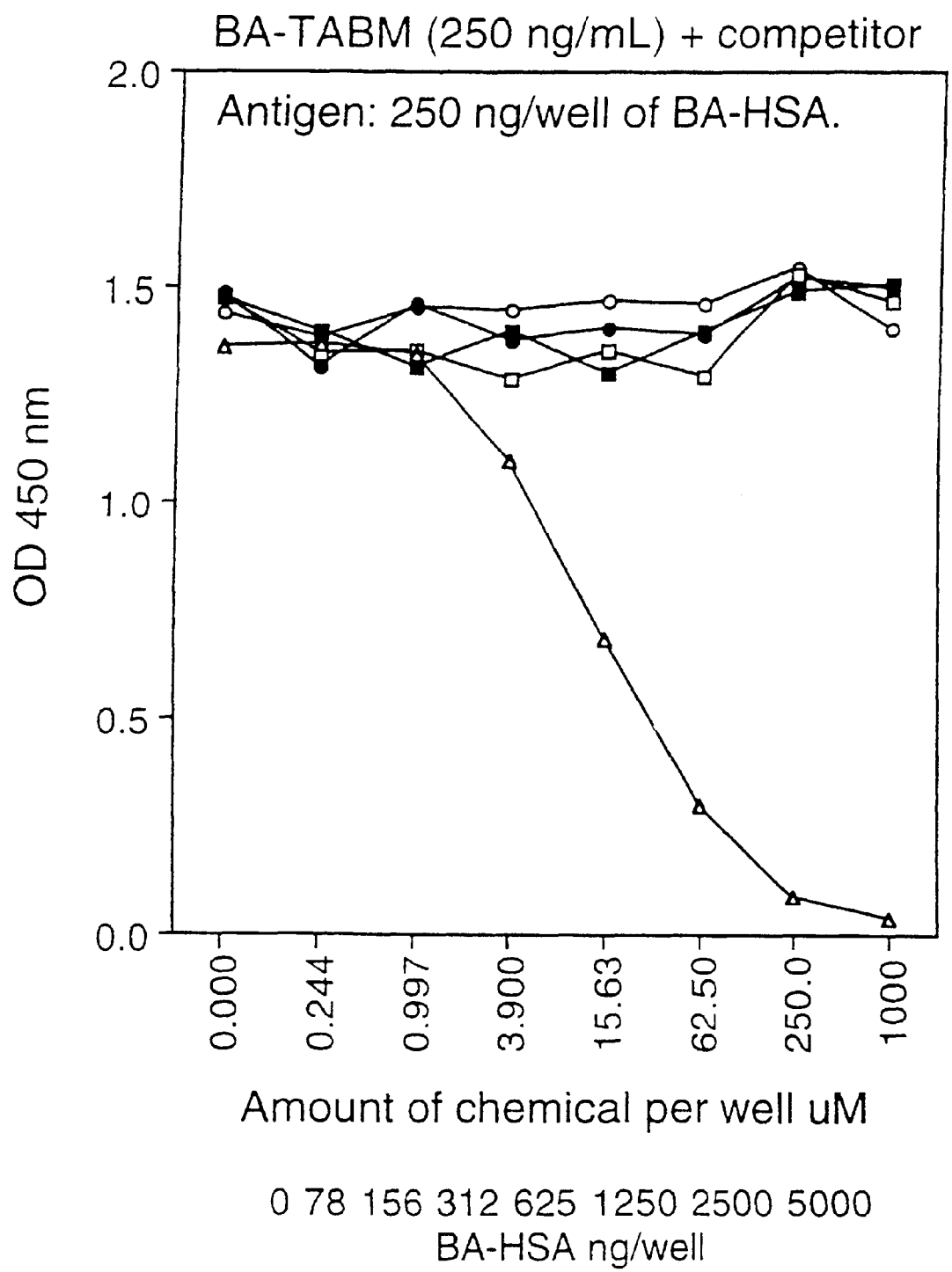

FIG. 14 is a graphical representation showing inhibition ELISA between BA-TABM and various chemicals. Purified BA-TABM was diluted and pre-mixed with various chemicals. The mixture was put onto an ELISA plate coated with the hapten BA-HSA and incubated. The amount of TABM binding was determined using the mouse monoclonal anti-human TABM antibody (MG3C9-1A12).

COMPETITOR:

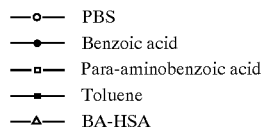

Figure 15:
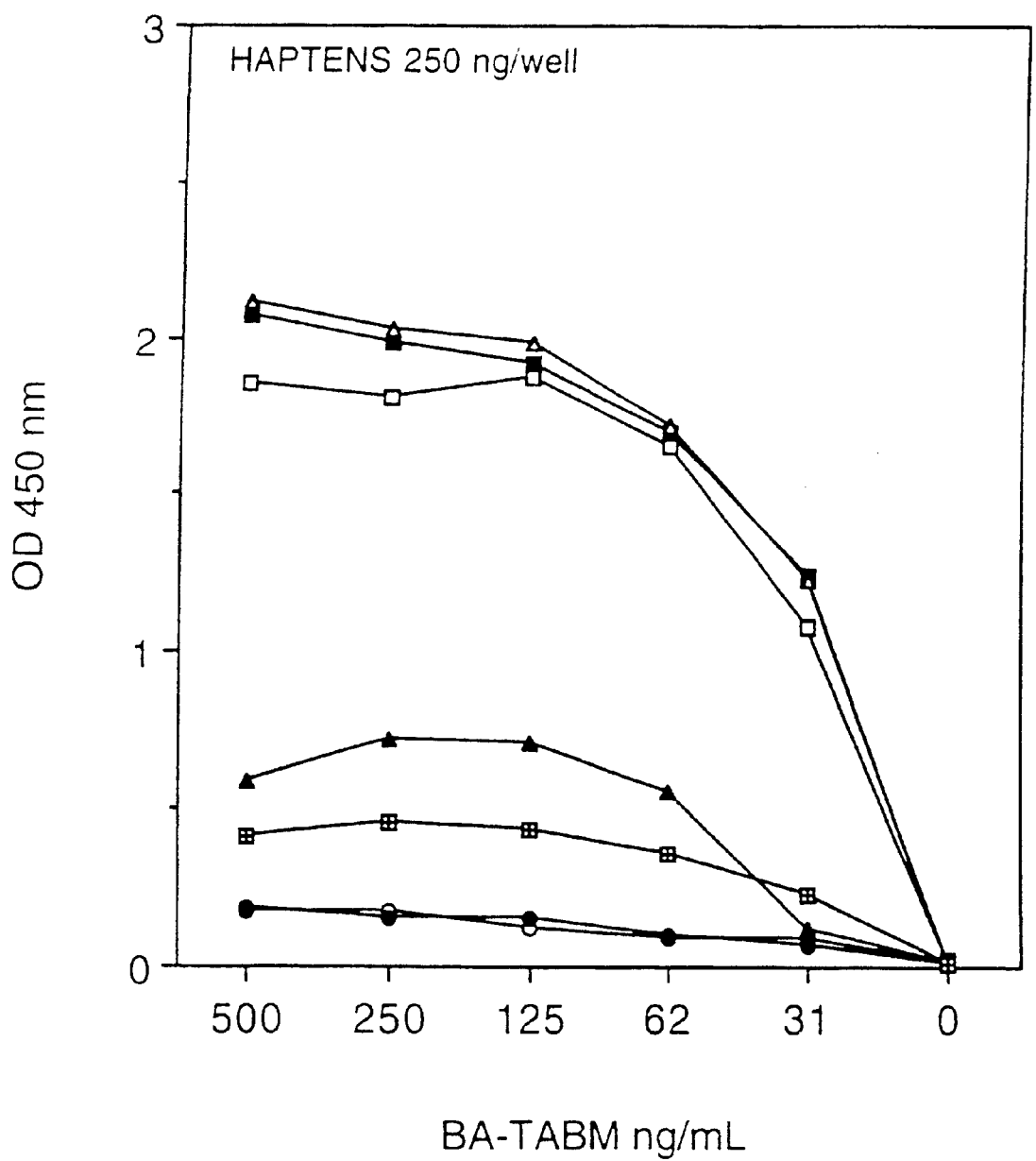

FIG. 15 is a graphical representation of the determination of the interaction of various TABM preparations and a panel of haptens. A panel of haptens were coated onto ELISA plates. Various samples and preparations of TABM (A) PBS, (B) patient serum (C) MG3C9-1A12+ve TABM and (D) BA-TABM were diluted and tested for the presence of hapten specific TABM using the mouse monoclonal anti-human TABM antibody (MG3C9-1A12).

Figure 16:
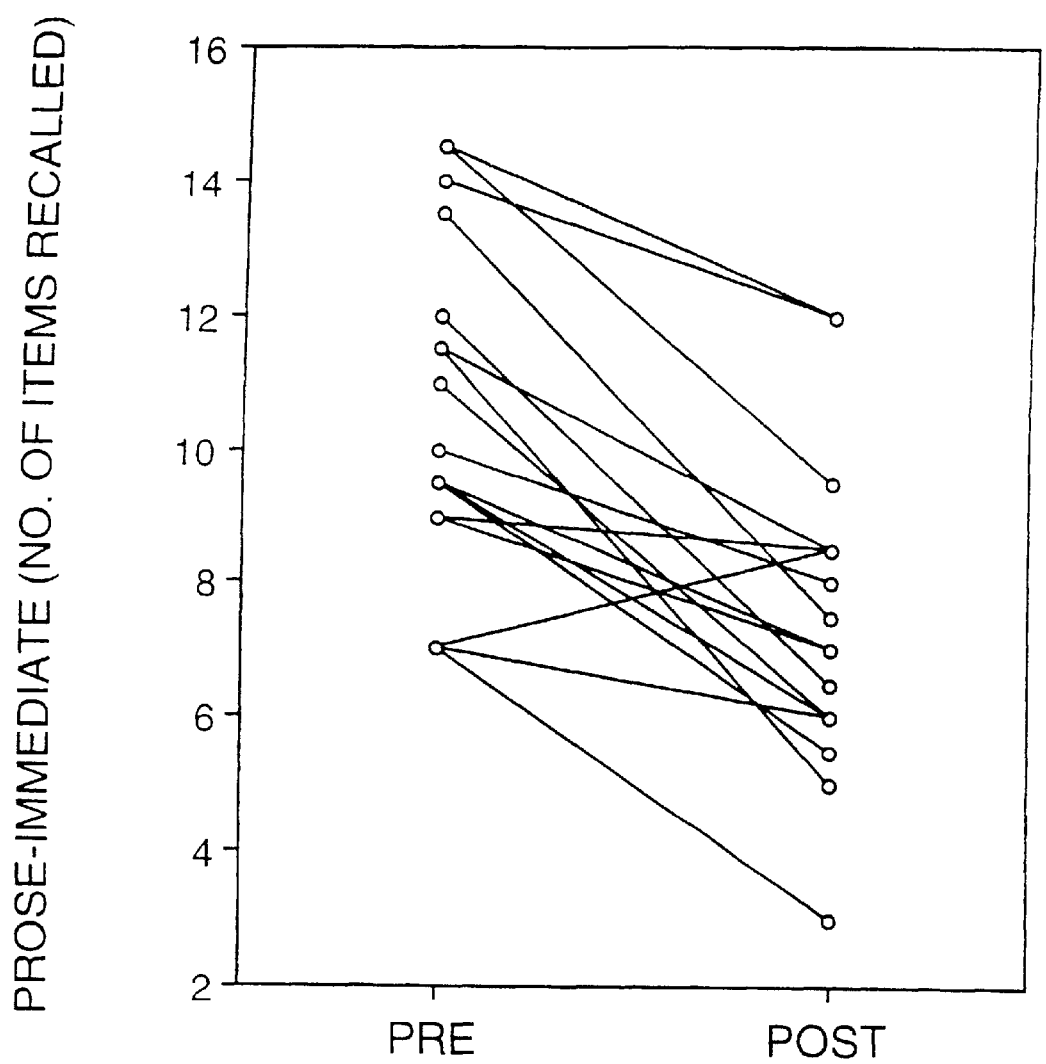

FIG. 16 is a graphical representation showing patient recall of prose (immediate), tested pre and post toluene exposure, p=0.0003.

Figure 17:
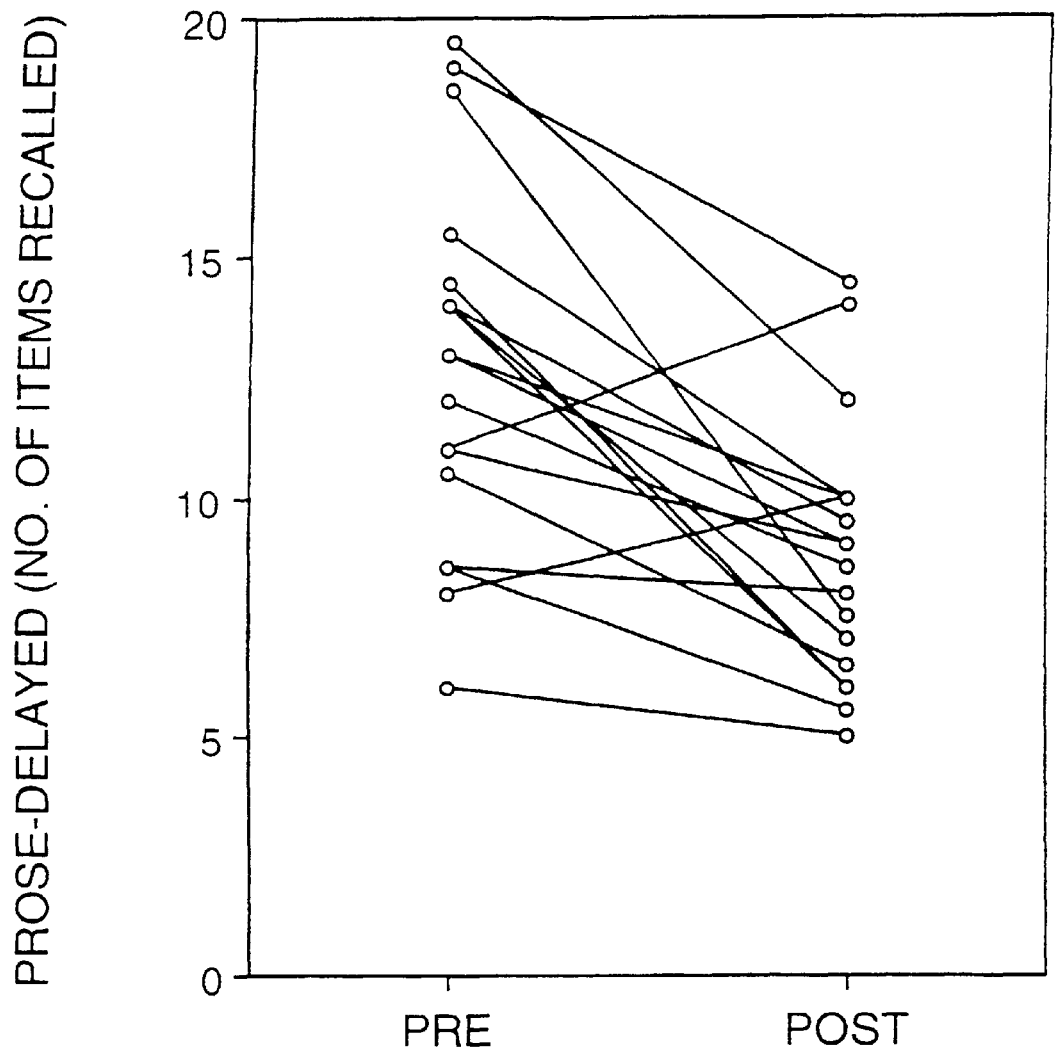

FIG. 17 is a graphical representation showing patient recall of prose (delayed), tested pre and post toluene exposure, p=0.0009.

Figure 18:
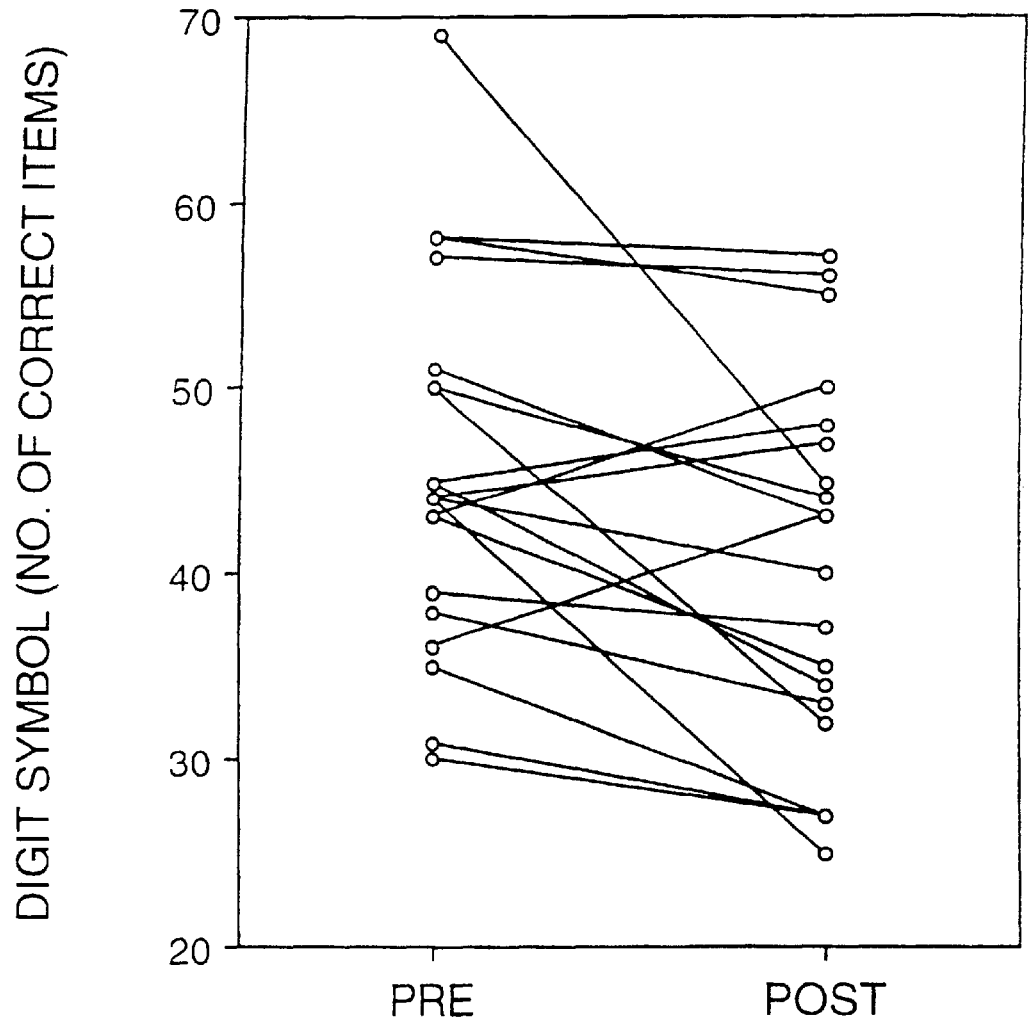

FIG. 18 is a graphical representation showing digit symbols recalled by patients pre and post toluene exposure, p=0.0099.

Figure 19:
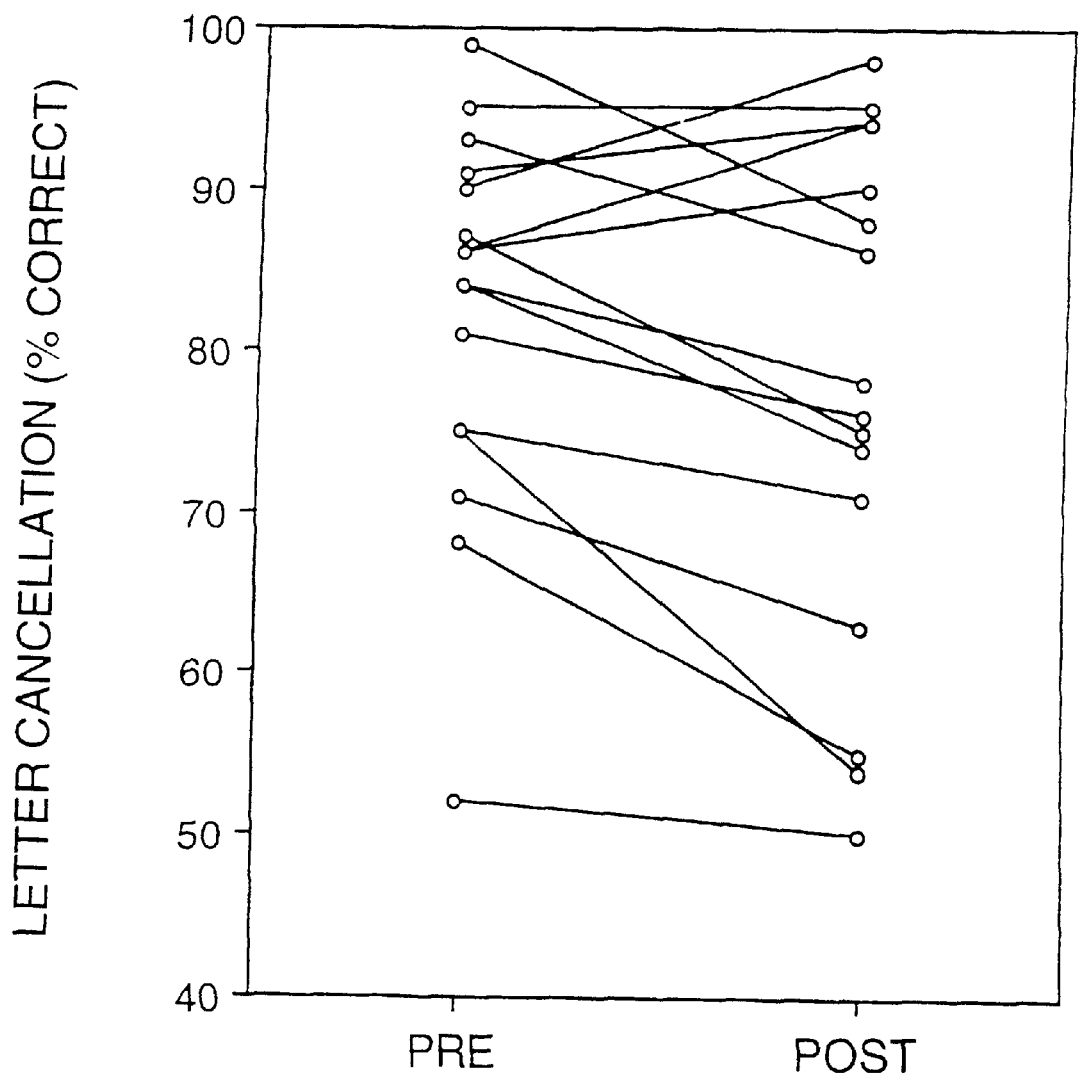

FIG. 19 is a graphical representation showing letter cancellation by patients pre and post toluene exposure, p=0.038.

Figure 20:
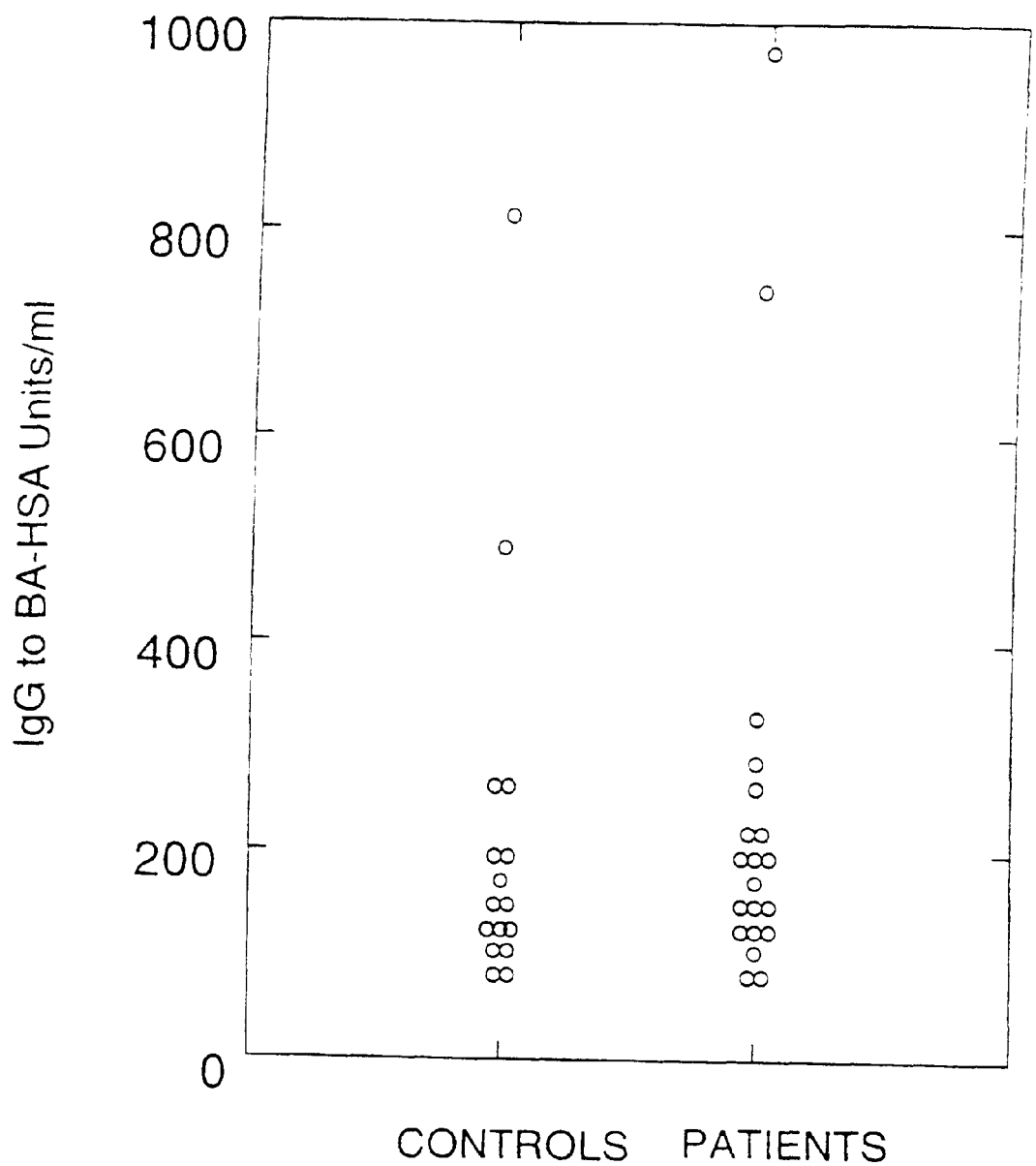

FIG. 20 is a graphical representation showing serum levels of antigen specific IgG to BA-HSA, p=0.535.

Figure 21:
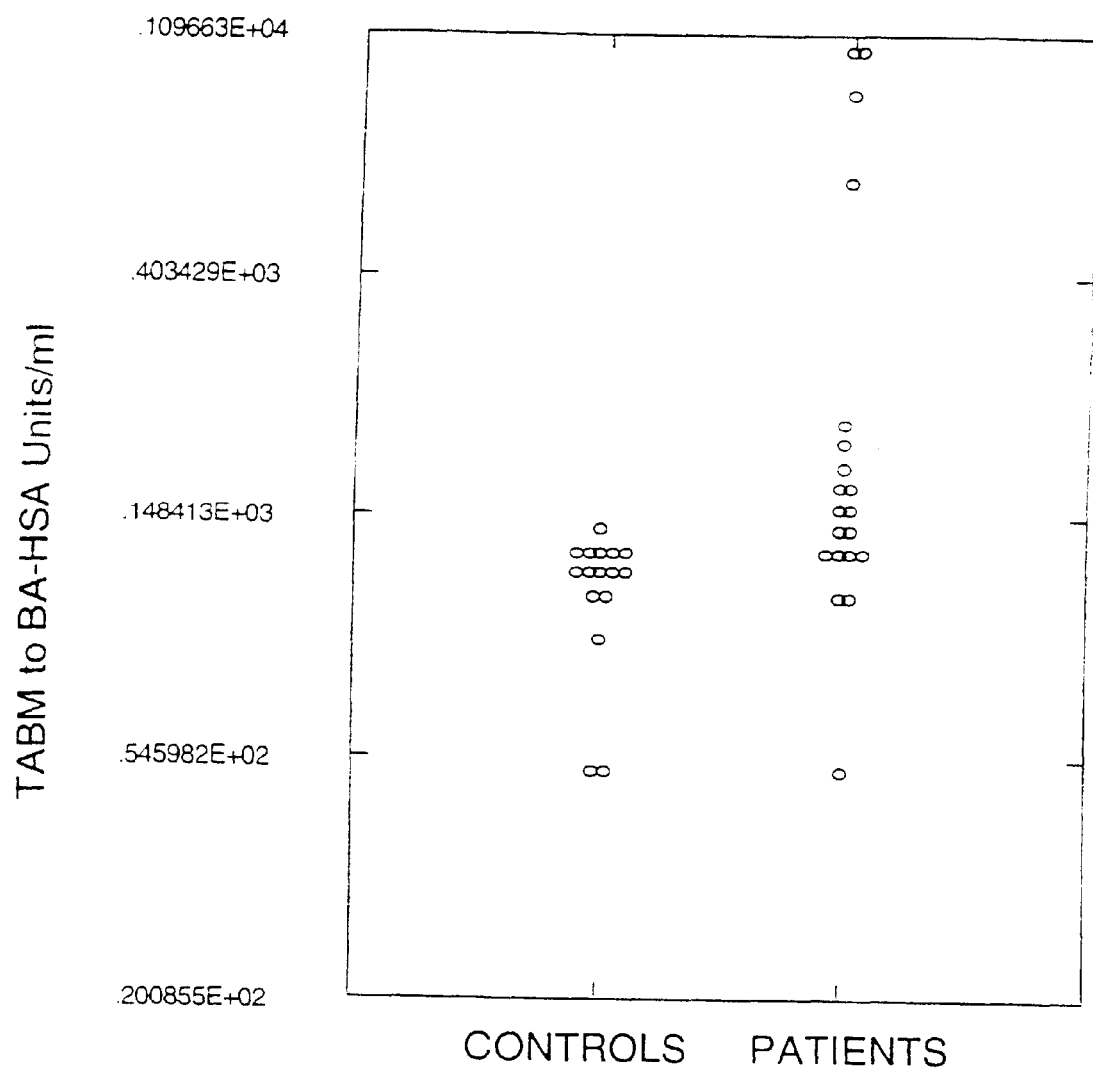

FIG. 21 is a graphical representation of serum levels of antigen specific TABM to BA-HSA, P=0.002.

Figure 22:
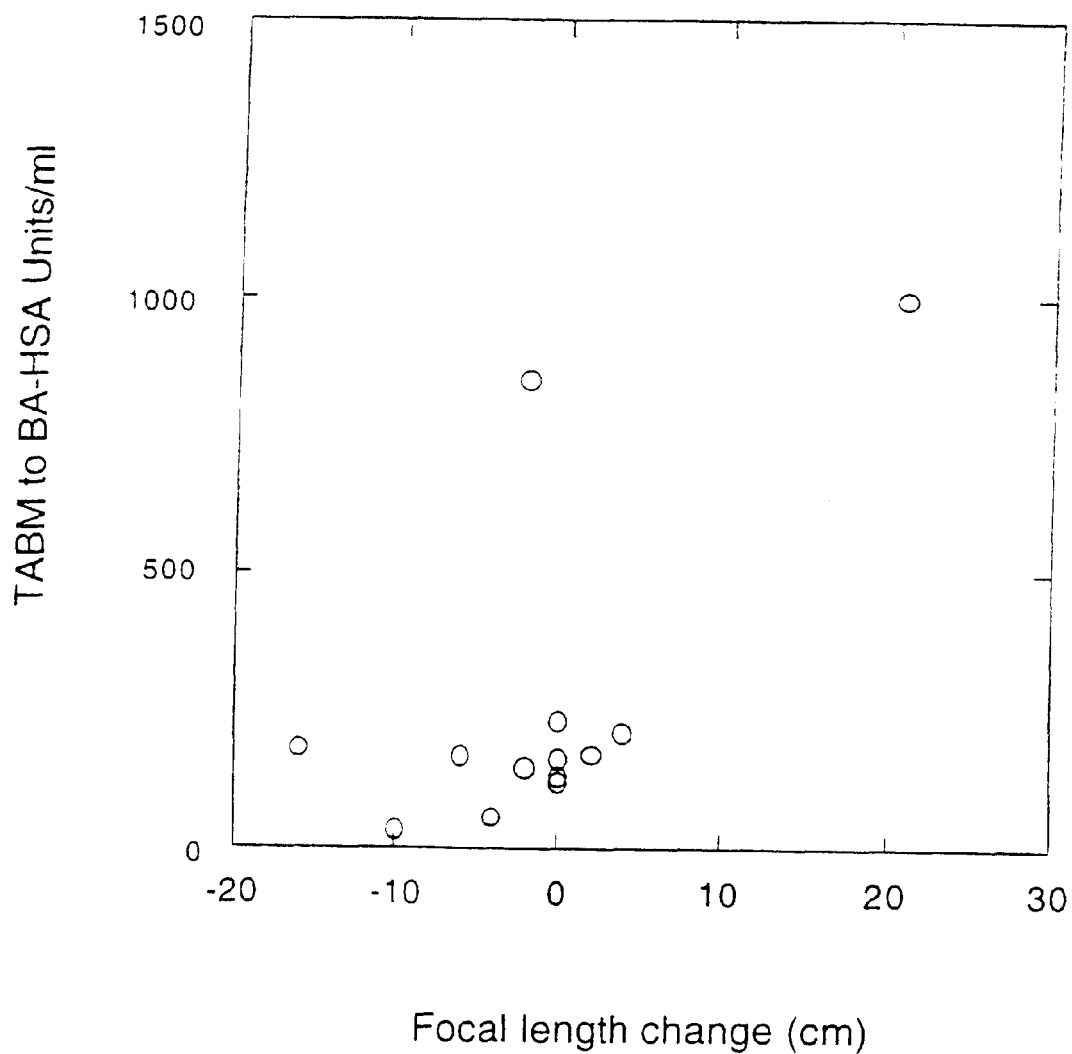

FIG. 22 is a graphical representation of TABM levels to BA-HSA versus change in focal length in patients.

Figure 23:
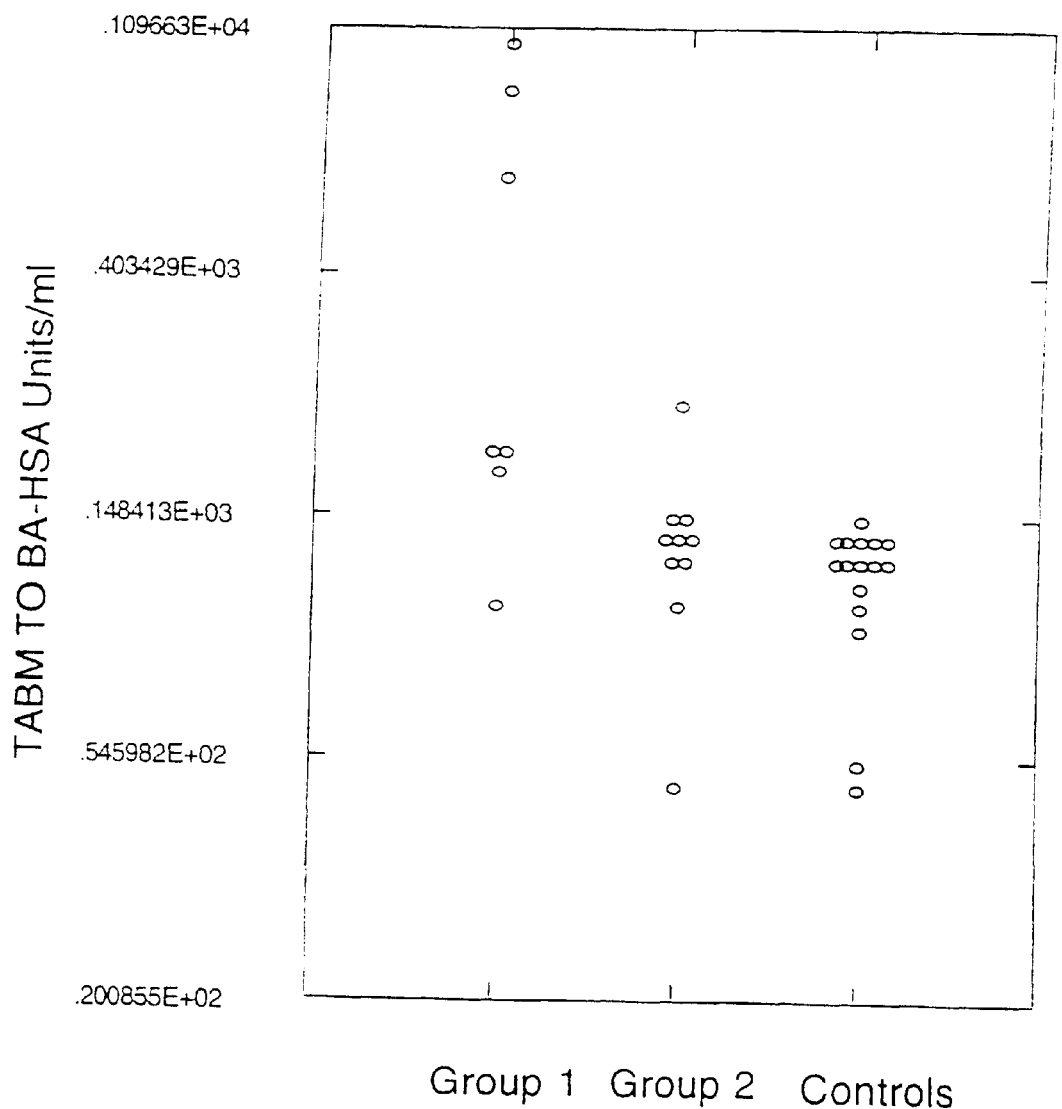

FIG. 23 is a graphical representation of antigen specific TABM to BA-HSA in patients and controls. Group 1:14–25 years. Group 2:up to 13 years duration of chemical exposure.

Figure 24:
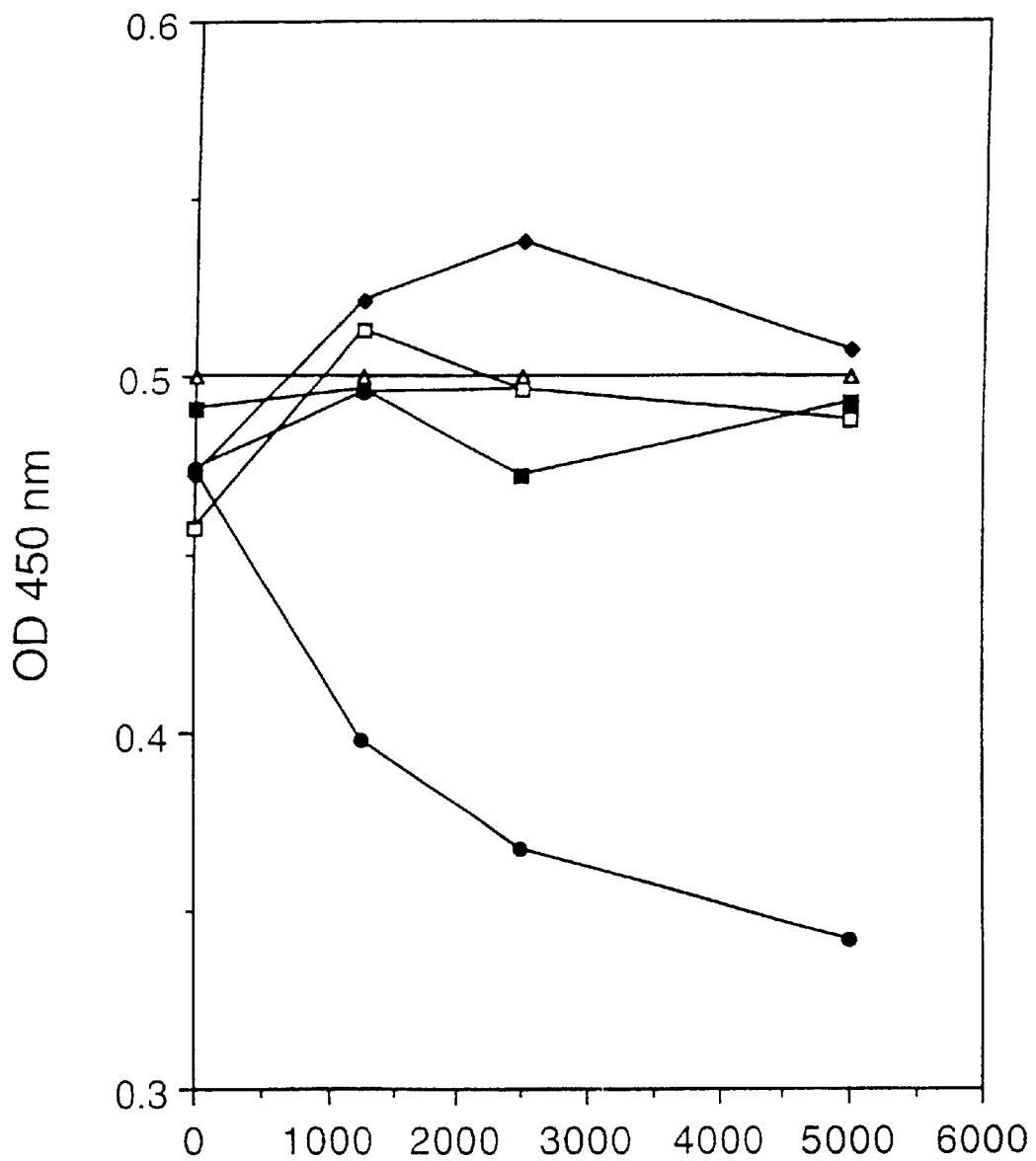

FIG. 24 is a graphical representation showing that increasing levels of free BA-HSA bind to serum TABM and inhibit the specific binding to plate bound BA-HSA.

Figure 25A:
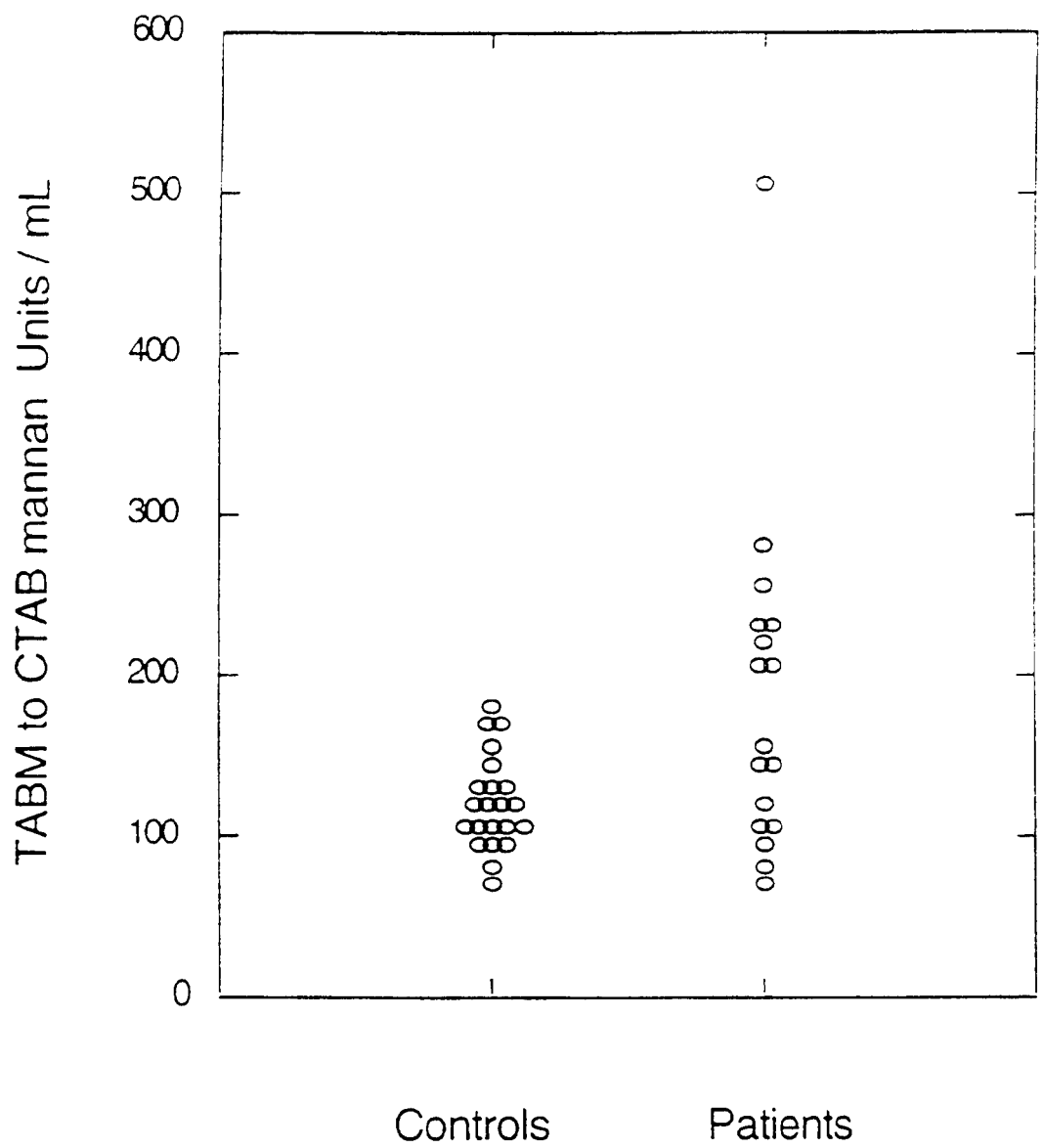
Figure 25B:
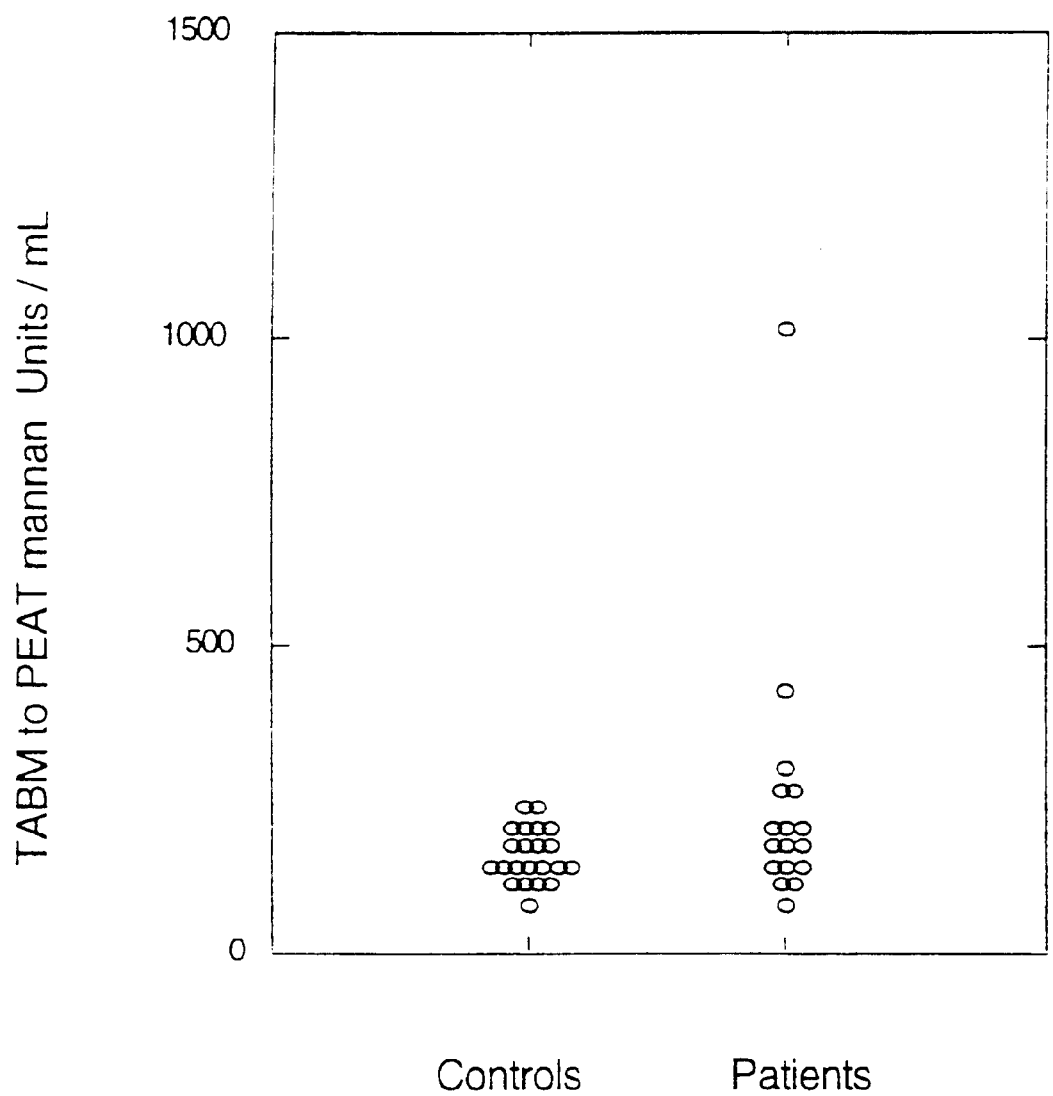
Figure 25C:
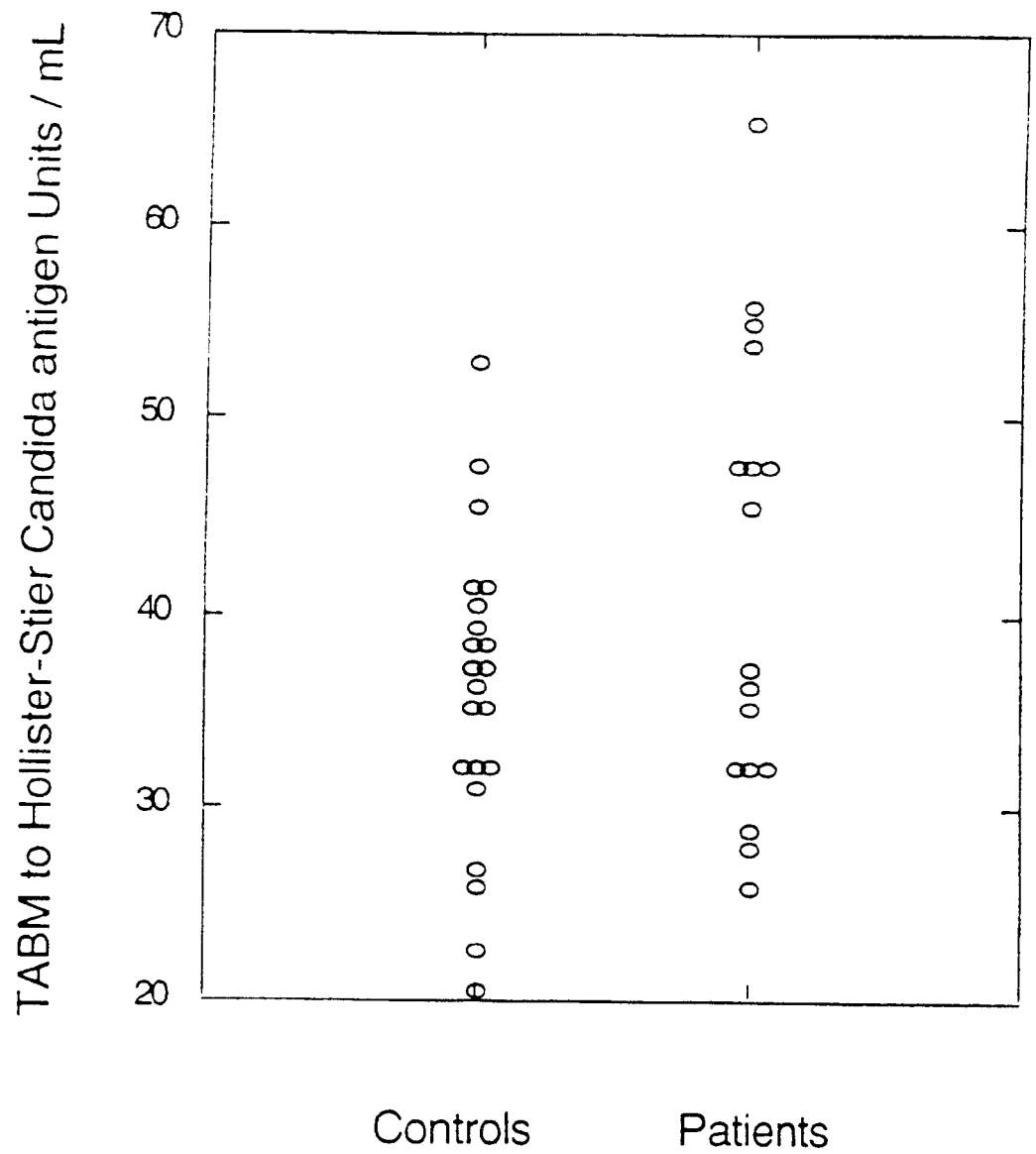

—▲— Serum 1/200
—●— Serum 1/200 + HSA
—○— Serum 1/200 + BSA
—●— Serum 1/200 + BA•HSA
—□— Serum 1/200 + TNP•HSA
—■— Serum 1/200 + F•HSA FIGS. 25A–25C are a graphical representation of the levels of antigen specific TABM to *Candida albicans* CTAB (A) and PEAT (B) mannans and to the Hollister-Stier skin test preparation (C) was determined in a control and a patient group. P values are 0.0291, 0.0721 and 0.2166, respectively.

Figure 26A:
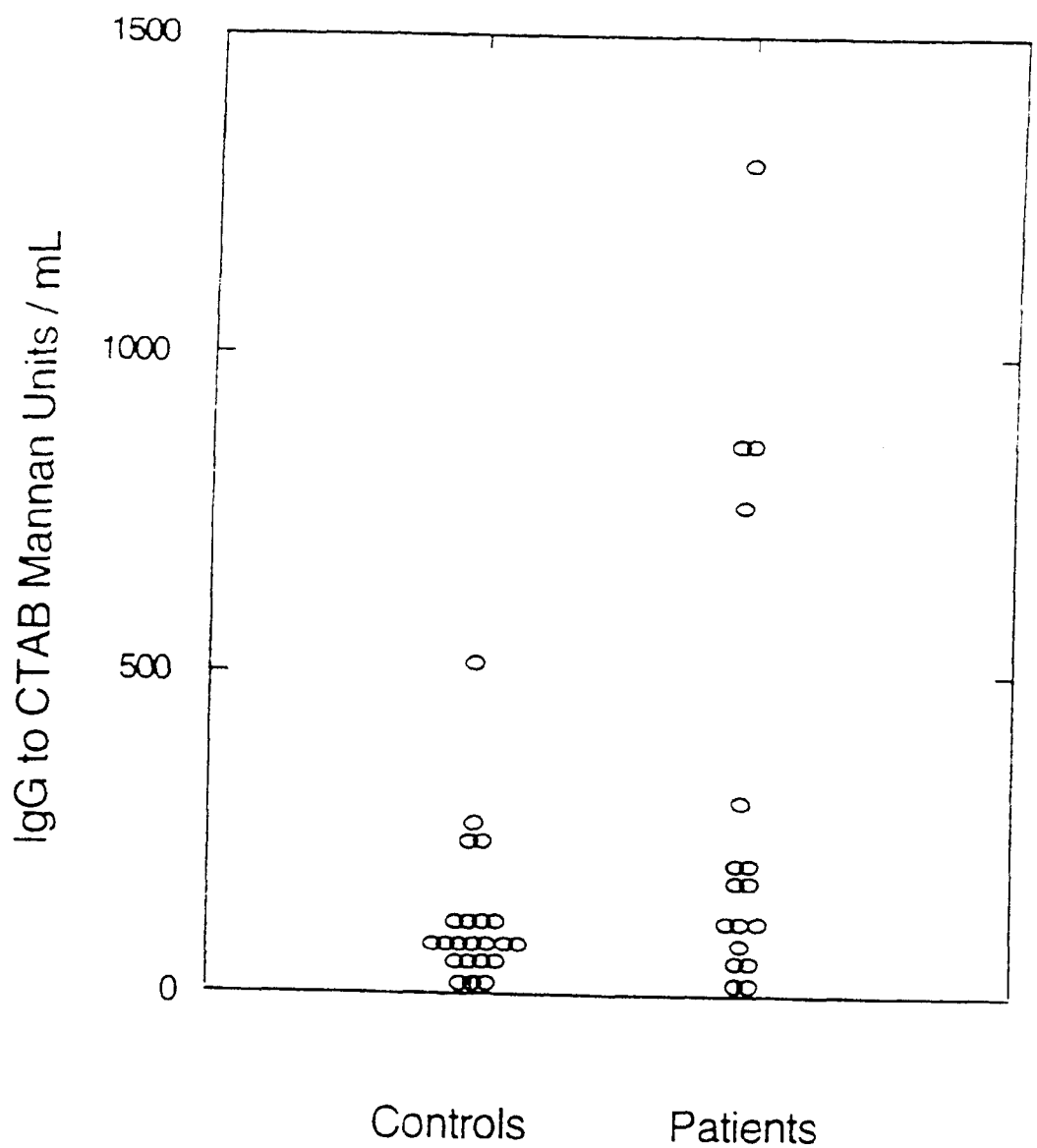
Figure 26B:
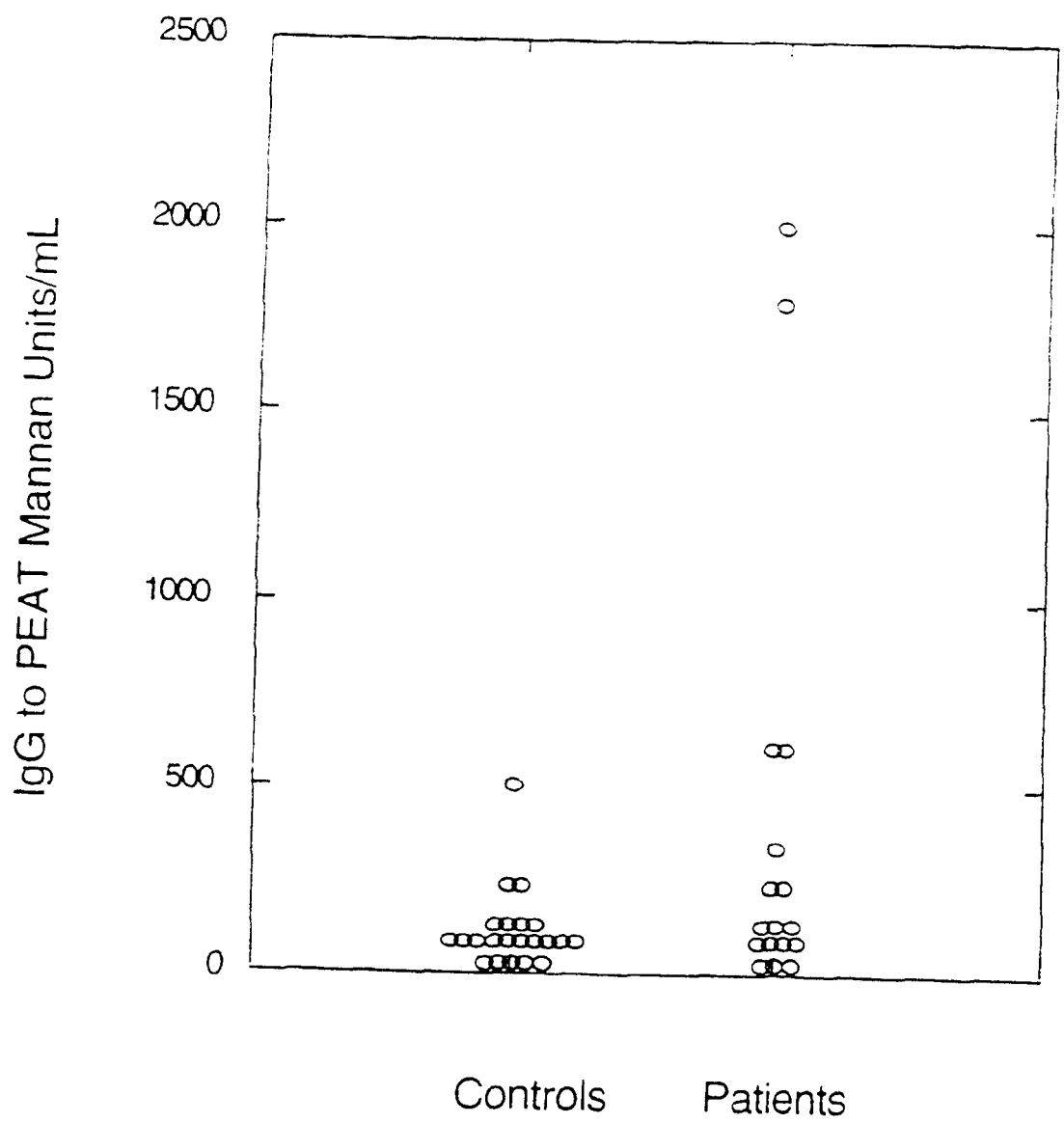
Figure 26C:
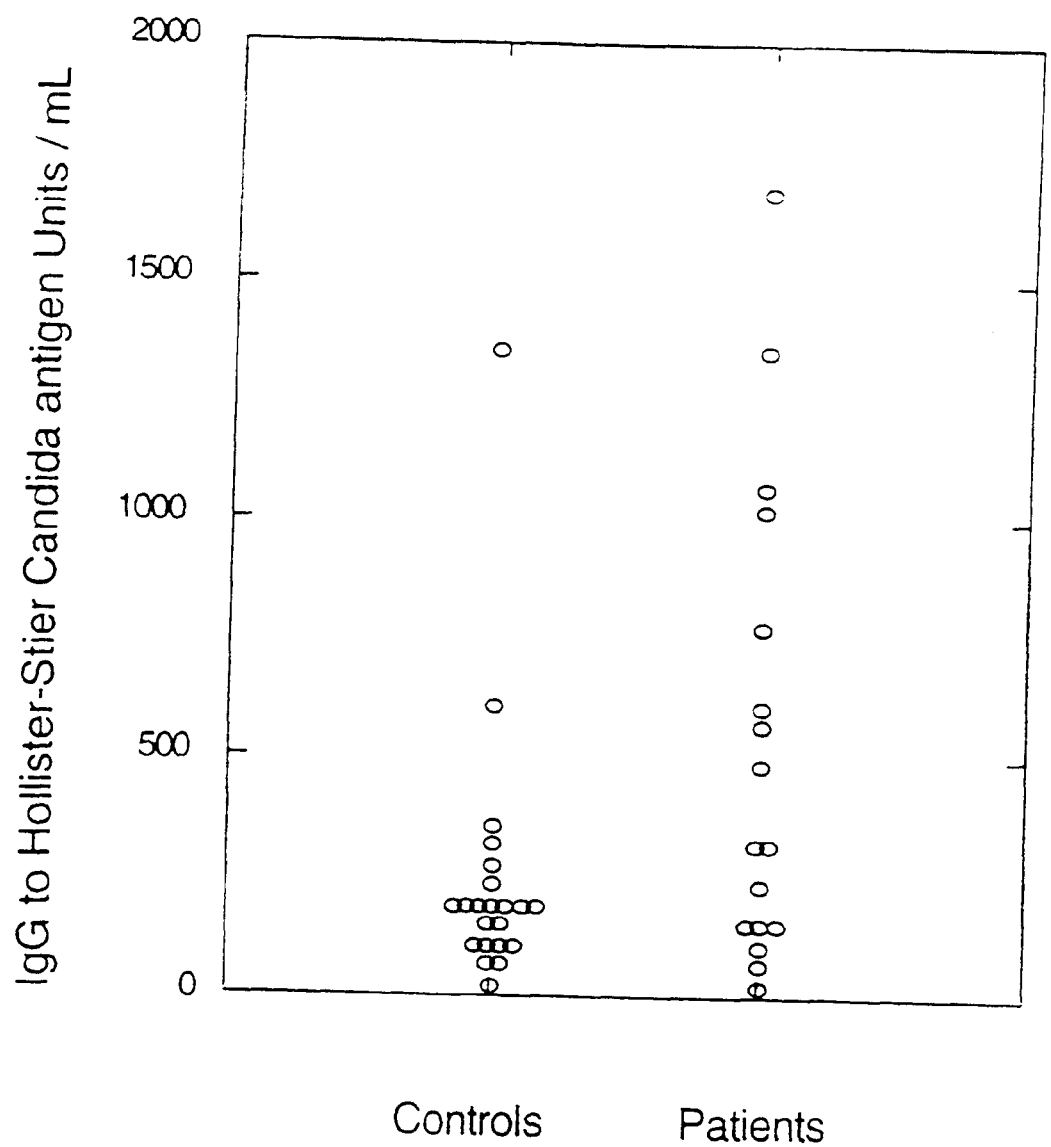

FIGS. 26A–26C are a graphical representation of the levels of antigen specific IgG to *Candida albicans* CTAB (A) and PEAT (B) mannans and to the Hollister-Stier skin test preparation. (C) was determined in a control and a patient group. P values are 0.0458, 0.0303 and 0.0791 respectively.

Figure 27A:
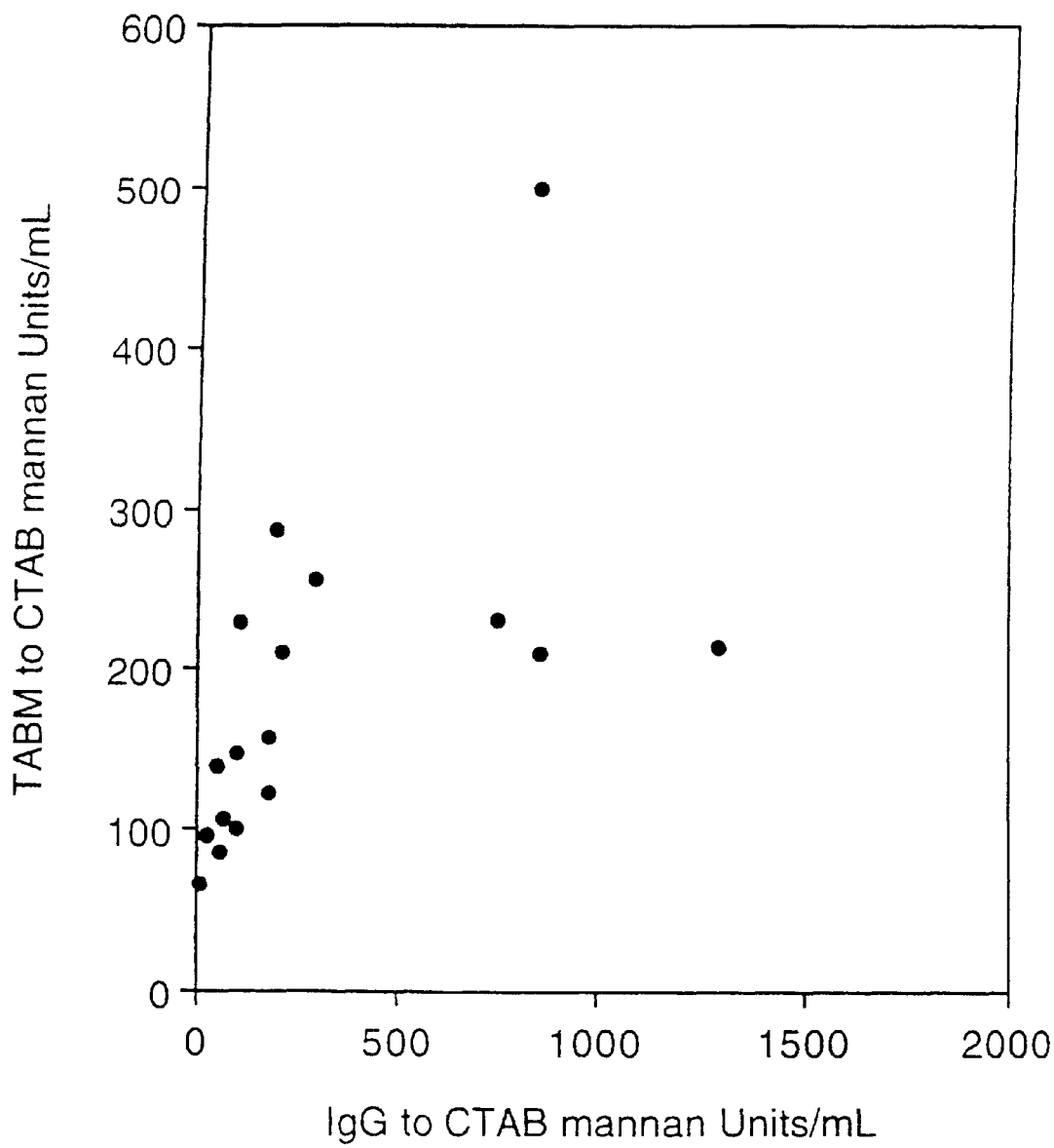
Figure 27B:
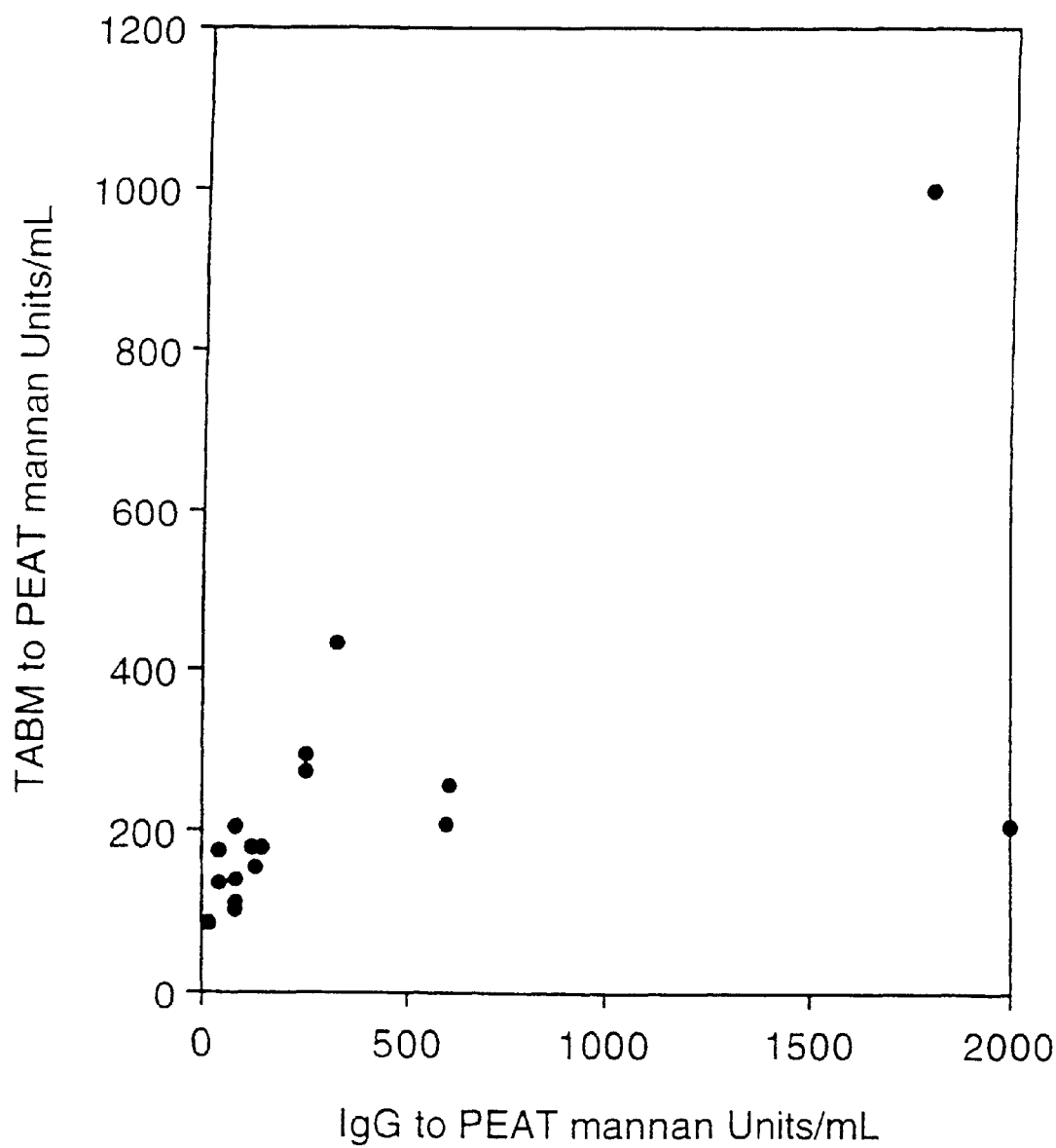
Figure 27C:
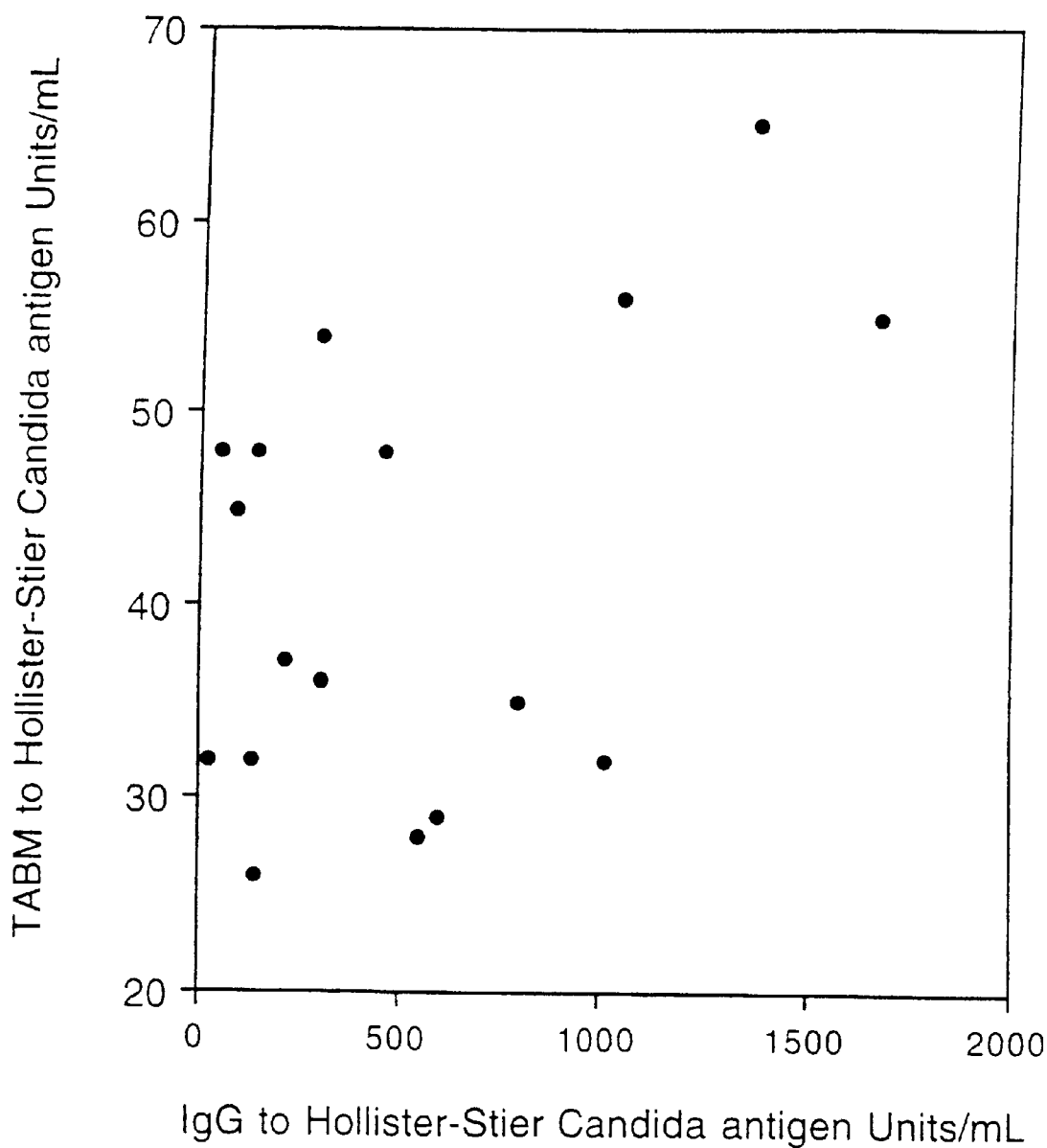

FIG. 27 is a graphical representation of the levels of TABM were plotted against the levels of IgG for CTAB, PEAT and Hollister-Stier *Candida* antigens.

Figure 28A:
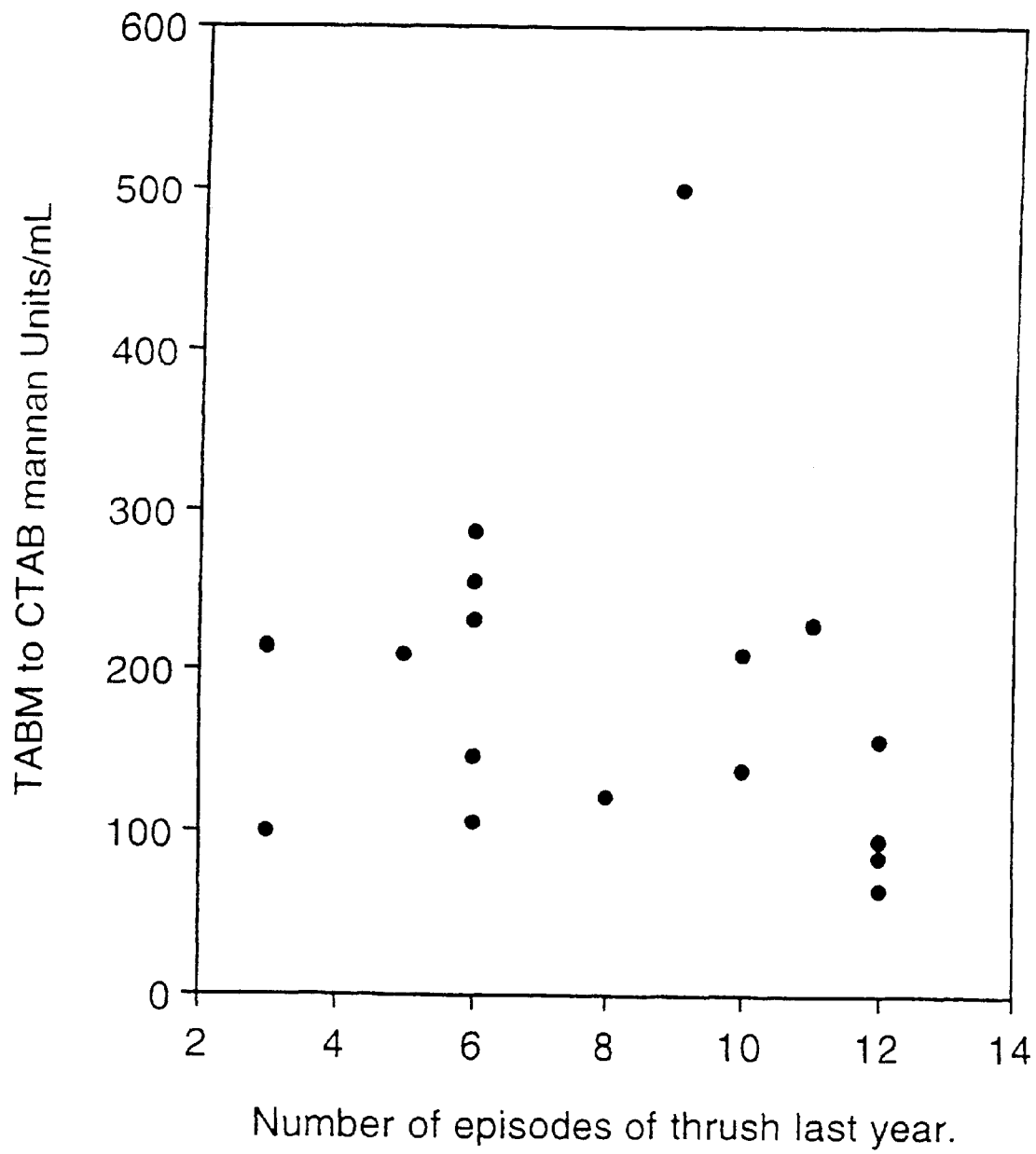
Figure 28B:
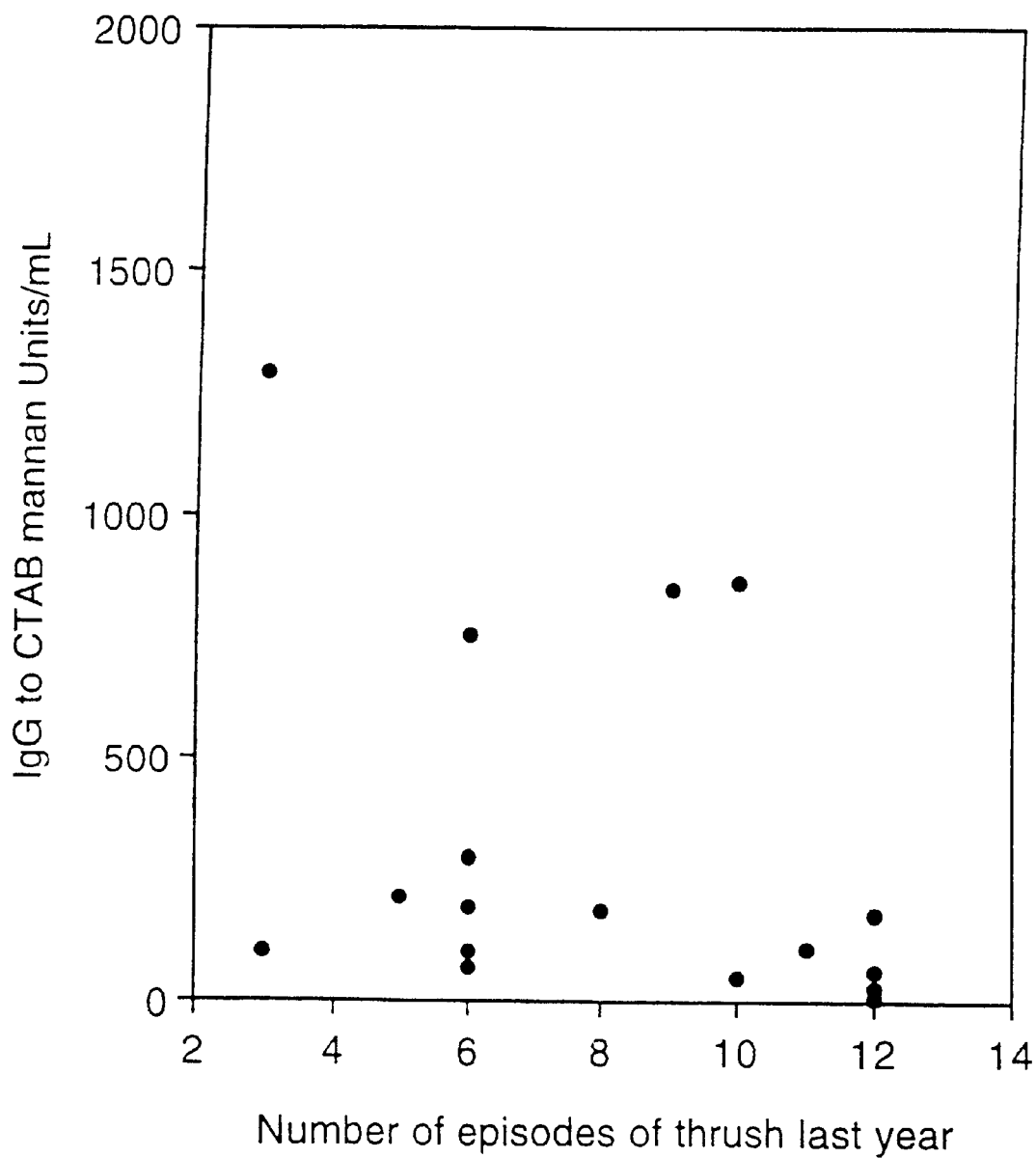

FIGS. 28A–28B are a graphical representation of the levels of antigen specific TABM (A) and IgG (B) to CTAB mannan are plotted against the number of episodes of thrush experienced within twelve months in the patient group.

Figure 29A:
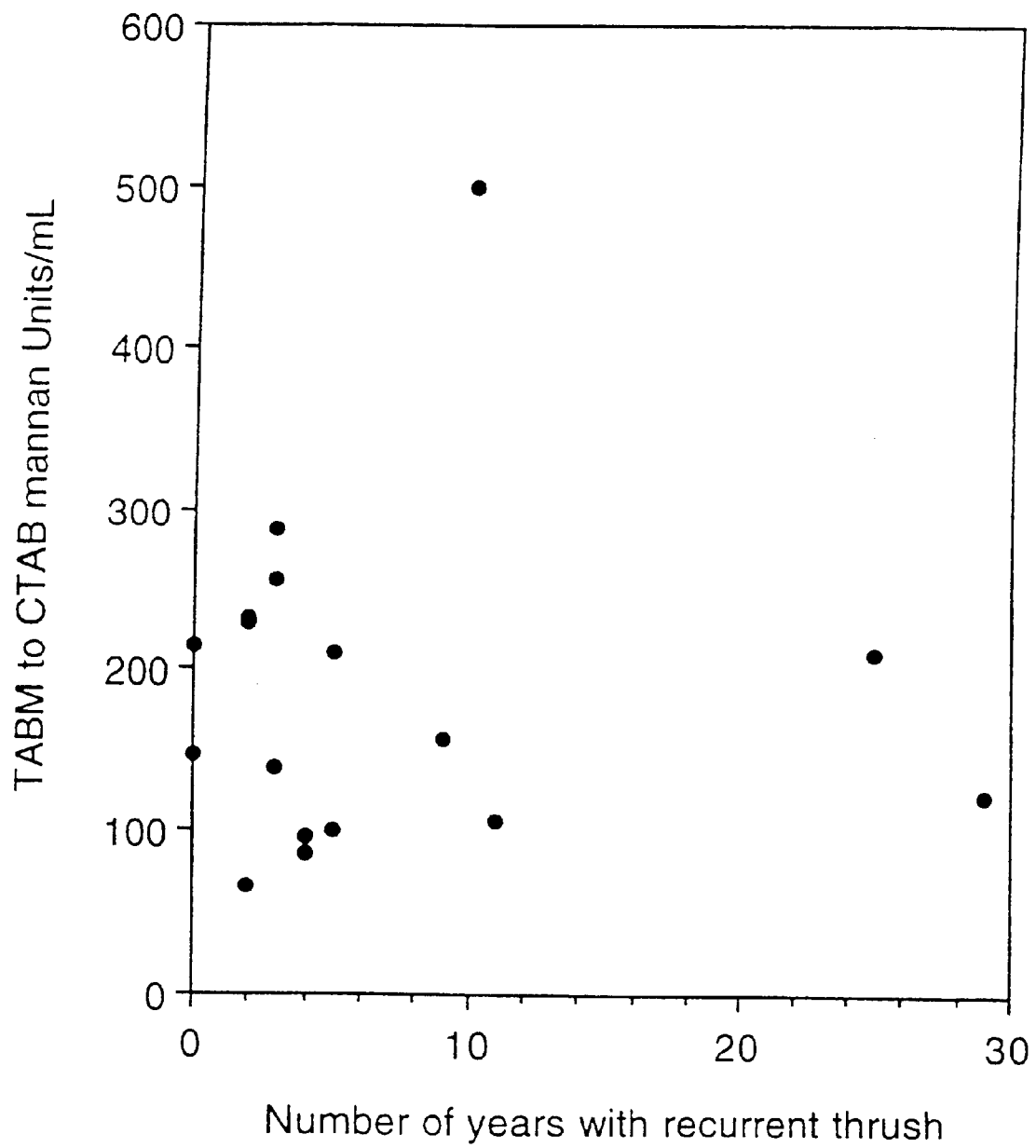
Figure 29B:
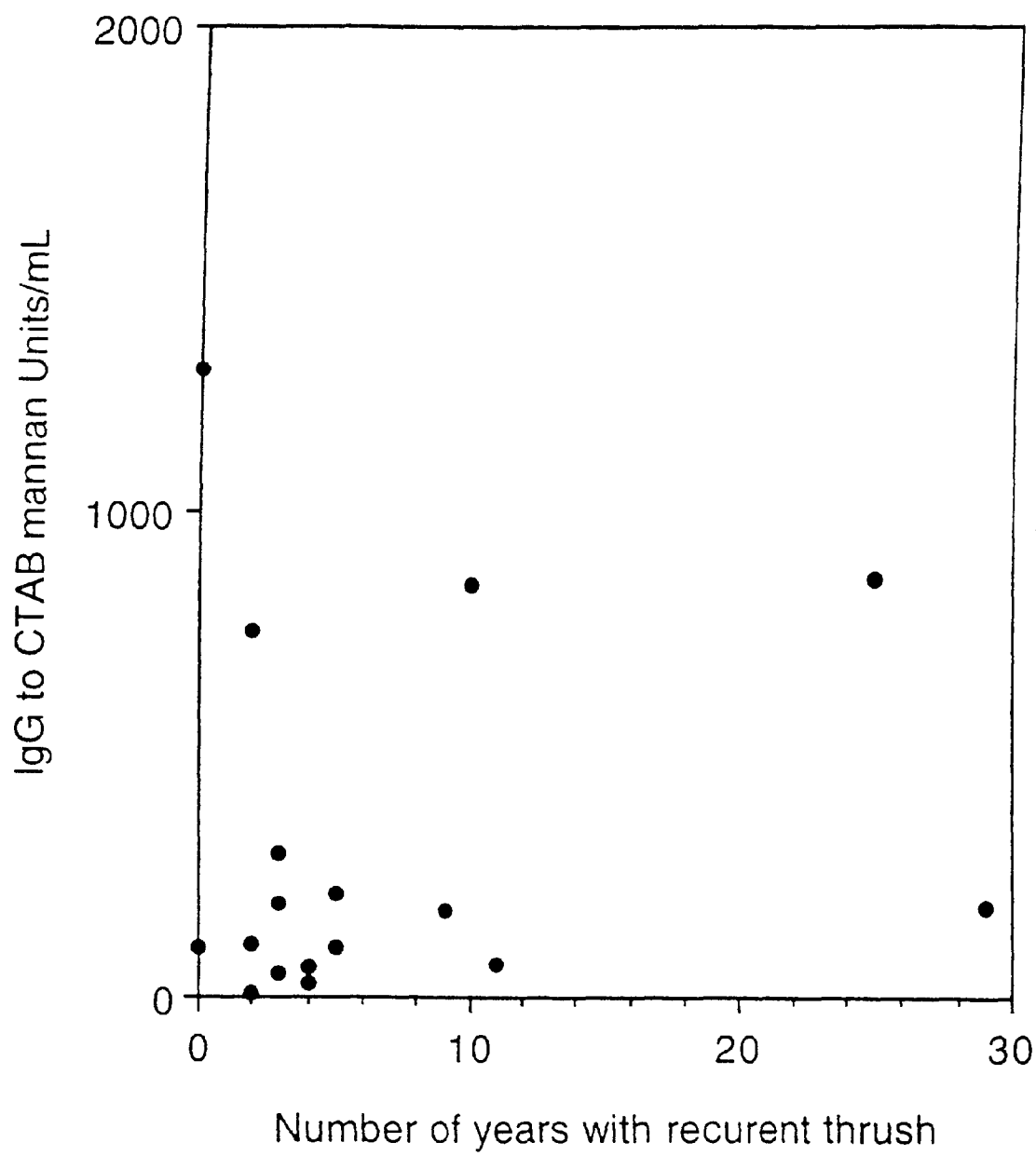

FIGS. 29A–29B are a graphical representation of the levels of antigen specific TABM (A) and IgG (B) to CTAB mannan are plotted against the number of years with recurrent thrush in the patient group.

Figure 30A:
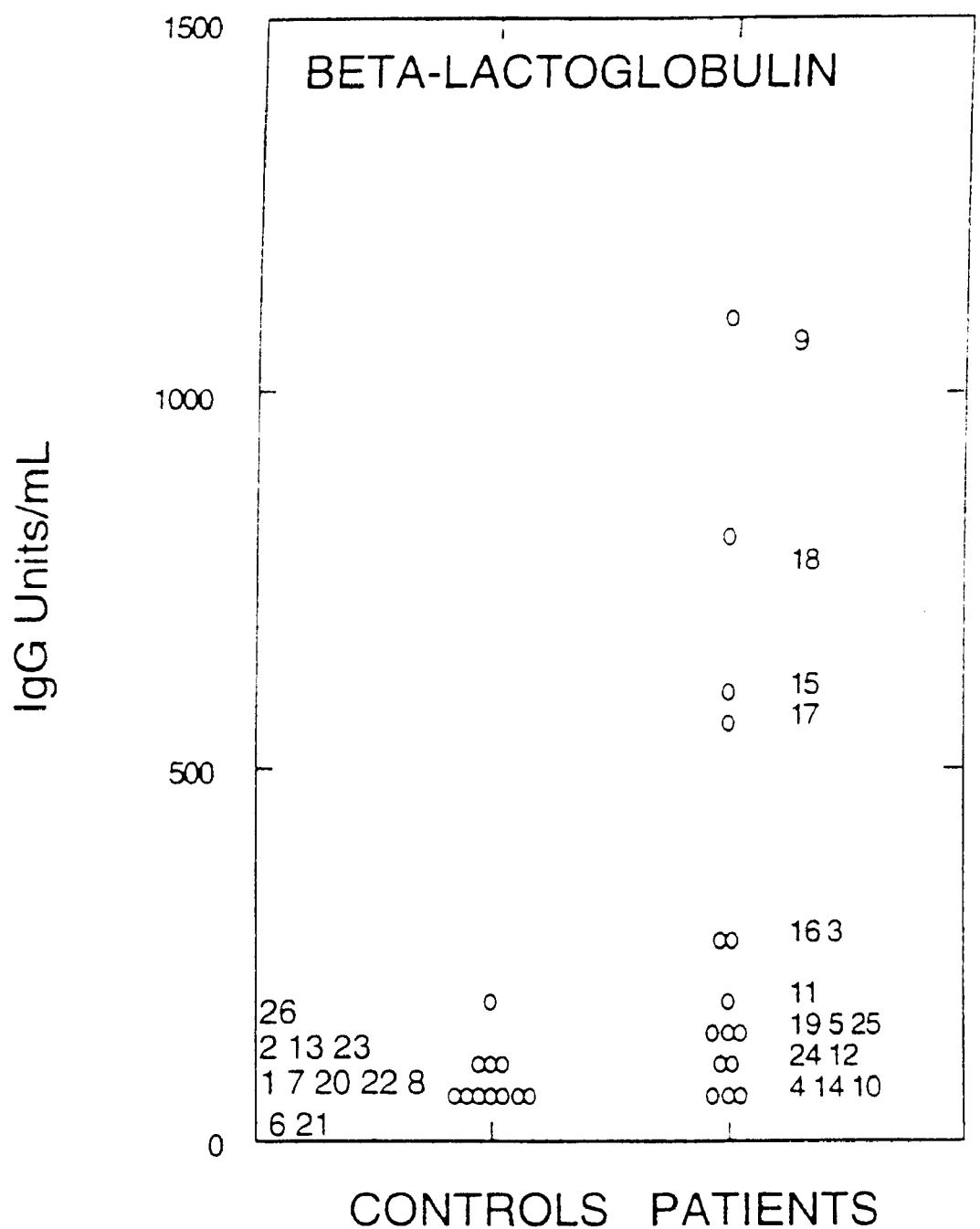
Figure 30B:
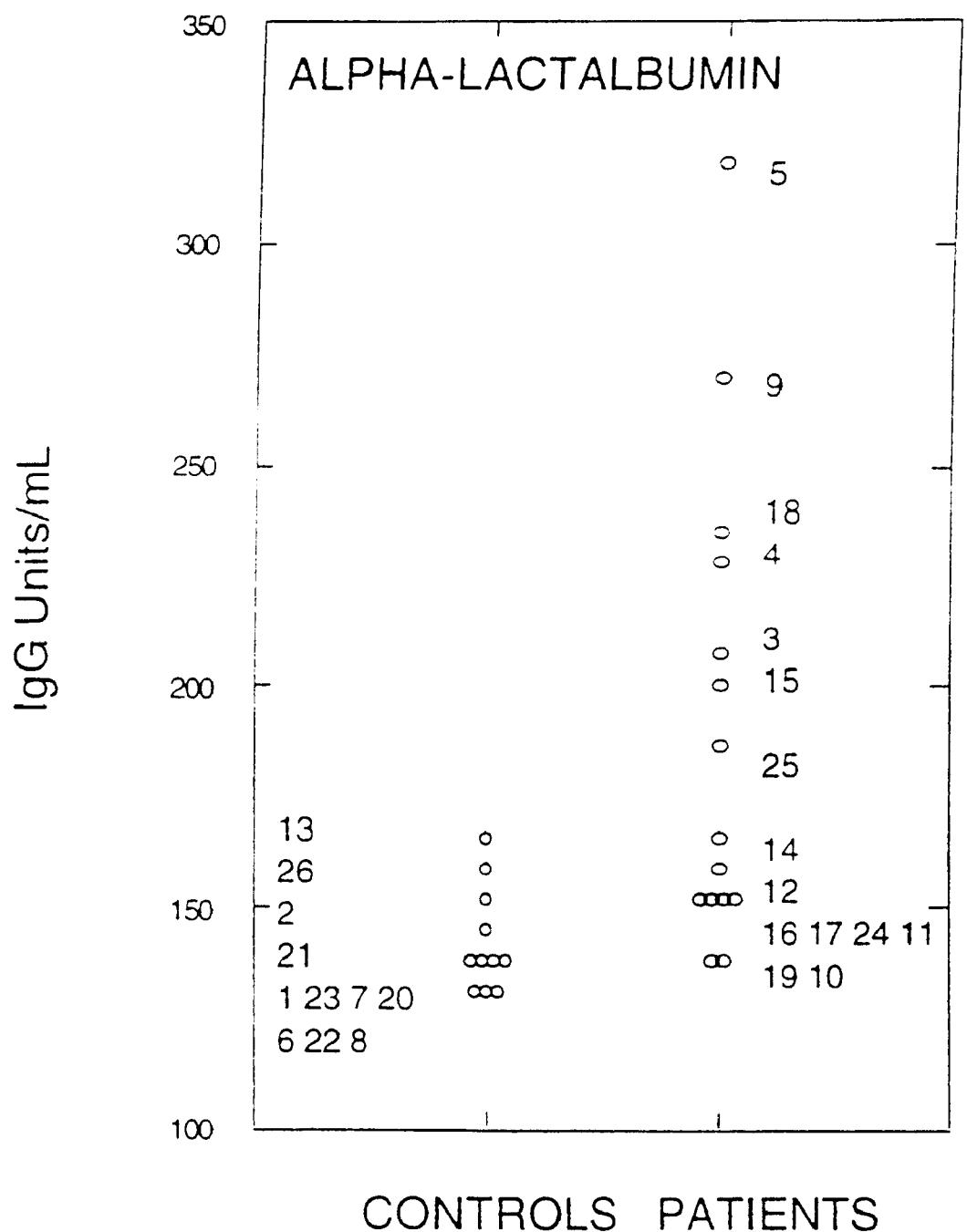
Figure 30C:
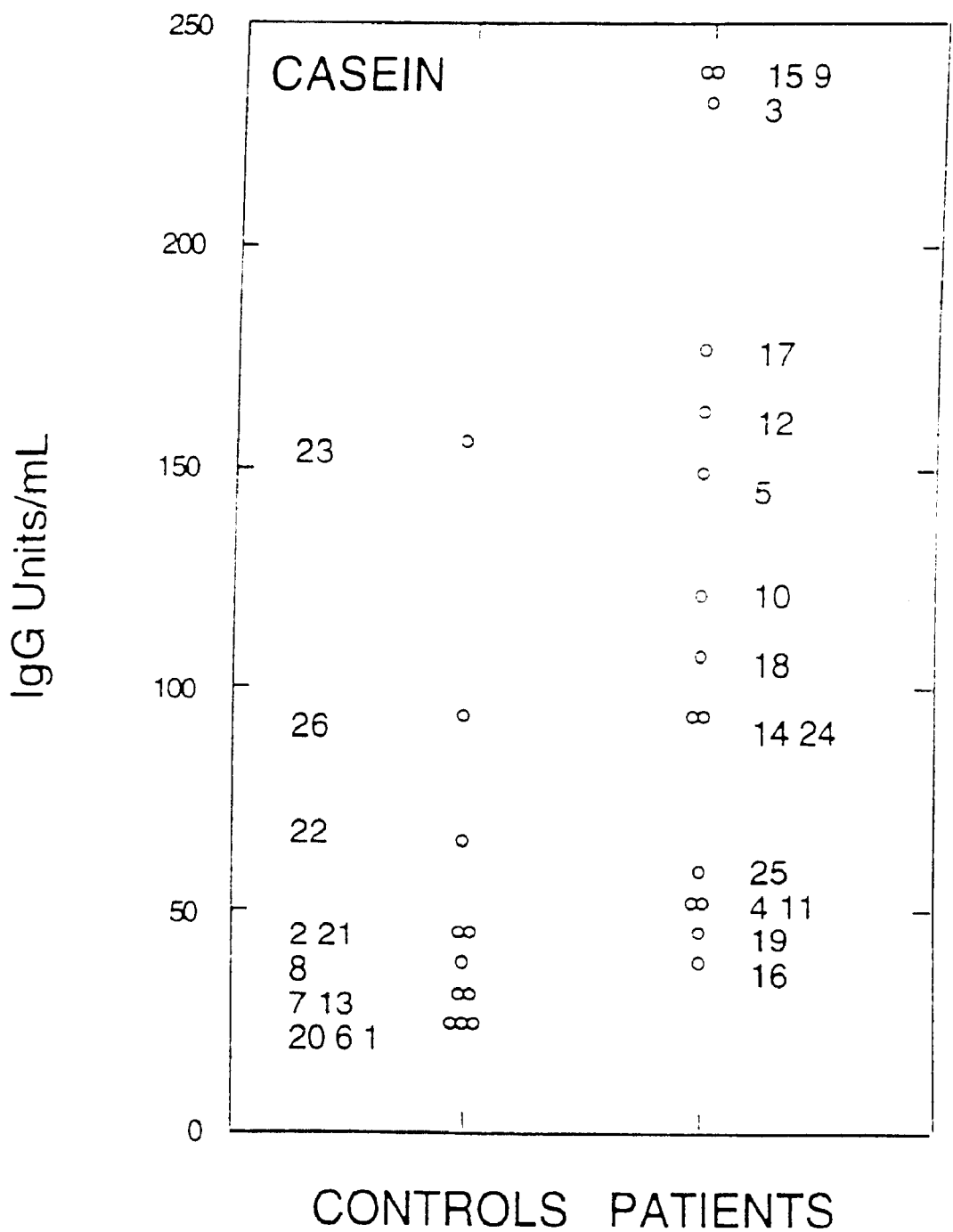

FIGS. 30A–30C are a graphical representation showing serum levels of antigen-specific IgG to β-lactoglobulin (BLG), α-lactalbumin (AL) and α-s-casein (CA). Group 1=controls, Group 2=patients.

Figure 31:
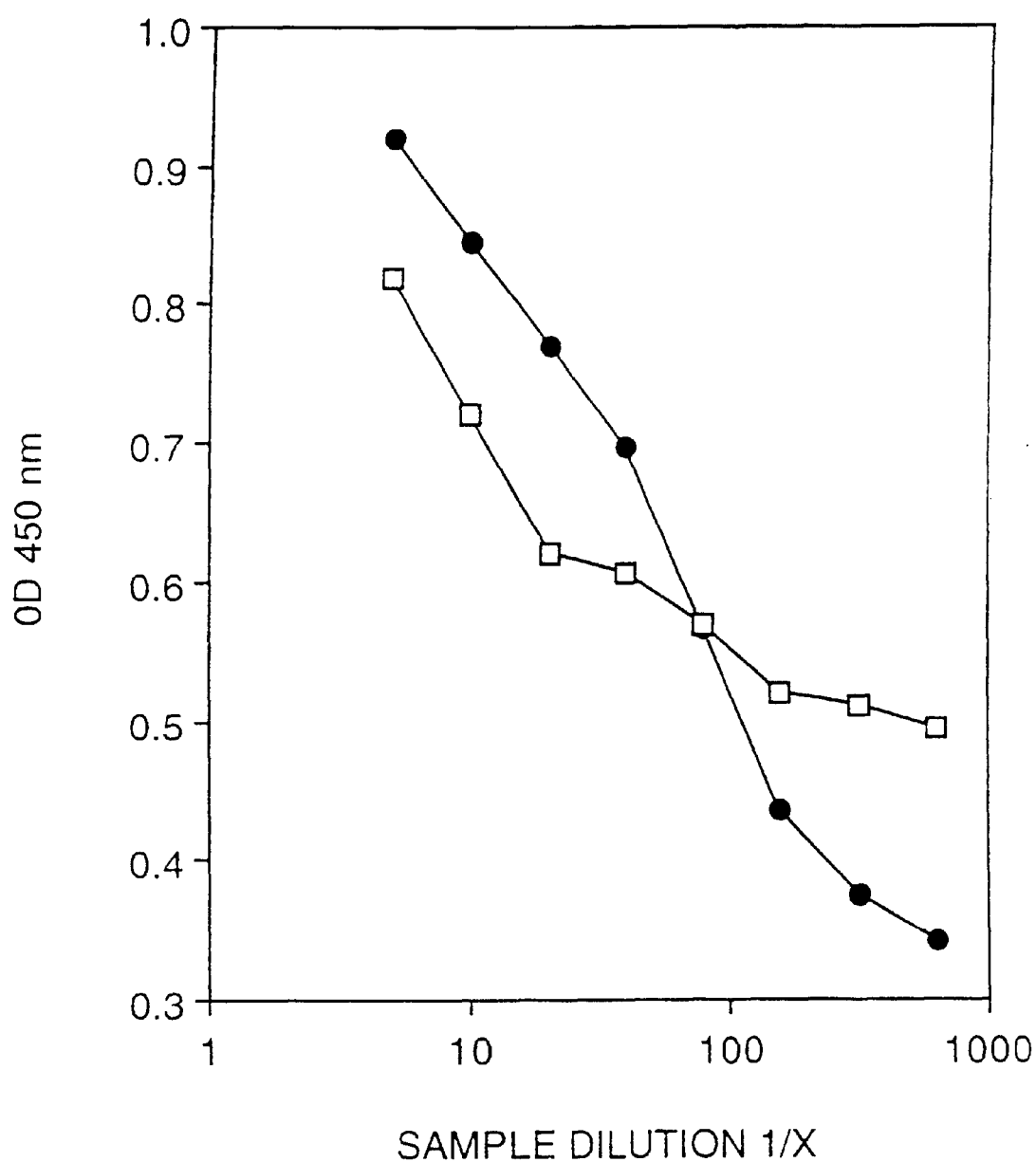

FIG. 31 is a graphical representation showing titration for β-lactoglobulin-specific TABM. Dilutions of serum from a milk-intolerant patient and purified BL-TABM were added to microtiter wells coated with 1 μg/well β-lactoglobulin. After incubation and washing, rabbit anti-human TABM (1:300) was added, and bound antibodies detected with peroxidase-conjugated sheep anti-rabbit IgG.

—●— Serum
—□— BL + TABM

Figure 32A:
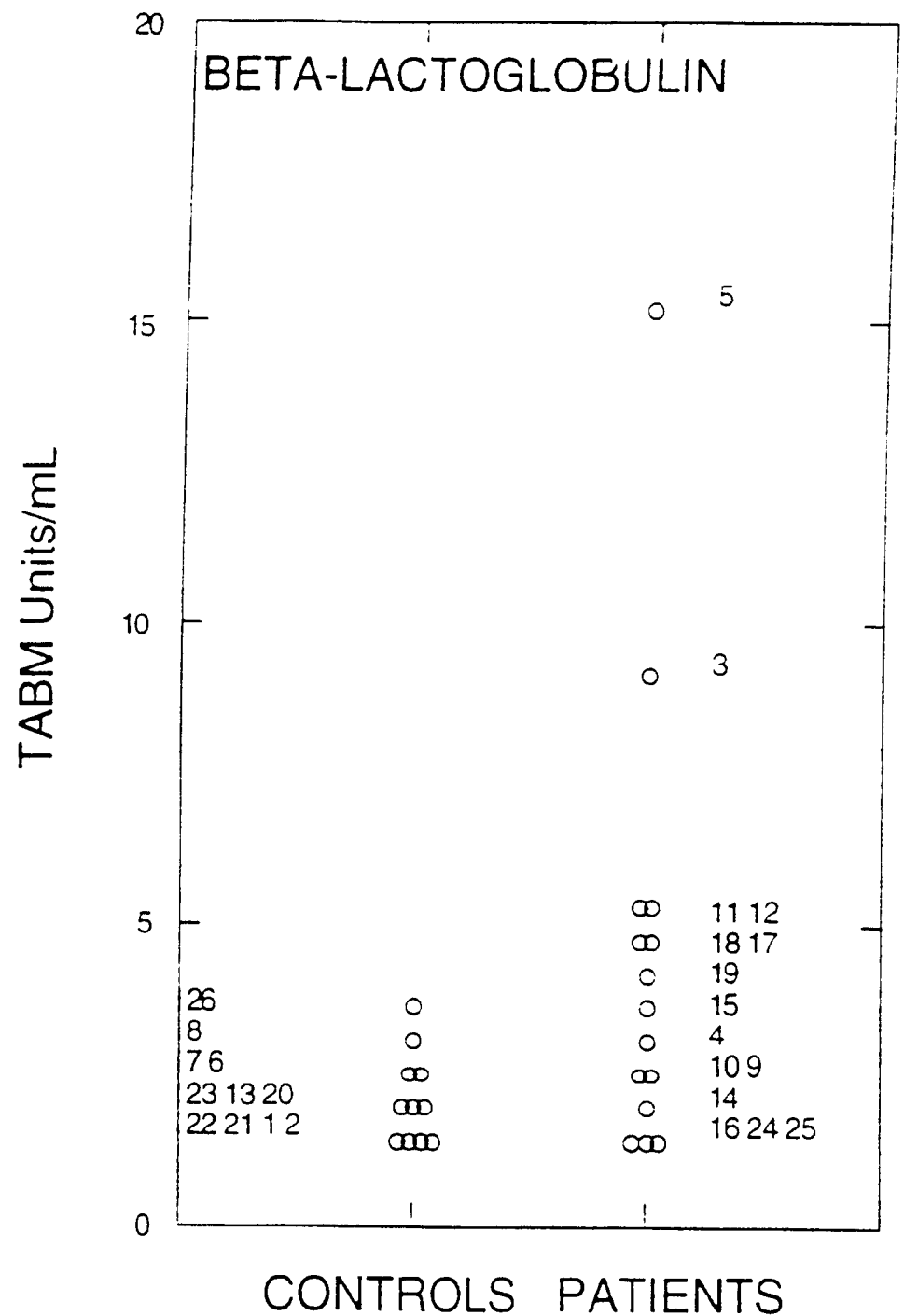
Figure 32B:
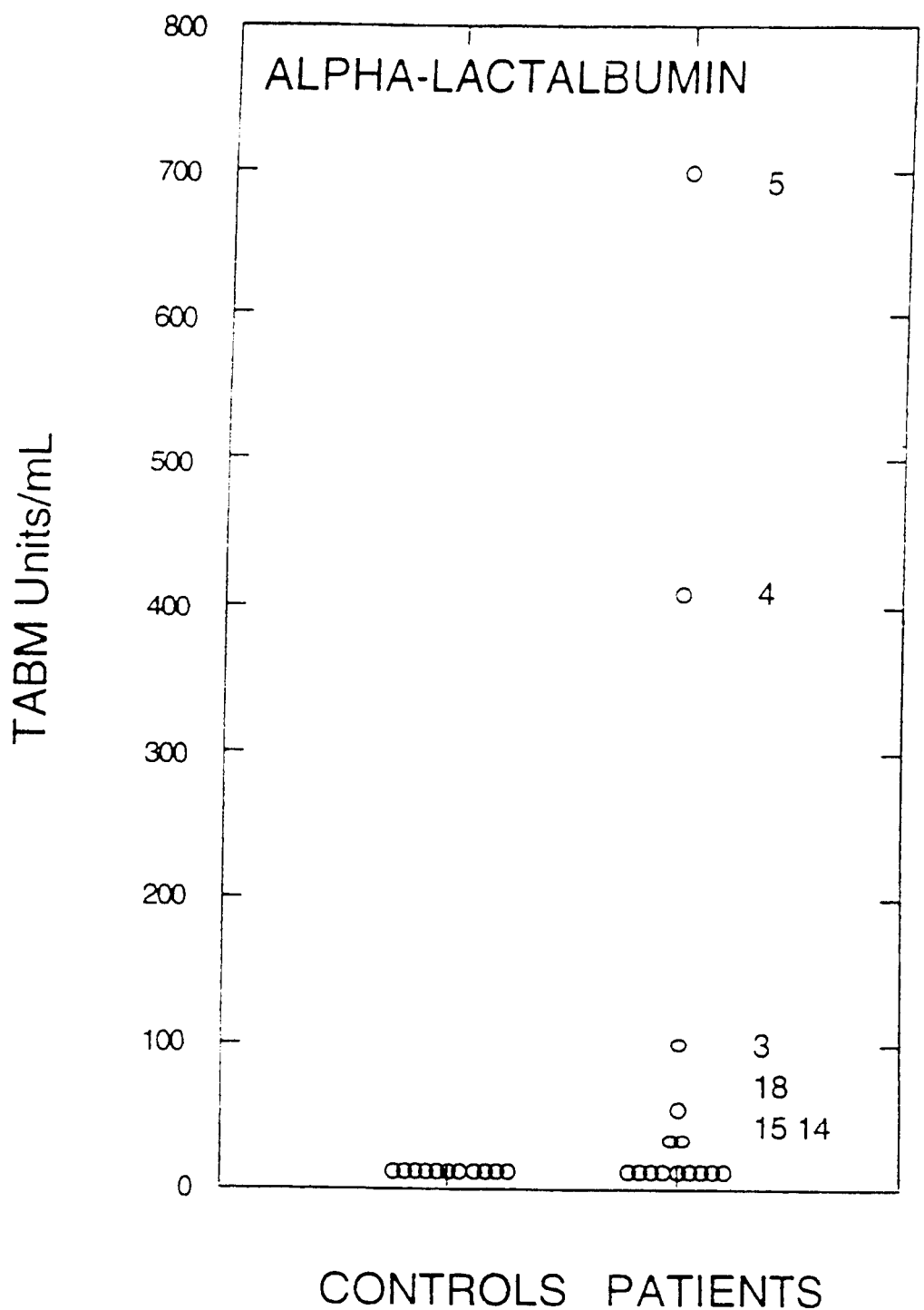
Figure 32C:
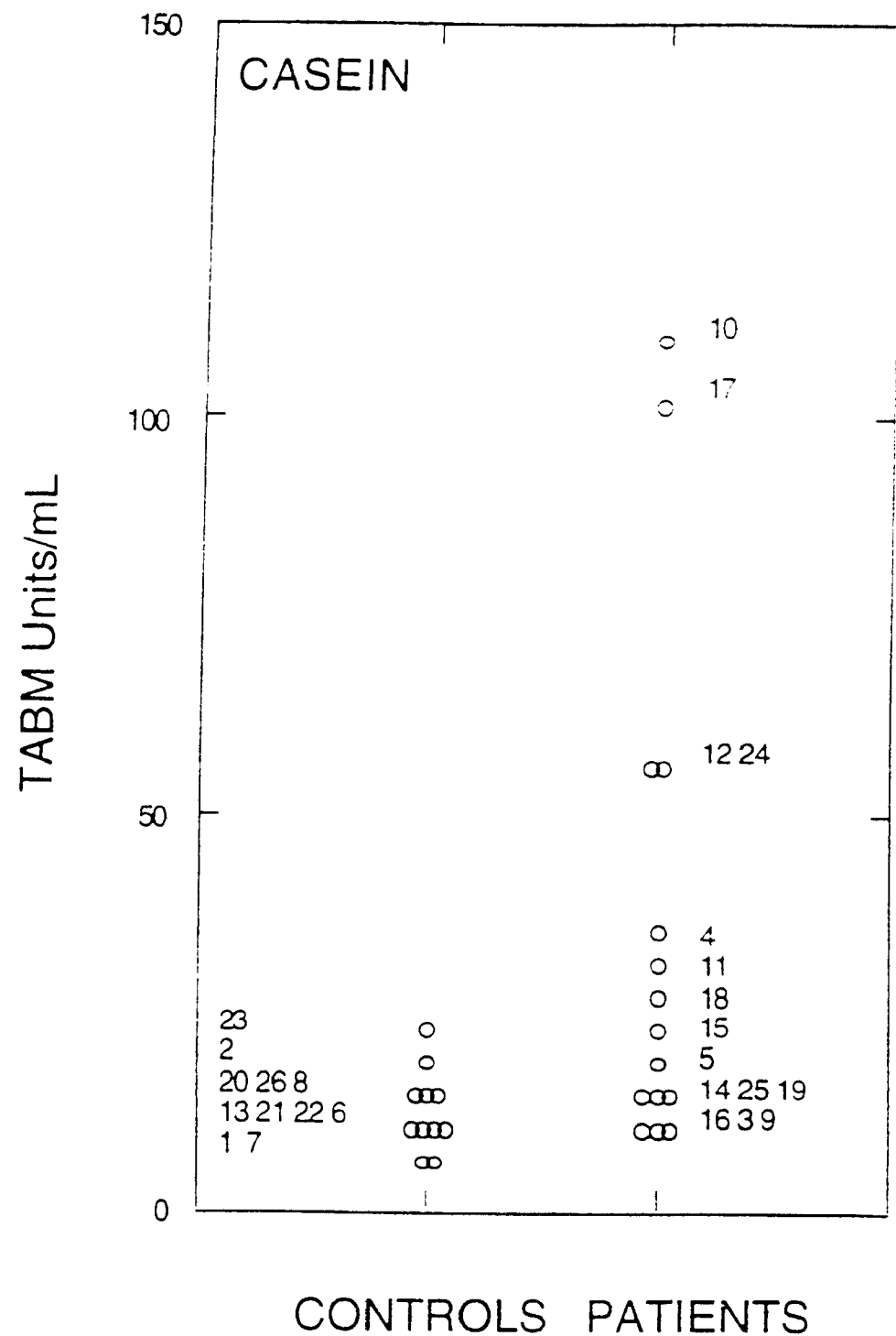

FIGS. 32A–32C are a graphical representation showing serum levels of antigen-specific TABM to (A)BLG, (B)AL, and (C)CA. Sera were diluted 1:4 and 100 μl tested against 500 ng of antigen and detected as in FIG. 31.

Group 1=controls, Group 2=patients.

Figure 33:
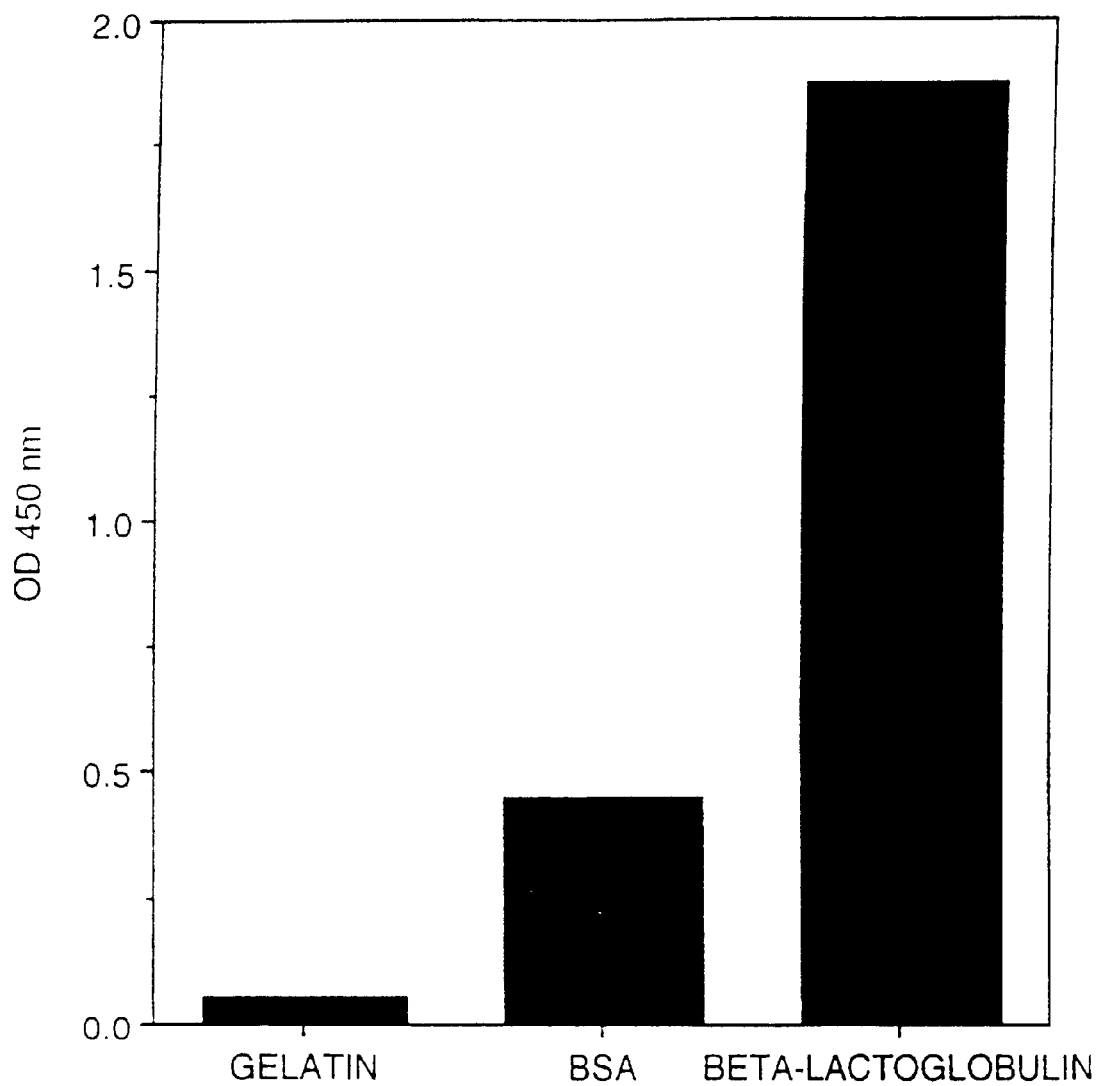

FIG. 33 is a graphical representation of purified BL-TABM tested for binding to gelatin, bovine serum albumin (BSA) and BLG. Serum from a milk-intolerant patient was absorbed with β-lactoglobulin-conjugated sepharose beads, and the beads eluted with NaCO$_3$. The dialyzed eluate was added to microtiter wells coated with 5 μg β-lactoglobulin, BSA or gelatin. Bound protein was detected with rabbit anti-human TABM, and peroxidase-conjugated sheep anti-rabbit IgG.

Figure 34:
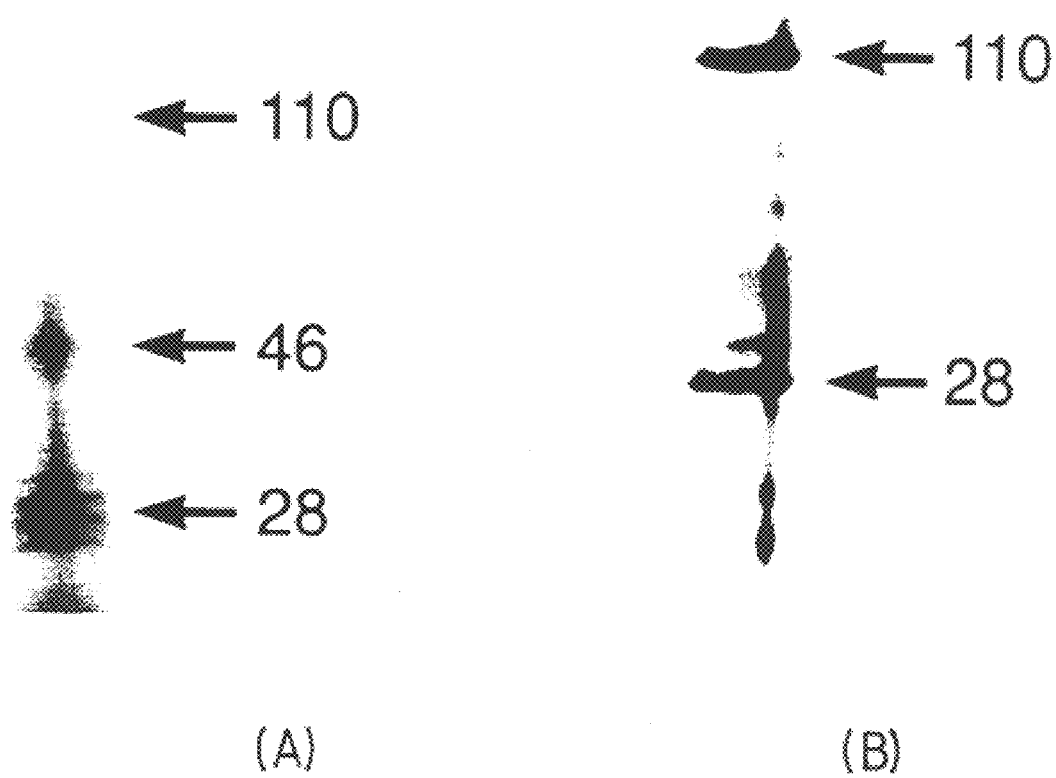

FIG. 34 is a photographic representation depicting resolution of β-lactoglobulin specific TABM by SDS-PAGE. Eight hundred and seventy ng reduced or non-reduced BL-TABM were resolved by SDS-PAGE in a 10–15% w/v gradient. Reduced proteins were visualized by silver stain. Apparent molecular weights were determined by the mobility of molecular weight standards. A) non-reduced; B) reduced.

Figure 35A:
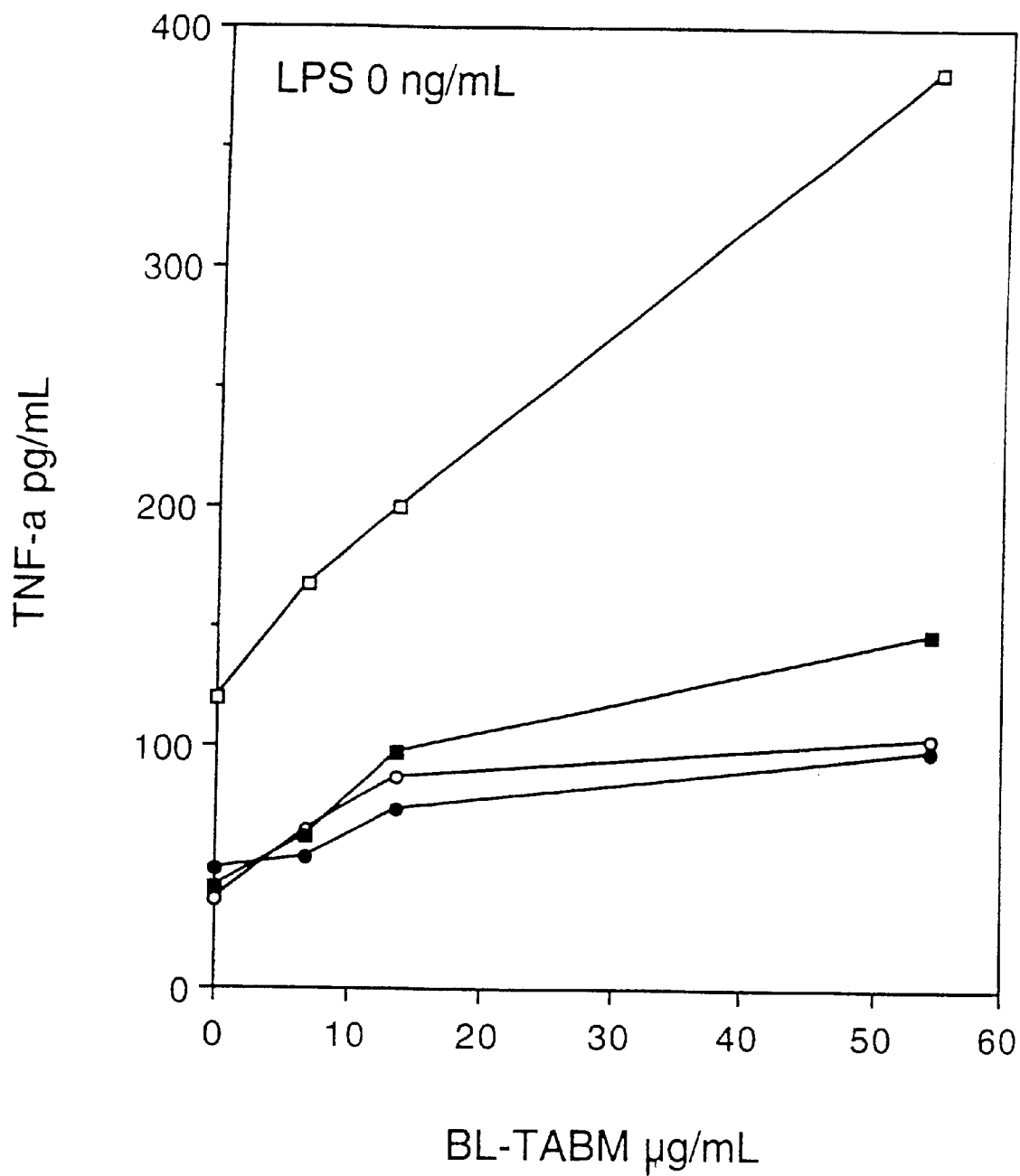

FIG. 35A is a graphical representation showing increasing levels of β-lactoglobulin specific TABM (BL-TABM) induce an increasing amount of TNF-α by normal peripheral blood mononuclear cells. The addition of β-lactoglobulin enhances this effect further.

Figure 35B:
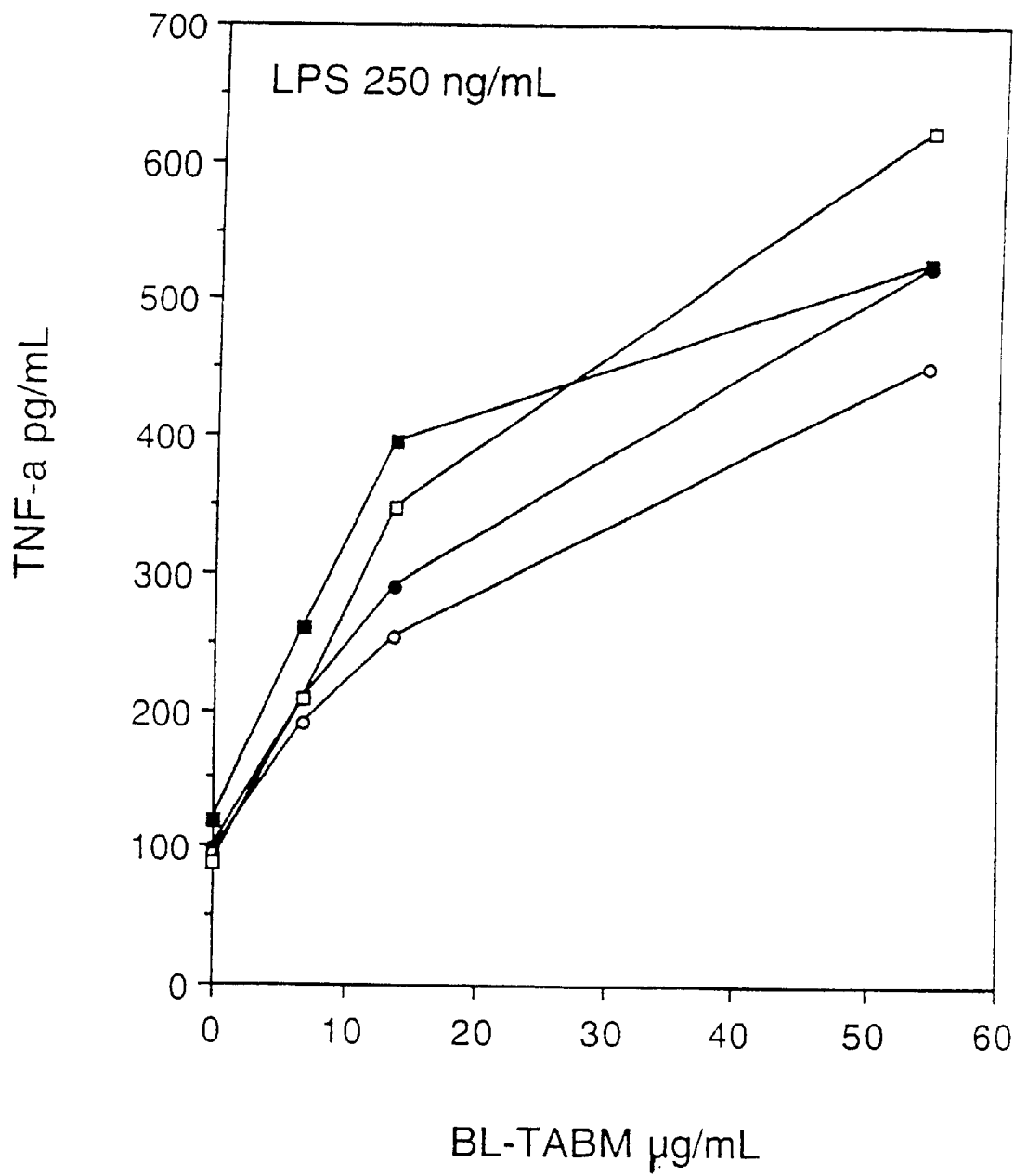

—●— b-Lactoglobulin, 0 ug/ml
—○— b-Lactoglobulin, 0.05 ug/ml
—■— b-Lactoglobulin, 0.5 ug/ml
—□— b-Lactoglobulin, 5.0 ug/ml FIG. 35B is a graphical representation showing that LPS (a strong inducer of TNF-α) combined with BL-TABM and β-lactoglobulin all combine to potentiate the production of TNF-α by normal PBMNC.

Figure 36:
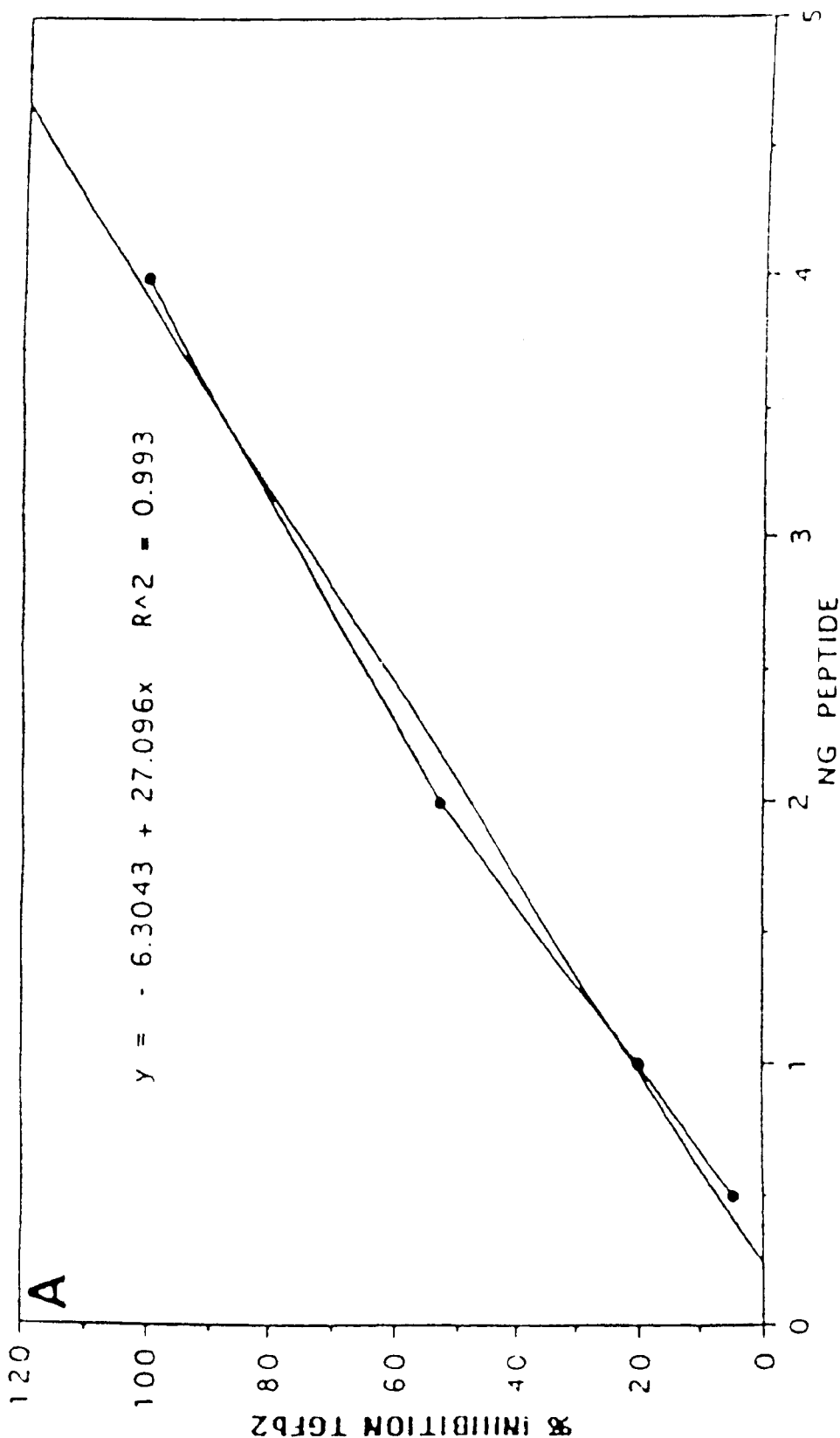
Figure 36:
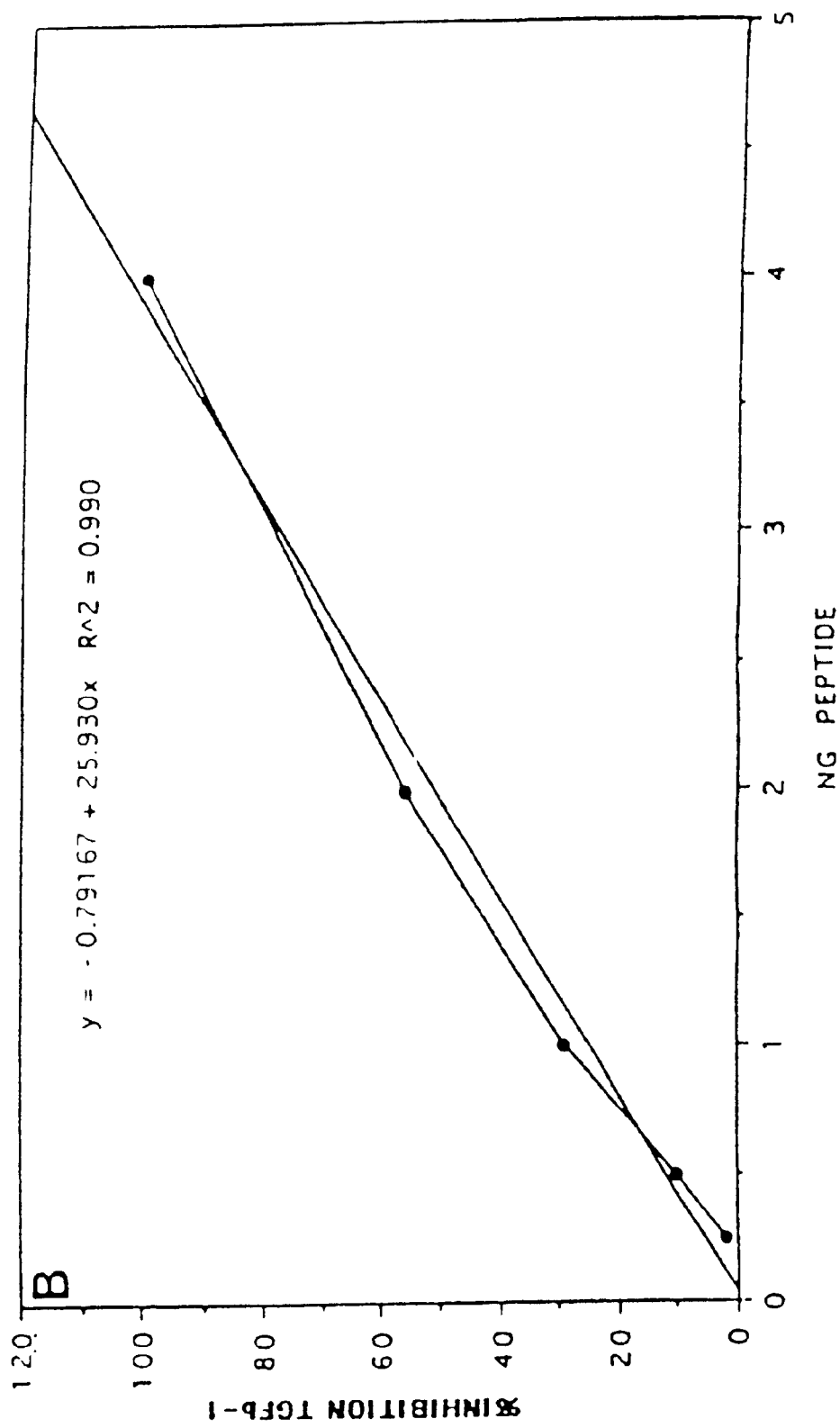
Figure 36C:
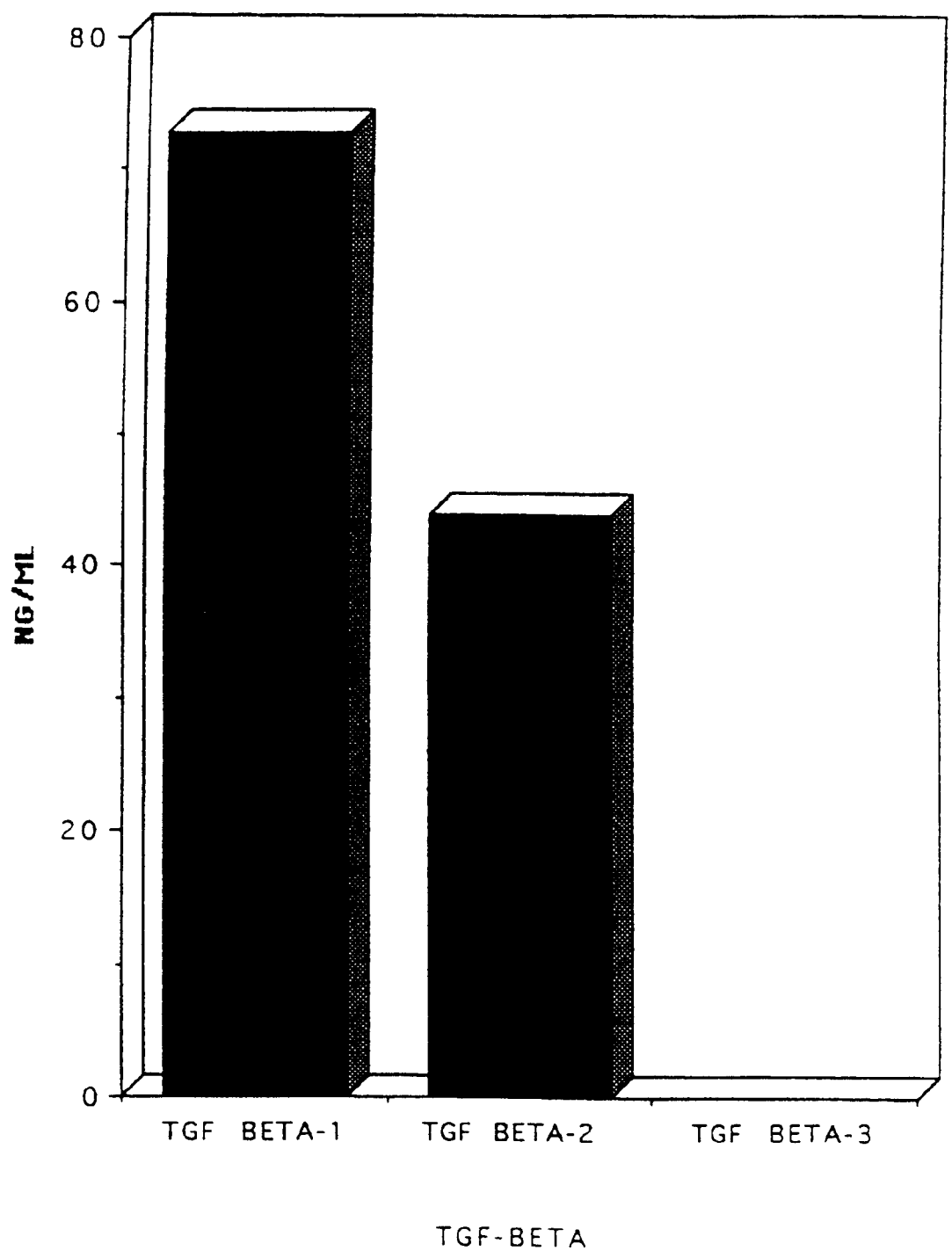

—●— b-Lactoglobulin, 0 ug/ml
—○— b-Lactoglobulin, 0.05 ug/ml
—■— b-Lactoglobulin, 0.5 ug/ml
—□— b-Lactoglobulin, 5.0 ug/ml FIGS. 36A–36C are a graphical representation showing detection of TGF-β in BL-TABm by ELISA. Ten to twenty μl BL-TABM were mixed with a 1:500 dilution of rabbit anti-TGF-β1, 2 or 3, and the mixture added to microtiter wells coated with 10 ng corresponding TGF-β1, 2 or 3 peptides. The inhibition of the binding of anti-TGF-β by BL-TABM was compared to that obtained by immunogenic peptide to compute the amount of TGF-β in the TABM.

$$\frac{O.D.\ anti\text{-}TGF\text{-}\beta + BL\text{-}TABM \times 100}{O.D.\ anti\text{-}TGF\text{-}\beta}$$

A) Inhibition of ELISA by TGF-β1 peptide
B) Inhibition of ELISA by TGF-β2 peptide
C) Quantity of TGF-β1 in BL-TABM based on ELISA inhibition.

Figure 37:
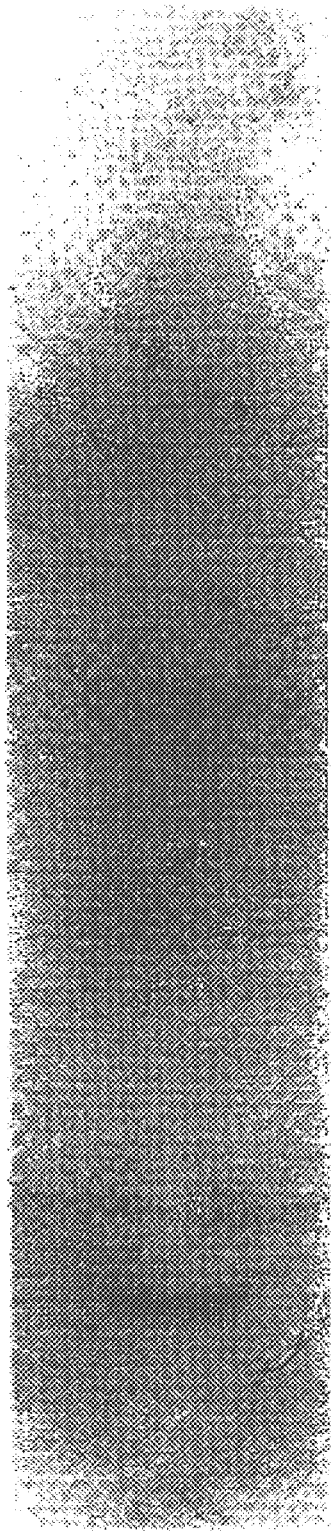

FIG. 37 is a photographic representation of immunoblotting of BL-TABM with anti-TGF-β antibodies. Eight hundred and seventy ng non-reduced BL-TABM were resolved and transferred to immobilon membranes. The milk-blocked membranes were incubated with rabbit anti-TGF-β2 antibodies, and bound antibody IgG and NBT-BCIP substrate.

The following abbreviations are used in the subject specification.

| Abbreviation | Definition |
| --- | --- |
| AL | α-Lactoalbumin |
| AG | Antigen captive ELISA |
| BA | Benzoic acid |
| BA-TABM | Benzoic acid specific TABM |
| BL (BLG) | β-Lactoglobulin |
| BSA | Bovine serum albumin |
| BA-HSA | Benzoic acid conjugated human serum albumin |
| CA | α-s-Casein |
| CTAB | Cetryl trimethyl ammonium bromide |
| ELISA | Enzyme linked immunosorbant assay |
| ES | Electrical stimulate |
| F-HSA (Form-HSA) | Formaldehyde conjugated human serum albumin |
| FCS | Fetal calf serum |
| FCSi | Heat inactivated FCS |

-continued

| Abbreviation | Definition |
| --- | --- |
| hTABM | Human TABM |
| HSA | Human serum albumin |
| HS | Horse serum |
| HSA-TABM | HSA specific TABM |
| MG3C9-1A12 | Anti human TABM monoclonal antibody |
| $M_r$ | Molecular weight |
| O.D. | Optical density |
| PBMNC | Peripheral blood mononuclear cells |
| PBS | Phosphate buffered saline |
| PBS-Tw | Phosphate buffered saline-Tween washing solution |
| R28,R30 | Rabbit anti-human TABM sera |
| SDS-PAGE | Sodium dodecyl sulphate-polyacrylamide gel electrophoresis |
| SNP | Sodium nitroprusside |
| SP | Substance P |
| TABM | T-cell antigen binding molecules or T-cell derived antigen binding molecules |
| TCR | T-cell receptor |
| TCRα-1 | Monoclonal antibody to TCR α chain |
| TMB | 3', 3, 5', 5-Tetramethyl benzidine |
| TNF-α | Tumour necrosis factor-α |
| TNP-BSA | Trinitrophenol conjugated BSA |
| Tw | Tween |

DETAILED DESCRIPTION OF THE PREFERRED EMBODIMENTS

The present invention provides an isolated immunointeractive molecule comprising a portion which is capable of specifically interacting with a TABM.

The TABM may be of animal or possibly avian origin. Preferred animals are mammals such as humans, primates, livestock animals (eg. sheep, cows, horses, donkeys, pigs), laboratory test animals (eg. rabbits, mice, guinea pigs), companion animals (eg. dogs, cats) and captive wild animals (eg. deer, foxes, kangaroos). Most preferably, the mammal is a human. Preferred avian species are chickens, ducks, ostriches, emus and caged birds. The immunointeractive molecule may be specific to a particular TABM or may broadly interact with a range of TABM. A particular TABM is conveniently defined by *inter alia* reference to epitopes, cytokine interacting ability and/or antigen specificity.

The immunointeractive molecule of the present invention is preferably an antibody and most preferably a monoclonal antibody or a recombinant, chemically synthetic, hybrid form, derivative or functional equivalent thereof. A "derivative" in this context includes a fragment, portion, part, homologue or analogue of an antibody and, more particularly, a monoclonal antibody. Where the interactive molecule is a monoclonal antibody, it may be the entire monoclonal antibody or it may be a TABM binding portion thereof or a hybrid between a carrier molecule and a TABM binding portion of a TABM specific monoclonal antibody. The present invention extends to polyclonal antibodies to TABM to the extent that the polyclonal antibody has been rendered monovalent to the specific TABM or has been otherwise derivatised. The present invention also extends to antibodies (monoclonal or polyclonal antibodies) to synthetic peptides or peptide fragments of a TABM or corresponding to a portion of a TABM. Reference hereinafter to an "immunointeractive molecule" specifically includes a monoclonal antibody as well as its derivatives and novel forms of polyclonal antibodies or monovalent polyclongal antibodies.

It is within the scope of this invention to include any second interactive molecules (eg. monoclonal or polyclonal antibodies or fragments of antibodies or synthetic antibodies) directed to the first mentioned immunointeractive molecules referred to above. Both the first and second immunointeractive molecules may be used in detection assays. Alternatively, the first immunointeractive molecule may be used with commercially available anti-immunoglobulin antibodies in diagnostic assays. An antibody as contemplated herein includes any antibody specific to any region of TABM. As stated above, the antibody may be specific to a particular TABM or may broadly interact to all TABM or a class of TABM.

Polyclonal and monoclonal antibodies are obtainable by immunization with purified or substantially purified TABM and either type may be utilized in for immunoassays. The methods of obtaining both types of sera are well known in the art. Polyclonal sera are less preferred but are relatively easily prepared by injection of a suitable laboratory animal with an effective amount of TABM, or antigenic part thereof, collecting serum from the animal and isolating specific sera by any of the known immunoadsorbent techniques. Although antibodies produced by this method are utilizable in virtually any type of immunoassay, they are generally less favoured because of the potential heterogeneity of the product.

The use of monoclonal antibodies in an immunoassay is particularly preferred because of the ability to produce them in large quantities and the homogeneity of the product. The preparation of hybridoma cell lines for monoclonal antibody production derived by fusing an immortal cell line and lymphocytes sensitized against the immunogenic preparation may be achieved by techniques which are well known to those who are skilled in the art. In one approach, a myeloma cell line such as P3-NS1-Ag4-1 (NS-1) is fused with spleen cells from an animal immunized with TABM. A convenient source of TABM for the immunization is TABM purified from Cohn Fraction III (Baxter Pharmaceutical). Alternatively, the TABM may be isolated from serum or other appropriate body fluid. A particularly useful hybridoma cell produced in accordance with the present invention is designated herein MG3C9-1A12 and produces monoclonal antibody MG3C9-1A12.

This aspect of the present invention is hereafter described with reference to one particularly useful means of producing an immunointeractive molecule in the form of a monoclonal antibody to TABM.

Human serum Cohn Fraction III is used as a source of TABM which is purified on a sepharcyl (eg. S-300) or sepharose (eg. 3C9) column. Rabbit anti-human TABM antisera is then prepared by immunising rabbits with human serum TABM. The polyvalent antisera are specific for human TABM produced by T-cells and do not bind human serum albumin, IgG, IgM or TGFβ1, 2 or 3 immunogenic peptides. Mice are then immunised with the purified TABM and the spleens removed. Spleen cells are fused with the P3-NS1-Ag-4-1 (NS1) myeloma cell line. Monoclonal antibody is then screened for enzyme linked immunosorbent assay (ELISA). For example, TABM monoclonal secreting cells are identified by the monoclonal antibody binding to immobilized human TABM. Binding activity is detected using a labelled anti-immunoglobulin antibody preparation. Cells are then cloned and grown to produce monoclonal antibody to TABM.

Accordingly, another aspect of the present invention provides a hybridoma cell line producing a monoclonal antibody comprising a binding portion specific to TABM.

More particularly, the present invention is directed to a hydriboma cell line having the characteristics of cell line MG3C9 producing a monoclonal capable of interacting with TABM. Preferably, the monoclonal antibody is MG3C9-1A12.

Another aspect of the present invention contemplates a method for detecting TABM in a biological sample from a subject said method comprising contacting said biological sample with an immunointeractive molecule specific for TABM or their derivatives or homologues for a time and under conditions sufficient for an immunointeractive molecule-TABM complex to form and then detecting said complex.

The presence of TABM may be accomplished in a number of ways such as by Western blotting and ELISA procedures. A wide range of immunoassay techniques are available as can be seen by reference to U.S. Pat. No. 4,016,043, 4,424,279 and 4,018,653. These include both the non-competitive assays as well as competitive binding assays. These assays also include direct binding of a labelled antibody to a target.

Sandwich assays are particularly useful. A number of variations of the sandwich assay technique exist, and all are intended to be encompassed by the present invention. Briefly, in a typical forward assay, an unlabelled immunointeractive molecule is immobilized on a solid substrate and the sample to be tested for the presence of a TABM is brought into contact with the bound molecule. After a suitable period of incubation, for a period of time sufficient to allow formation of an immunointeractive molecule-TABM complex, a second immunointeractive molecule specific to the TABM, labelled with a reporter molecule capable of producing a detectable signal is then added and allowed to incubate, allowing time sufficient for the formation of another complex of immunointeractive molecule-TABM-labelled interactive molecule. Any unreacted material is washed away, and the presence of the TABM is determined by observation of a signal produced by the reporter molecule. The results may either be qualitative, by simple observation of the visible signal, or may be quantitated by comparing with a control sample containing known amounts of TABM. Variations on the forward assay include a simultaneous assay, in which both sample and labelled antibody are added simultaneously to the bound antibody. In another variation, the first immunointeractive molecule is a polyclonal antibody and the second, labelled interactive molecule is TABM-specific monoclonal antibody. These techniques are well known to those skilled in the art, including any minor variations as will be readily apparent.

A particularly useful variation permits the identification of a TABM specific interactive molecule. In this assay, purified TABM are immobilized to a solid support such as a microtitre well. A sample, putatively carrying a TABM immunointeractive molecule, is brought into contact with the immobilized TABM. If present, the immunointeractive molecule binds to the immobilized TABM. An anti-immunoglobulin antibody preparation, labelled with a reporter molecule capable of providing an identifiable signal, is the then used to identify bound TABM-specific immunointeractive molecules.

In accordance with the present invention the sample is one which might contain TABM (or a TABM specific immunointeractive molecule) including serum, whole blood, cell extract, tissue biopsy, saliva, mucosal secretions, lymph, tissue fluid and respiratory fluid. The sample is, therefore, generally a biological sample comprising biological fluid but also extends to fermentation fluid and supernatant fluid such as from a cell culture.

In the typical forward sandwich assay, a first immunointeractive molecule having specificity for the TABM or antigenic parts thereof, is either covalently or passively bound to a solid surface. The solid surface is typically glass or a polymer, the most commonly used polymers being cellulose, polyacrylamide, nylon, polystyrene, polyvinyl chloride or polypropylene. The solid supports may be in the form of tubes, beads, discs or microplates, or any other surface suitable for conducting an immunoassay. The binding processes are well-known in the art and generally consist of cross-linking covalently binding or physically adsorbing. The polymer-antibody complex is washed in preparation for the test sample. An aliquot of the sample to be tested is then added to the solid phase complex and incubated for a period of time sufficient (e.g. 2–40 minutes or overnight if more convenient) and under suitable conditions (e.g. from room temperature to about 40° C. including from about 25° C. to about 37° C.) to allow binding of any subunit present in the antibody. Following the incubation period, the solid phase is washed and dried and incubated with a second immunointeractive molecule specific for a portion of the TABM. The second immunointeractive molecule is linked to a reporter molecule which is used to indicate the binding of the second immunointeractive molecule to the TABM. Similar considerations apply after screening for a TABM-specific immunointeractive molecule.

An alternative method involves immobilizing the target TABM molecules in the biological sample and then exposing the immobilized target to specific immunointeractive molecule which may or may not be labelled with a reporter molecule. Depending on the amount of target and the strength of the reporter molecule signal, a bound target may be detectable by direct labelling with the antibody. Alternatively, a second labelled immunointeractive molecule, specific to the first immunointeractive molecule is exposed to the TABM-first immunointeractive molecule complex to form a TABM-first immunointeractive molecule-second immunointeractive molecule tertiary complex. The complex is detected by the signal emitted by the reporter molecule.

A particularly preferred alternative method is to immobilise antigen on a solid support and then bring into contact the biological sample containing the putative TABM. The antigen is used, therefore, to trap the specific TABM. An anti-TABM antibody is then used to detect bound TABM either directly if labelled with a reporter molecule or indirectly via a labelled anti-immunoglobulin antibody.

By "reporter molecule" as used in the present specification, is meant a molecule which, by its chemical nature, provides an analytically identifiable signal which allows the detection of antigen-bound antibody. Detection may be either qualitative or quantitative. The most commonly used reporter molecules in this type of assay are either enzymes, fluorophores or radionuclide containing molecules (i.e. radiosotopes) and chemiluminescent molecules. Biotin and Avidin/Streptavidin may also be employed.

In the case of an enzyme immunoassay, an enzyme is conjugated to the second antibody, generally by means of glutaraldehyde or periodate. As will be readily recognized, however, a wide variety of different conjugation techniques exist, which are readily available to the skilled artisan. Commonly used enzymes include horseradish peroxidase, glucose oxidase, beta-galactosidase and alkaline phosphatase, amongst others. The substrates to be used with the specific enzymes are generally chosen for the production, upon hydrolysis by the corresponding enzyme, of a detectable colour change. Examples of suitable enzymes include alkaline phosphatase and peroxidase. It is also possible to employ fluorogenic substrates, which yield a fluorescent product rather than the chromogenic substrates noted above. In all cases, the enzyme-labelled immunointeractive molecule is added to the first immunointeractive molecule-TABM complex, allowed to bind, and then excess reagent is washed away. A solution containing the appropriate substrate is then added to the complex of immunointeractive molecule-TABM-immunointeractive molecule. The substrate will react with the enzyme linked to the second antibody, giving a qualitative visual signal, which may be further quantitated, usually spectrophotometrically, to give an indication of the amount of TABM which was present in the sample. The term "reporter molecule" also extends to use of cell agglutination or inhibition of agglutination such as red blood cells on latex beads and the like.

Alternately, fluorescent compounds, such as fluorescein and rhodamine, may be chemically coupled to antibodies without altering their binding capacity. When activated by illumination with light of a particular wavelength, the fluorochrome-labelled immunointeractive molecule adsorbs the light energy, inducing a state to excitability in the molecule, followed by emission of the light at a characteristic colour visually detectable with a light microscope. As in the ELISA, the fluorescent labelled immunointeractive molecule is allowed to bind to the first immunointeractive molecule-TABM complex. After washing off the unbound reagent, the remaining tertiary complex is then exposed to the light of the appropriate wavelength the fluorescence observed indicates the presence of the hapten of interest. Immunofluorescence and ELISA techniques are both very well established in the art and are particularly preferred for the present method. However, other reporter molecules, such as radioisotope, chemiluminescent or bioluminescent molecules, may also be employed.

The assays of the present invention are sensitive and can be used to detect nanogram amounts of TABM.

The present invention further extends to genetic assays for TABM. For example, anti-TABM antibodies may be used to screen expression libraries for genetic sequences encoding all or antigenic parts of TABM. This permits a ready source of recombinant TABM for diagnostic and therapeutic purposes and also provides genetic sequences such as primers and probes to screen an individual for mRNA specificity for a TABM gene or potential aberrations in a TABM gene. Accordingly, the present invention extends to nucleic acid molecules encoding a TABM as hereinbefore defined as well as genetic assays for TABM genes.

As stated above, the present invention extends to derivatives of the immunointeractive molecules. Derivatives including single or multiple amino acid substitutions, deletions and/or additions to the immunointeractive molecules. "Additions" to amino acid sequences include fusions with other peptides, polypeptides or proteins or fusions to nucleotides sequences.

Analogues of the immunointeractive molecule contemplated herein include, but are not limited to, modification to side chains, incorporating of unnatural amino acids and/or their derivatives during peptide, polypeptide or protein synthesis and the use of crosslinkers and other methods which impose conformational constraints on the proteinaceous molecule or their analogues. These types of modifications are useful in stabilizing the immunointeractive molecules for use in diagnostic assays in therapeutic protocols.

Examples of side chain modifications contemplated by the present invention include modifications of amino groups such as by reductive alkylation by reaction with an aldehyde followed by reduction with $NaBH_4$; amidination with methylacetimidate; acylation with acetic anhydride; carbamoylation of amino groups with cynate; trinitrobenzylation of amino groups with 2, 4, 6-trinitrobenzene sulphonic acid (TNBS); acylation of amino groups with succinic anydride and tetrahydrophthalic anhydride; and pyridoxylation of lysine with pyridoxal-5-phosphate followed by reduction with $NaBH_4$.

The guanidine group of arginine residues may be modified by the formation of heterocyclic condensation products with reagents such as 2,3-butanedione, phenylglyoxal and glyoxal.

The carboxyl group may be modified by carbodiimide activation via O-acylisourea formation followed by subsequent derivitisation, for example, to a corresponding amide.

Sulphydryl groups may be modified by methods such as carboxymethylation with iodoacetic acid or iodoacetamide; performic acid oxidation to cysteric acid; formation of a mixed disulphides with other thiol compounds; reaction with maleimide, maleic anhydride or other substituted maleimide; formation of mercurial derivatives using 4-chloromercuribenzoate, 4-chloromercuriphenylsulphonic acid, phenylmercury chloride, 2-chloromercuri-4nitrophenol and other mercurials; carbamoylation with cyanate at alkaline pH.

Tryptophan residues may be modified by, for example, oxidation with N-bromosuccinimde or alkylation of the indole ring with 2-hydroxy-5-nitrobenzyl bromide or sulphenyl halides. Tyrosine residues on the other hand, may be altered by nitration with tetranitromethane to form a 3-nitrotyrosine derivative.

Modification of the imidazole ring of a histidine residue may be accomplished by alkylation with iodoacetic acid derivative or N-carbethoxylation with diethylpyrocarbonate.

Examples of incorporating unnatural amino acids and derivatives during peptide synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, omithine, sarcosine, 4-amino-3-hydroxy-6-methylheptanoic acid, 2-thienyl alanine and/or D-isomers of amino acids. A list of unnatural amino acid, contemplated herein is shown below.

Crosslinkers can be used, for example, to stabilise 3D conformations, using homo-bifunctional crosslinkers such as the bifunctional imido esters having $(CH_2)_n$ spacer groups with n=1 to n=6, glutaraldehyde, N-hydroxysuccinimide esters and hetero-bifunctional reagents which usually contain an amino-reactive moiety such as N-hydroxysuccinimide and another group specific-reactive moiety such as maleimido or dithio moiety (SH) or carbodiimide (COOH). In addition, peptides can be conformationally constrained by, for example, incorporation of $C_\alpha$ and N-methylamino acids, introduction of double bonds between $C_\alpha$ and $C_\beta$ atoms of amino acids and the formation of cyclic peptides or analogues by introducing covalent bonds such as forming an amide bond between the N and C termini, between two side chains or between a side chain and the N or C terminus.

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgln |
|  |  | L-N-methylglutamic acid | Nmglu |
| cyclohexylalanine | Chexa | L-N-methylhistidine | Nmhis |
| cyclopentylalanine | Cpen | L-N-methylisoleucine | Nmile |
| D-alanine | Dal | L-N-methylleucine | Nmleu |
| D-arginine | Darg | L-N-methylysine | Nmlys |
| D-aspartic acid | Dasp | L-N-methymethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α-methylcyclohexylalanine | Mchexa |
| D-α-methylarginine | Dmarg | α-methylcylopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylisoleucine | Dmleu | α-naphthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cyclododecylglycine | Ncdod |
| D-N-methylalanine | Dnmala | N-cyclooctylglycine | Ncoct |
| D-N-methylarginine | Dnmarg | N-cyclopropylglycine | Ncpro |
| D-N-methylasparagine | Dnmasn | N-cycloundecylglycine | Ncund |
| D-N-methylaspartate | Dnmasp | N-(2,2-diphenylethyl)glycine | Nbhm |
| D-N-methylcysteine | Dnmcys | N-(3,3-diphenylpropyl)glycine | Nbhe |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl))glycine | Nser |
| D-N-methylisoleucine | Dnmile | N-(imidazolylethyl))glycine | Nhis |
| D-N-methylleucine | Dnmleu | N-(3-indolylyethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltryosine | Dnmtrr | N-methyl-α-naphthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Nglu |
| L-α-methylhistidine | Mhis | L-α-methylhomophenylalanine | Mhphe |

-continued

| Non-conventional amino acid | Code | Non-conventional amino acid | Code |
|---|---|---|---|
| L-α-methylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | Mser | L-α-methylthreonine | Mthr |
| L-α-methyltryptophan | Mtrp | L-α-methyltyrosine | Mtyr |
| L-α-methylvaline | Mval | L-N-methylhomophenylalanine | Nmhphe |
| N-(N-(2,2-diphenylethyl) carbamylmethyl)glycine | Nnbhm | N-(N-3,3-diphenylpropyl) carbamylmethyl)glycine | Nnbhe |
| 1-carboxy-1-(2,2-diphenyl-ethylamino)cyclopropane | Nmbc | | |

As stated above, these types of modifications may be important to stabilise the immunointeractive molecule if administered to an individual or for use as a diagnostic reagent.

Other derivatives contemplated by the present invention include a range of glycosylation variants from a completely unglycosylated molecule to a modified glycosylated molecule. Altered glycosylation patterns may result from expression of recombinant molecules in different host cells.

Another aspect of the present invention extends to the immunointeractive molecule in composition form. Such compositions are particularly useful as therapeutic compositions and may be referred to as pharmaceutical compositions. The compositions are useful in controlling TABM activity by administering an immunointeractive molecule capable of binding to the TABM and inhibiting or otherwise reducing the activity of the TABM. This is particularly important where the TABM is involved in immune suppression or immune activation. Accordingly, the present invention contemplates a composition comprising an immunointeractive molecule specific for TABM.

The composition forms suitable for injectable use include sterile aqueous solutions (where water soluble) or sterile powders for the extemporaneous preparation of sterile injectable solutions. It must be stable under the conditions of manufacture and storage and must be preserved against the contaminating action of microorganisms such as bacteria and fungi. The carrier can be a solvent or diluent containing, for example, water, ethanol, polyol (for example, glycerol, propylene glycol and liquid polyethylene glycol, and the like), suitable mixtures thereof, and vegetable oils. The preventions of the action of microorganisms can be brought about by various antibacterial and antifungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the immunointeractive molecule in the required amount in the appropriate solvent or diluent as followed by sterilization such as by filter sterilization. In the case of sterile powders for the preparation of sterile injectable solutions, the preferred methods of preparation are vacuum drying and the freeze-drying technique which yield a powder of the immunointeractive molecule plus any additional desired ingredient from previously sterile-filtered solution thereof.

Pharmaceutically acceptable carriers and/or diluents include any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the immunointeractive molecule, use thereof in the therapeutic compositions is contemplated. Supplementary active ingredients can also be incorporated into the compositions.

The principal immunointeractive molecule will be added in a concentration effective to interact to a TABM and inhibit or reduce the function of the TABM. For example, an effective amount may range from about 10 ng to about 2000 ng, or 50 ng to about 1000 ng or 100 ng to about 500 ng or other suitable effective amount. Of course, larger amounts may be administered such as from 10 μg to about 2000 mg. It is sometimes more convenient to express dosage amounts in terms of kilogram per body weight. Accordingly, the effective amount may be from, for example, about 0.5 ng/kg body weight to about 1000 ng/kg body weight or an amount there between.

Although not intending to limit the present invention to any one theory or mode of action, the main function of TABM is likely to be immuno-regulatory. In a murine model, for example, a rise in TABM accompanies the humoral response. In most studies to date, the function of TABM has been suppression of the cell-mediated response to specific antigens. Particularly high levels of TABM have been reported in experimentally induced immune deviation, indicating a Th2 response with suppression of the Th1 response.

TABM are associated with cytokines, in particular TGF-β and IL-10. As is exemplified herein, the inventors have purified TABM specific to β-lactoglobulin (BL), from a patient intolerant to cow's milk, and TABM specific to benzoic acid conjugated to human serum albumin (BA-HSA) from another patient sensitive to the solvent toluene. In both cases, the presence of TGF-β has been detected.

It is proposed herein that TABM act by focusing cytokines such as TGF-β to sites where the antigen is localised. TGF-β is a potent inhibitor of cell mediated immunity and increased local concentrations of this cytokine would inhibit the development of a cell mediated immune response to the antigen. Most of the TGF-β associated with TABM is present in an inactive form. When TABM bind to antigen, the TGF-β becomes activated. This seems to occur optimally at a relatively low antigen concentration.

In addition, elevated levels of total TABM are detected, in accordance with the present invention, in patients symptomatic with AIDS and antigen specific TABM in individuals with chronic filiariasis or asymptomatic carriers of the filiarial worm. In both these disorders, there is suppressed cell mediated immunity to the infectious agent.

The inventors have performed clinical studies, measuring levels of antigen specific TABM.

In a study of milk intolerant patients, the inventors found raised levels of TABM to one or more of the milk proteins, β-lactoglobulin, α-lactalbumin and/or α-s-casein, in the patient group when compared to controls.

In another study, the inventors found elevated levels of TABM to BA-HSA in patients sensitive to the solvent toluene. This antigen was thought to be suitable as benzoic acid is a major matabolite of toluene.

TABM may also bind to drug, drug-protein conjugates or their metabolites and have a role in drug mediated allergies.

The immunointeractive molecule of the present invention was also used to measure mannan specific TABM in a study of women susceptible to thrush. Thrush was used as a model as the literature indicates that cell mediated immunity is suppressed. The inventors found elevated levels of TABM specific to *Candida albicans* mannan in these patients.

It is known that certain cytokines enhance the release of neuropeptides from sensory nerves. This has been extensively studied in the case of Interleukin-1. The inventors have now found that TGF-β also enhances the release of neuropeptides from sensory nerves. This effect is dose dependent and lost when animals are pre-treated with Capsaicin. The effect is blocked by anti TGF-β antibody.

The BA-TABM also enhances the release of neuropeptides in a dose dependent manner. This effect is blocked by anti-TGF-β antibody and is attributable to the co-presence of TGF-β in the TABM preparation. The addition of antigen (BA-HSA) to the TABM may enhance or inhibit neuropeptide release: there is enhancement at low concentrations of BA-HSA and inhibition at higher concentrations. This seems consistent with the effect of antigen concentration in activating TGF-β in the TABM. TABM detectable with the immunointeractive molecule of the present invention indicates immune deviation with suppression of the cell mediated immune response to specific antigens. TABM levels may provide an index of the balance between Th1 and Th2 immune responses. This could be important in assessing the immunological status in cancer, autoimmunity and infectious diseases. Also, the presence of TABM may indicate a continuing immune response with a failure to achieve immune tolerance to non replicating antigens, for example to common food proteins. TABM specific to such proteins may indicate "low dose tolerance" and not anergy or deletion.

As an example, the measurement of TABM specific to melanoma antigens may be helpful in evaluating the cell mediated immune response to this type of tumour. An impairment of the response could indicate a risk of dissemination. A similar measurement strategy may be important in other cancers where the balance between cell mediated and humoral immunity is pivotal in controlling the tumour growth.

TGF-β is reported as modulating certain parasitic diseases, particularly by limiting tissue damage. The inventors have identified TABM in the sera of patients who are chronic carriers of filiariasis. TGFβ is reported to inhibit cell mediated immunity in schistosomiasis, sleeping sickness and leishmaniasis. Measurement of TABM in such infections may be helpful in evaluating resistance to infection and the susceptibility to tissue damage.

TABM specific to viral peptides are present in patients with AIDS. This may indicate a decline in cell mediated immune response to the virus. Similar measurements may be helpful in patients with serum hepatitis who have become carriers, where there is thought to be a similar abnormality in the immune response to the virus. Also it is possible that serial measurement of total TABM may be of assistance in assessing the progress of AIDS.

In mycobacterial infections, for example tuberculosis and leprosy, the immune defence is critically dependent on the cell mediated immune response. If TABM levels to mycobacterial antigens are raised this may indicate a vulnerability to these infections. Measurement of TABM to antigens of *Mycobacterium leprae* may help distinguish between tuberculoid and lepromatous leprosy.

As indicated above, an immune response with production of TABM to food proteins or simple chemicals could be associated with persistent symptoms. TABM specific to environmental antigens could be important in many cases of food intolerance, which can cause functional bowel symptoms, or chemical sensitivity. Assays of TABM for chemical antigens may be helpful in evaluating at risk personnel who are occupationally exposed to chemicals. Similar assays could be of assistance in evaluating drug reactions and the possible adverse effects of silicon implants.

In some cases it would be helpful to determine the immune response produced by vaccination. For example in the case of tuberculosis it is preferable that a Th1 immune response is induced. The measurement of TABM specific to antigens used for vaccination may indicate the outcome of the vaccination procedure i.e. whether a predominantly Th1 or Th2 response has been achieved.

In certain "auto-immune" disorders such as multiple sclerosis, Th1 immune responses may be directed to self antigens. Therapy can be associated with a shift in the response to the Th2 mode. For example this may be the outcome when patients with multiple sclerosis are treated with Interferon. Serial measurement of TABM to the auto antigens may help monitor the effectiveness of treatment.

Accordingly, the present invention further contemplates a method for assessing, monitoring or diagnosing a disease or other physiological condition by determining the levels of total or antigen-specific TABM in an individual.

In a further embodiment, an individuals own TABM may be purified and the readministration to the same person or a related person. Accordingly, the antibodies to TABM have a particularly useful role in purifying TABM for potential clinical use.

Assaying the level of TABM and therapy involving TABM may also be important in allograft rejection and in the regulation of immune responses.

For example, a excess Th1 response has been associated with miscarriage and spontaneous abortion. The immune response may be regulatable to protect the developing foetus such that the foetus does not provoke an unwanted immune response. TABM and assaying TABM levels are important in this respect and are encompassed by the present invention.

Accordingly, assays for TABM levels are important for a range of diagnoses including the detecting of microbial and parasitic infection, cancer, neuropeptide release and allergies including drug, milk and food allergies.

The present invention is further described by the following non-limiting Examples.

Examples 1–19 relate to the production and characteristics of a monoclonal antibody to TABM.

EXAMPLE 1

TABM

Five grams of human serum Cohn Fraction III (Baxter Pharmaceuticals) was mixed with 10 ml 2M urea in phosphate-buffered saline (PBS, pH 7.2), and after 15 min agitation, the mixture was centrifuged for 30 min at 9,000 rpm. The supernatant was retained and loaded on a 3.5 cm×67 cm column containing sephacryl S-300 equilibrated in the same buffer. The column was pumped at 950 ml/hr and 5 ml column fractions were collected. Based on the predetermined chromatographic positions of IgM, IgG, human albumin and ovalbumin, the column fractions were pooled as Fraction I, void volume (>MW 600,000), Fraction II, (MW $10^5$–$3\times10^5$), Fraction III, (MW $4\times10^4$–$1\times10^5$), Fraction IV (MW<$3\times10^4$). Fractions containing TABM (see Table 1) were pooled and precipitated by the addition of $(NH_4)_2SO_4$ to a final concentration of 43%, as described (2). The precipitated proteins were solubilized in PBS and then absorbed with sepharose 4B beads conjugated with anti-human Ig (whole molecule, Sigma) and anti-human albumin (Sigma, St. Louis, Mo.).

EXAMPLE 2

Antisera/Antibodies

Rabbit anti-human TABM sera (R28, R30) were prepared as described by immunizing rabbits with human serum TABM prepared by chromatography in carboxymethyl cellulose and immunoabsorption. The antisera are specific for human TABM produced by T lymphocytes and do not bind human albumin, human IgG, IgM or TGF-β1, 2, or 3 immunogenic peptides. Monoclonal antibodies to TcR α (TcRα-1) and beta chains (TcRβ-1) were purchased from T-Cell Diagnosis (Woburn, Mass.) and T Cell Sciences (Cambridge, Mass.), respectively. Rabbit anti-mouse IgG and IgM (Jackson Immunoresearch Lab, Inc.) was used to isotype the monoclonal antibodies.

EXAMPLE 3

Immunisation of Mice With Human TABM

Female BALB/c mice, 6–8 weeks old were immunized intraperitoneally (i.p.) with 5–10 μg of purified human TABM in complete Freund's adjuvant (Sigma Chemical Company). A second i.p. injection was given with Freund's incomplete adjuvant (Sigma Chemical Company) one month later. The third and fourth immunisations were given in a solution of Poly A and Poly U (equal volumes of 1 mg/ml of each) at 3 and 7 months respectively. Four days before the fusion a fifth i.p. immunisation in PolyA:Poly U was given.

EXAMPLE 4

Spleen Cell Preparation

The spleen was removed and placed in serum free RPMI-1640, followed by two rinses. Spleen cells were teased out, collected into a tube and larger clumps allowed to settle. Only the supernatant containing single cells were collected. The cells were washed twice in serum free RPMI-1640 culture medium. Cell viability was near 100%.

EXAMPLE 5

Myeloma Cells

The P3-NS1-Ag 4-1 (NS-1) myeloma cell line was used and grown in RPMI-1640 containing 10% v/v heat inactivated (56° C., 30 min) fetal calf serum (FCS). Cells in logarithmic growth were centrifuged and resuspended in 45 ml serum free medium. The cells were washed twice in serum free medium and a cell viability count made and found to be >95% viable.

EXAMPLE 6

Fusion

The appropriate number of spleen and myeloma cells were added together, mixed well and centrifuged (third wash), thoroughly draining the supernatant. Cell fusion was carried out essentially as outline by Kohler and Milstein (1) with the following changes: a 50% w/v solution of PEG 4000, (Gibco BRL, N.Y.) was used, the red blood cells in the spleen cell preparation were not lysed, the number of spleen to myeloma cells was $2\times10^6$:$55\times10^6$ (approximately 2:1). The selection medium (RPMI-1640 15% v/v bovine serum (FCS)+HAT was added at 24 hr. The medium also contained 10% v/v of P338 (IL-6) conditioned medium. Dividing cells were passaged into RPMI-1640 15% v/v FCSi HT without IL-6 conditioned medium, then into RPMI-1640 15% v/v FCSi. Subsequently cells were adapted to culture in RPMI-1640 10% v/v FCSi.

EXAMPLE 7

Screening for Monoclonal Antibody

The screening of fused cells for the production of specific antibody was carried out using the enzyme linked immunosorbent assay (ELISA). A 96 well ELISA plate (Costar, Cambridge, Mass.) was coated with purified human TABM at 500 ng/well in 0.06M carbonate buffer, pH 9.5 and incubated overnight at room temperature. The plate was washed 5 times with PBS-0.05% v/v Tween-20 (PBS-Tw) and 50–100 μl of culture supernatant from individual wells with hybrids was added. The samples were incubated at 37° C. for 90 mins, followed by washing with PBS-Tw. A peroxidase conjugated sheep anti-mouse immunoglobulins (Silenus, Australia) was diluted 1/2000 in PBS-Tw-1% w/v gelatin and 100 μl placed per well. Incubation was carried out at 37° C. for 90 mins, followed by washing. The reaction was developed with 3',3,5',5-tetramethyl benzidine (TMB) substrate (KPL, Mass.) at room temperature until an OD of approximately 2 was obtained. The reaction was stopped with 2M $H_2SO_4$ and the plate OD read at 450 nm.

EXAMPLE 8

Cloning of Hybridoma Cells

The cloning of a positive "parent" hybrid was carried out by the limiting cell dilution assay. Cells were diluted so that on cell in 200 μl of RPMI 1640-15% v/v FCSi were plated per well of 96 well flat bottom tissue culture plate (NUNC, Denmark). After 4–5 days, wells were screened visually to identify those wells with a single clone. At approximately 10 days culture, supernatants were screened by ELISA to identify positive antibody producing clones. Most wells were screened twice for antibody activity.

EXAMPLE 9

Production of Monoclonal Antibody in Culture Supernatant

Cloned hybridoma cells (10–20 ml) in logarithmic growth were added to 50–60 ml RPMI 1640-15% v/v FCSi culture medium in 500 ml glass bottles. After 1–2 days an equal volume of serum free medium was added and the cells allowed to grow to death (5–6 days). The culture supernatant was collected by centrifugation and stored at 4° C.

EXAMPLE 10

Production of Monoclonal Antibody in Ascites

Eight week old female BALB-c mice were injected i.p. with 0.5 ml of pristane (Sigma Chemical Company). Six days later, mice were injected i.p. with $3.75 \times 10^6$ cloned cells in serum free culture medium. Ascites was collected 20 days later, centrifuged to remove cells and pristane and stored frozen.

EXAMPLE 11

Isotyping of the Anti-Human TABM Monoclonal Antibody

An ELISA with similar conditions as above was carried out using rabbit anti-mouse IgG and rabbit anti-mouse IgM antibodies (Jackson Immunoresearch Lab, Inc, USA). The enzyme conjugate was peroxidase conjugated sheep anti-rabbit immunoglobulins (Silenus, Australia).

EXAMPLE 12

Specificity of the Anti-Human TABM Monoclonal Antibody

ELISA plates were coated at 500 ng/well with various proteins which included: Human serum albumin (Calbiochem, Calif.), bovine serum albumin, beta-lactoglobulin, casein, (Sigma Chemical Company), "Intragam"-human immunoglobulin (CSL, Melbourne), and human TABM as a positive control. After binding, a 1/2000 dilution of purified mouse monoclonal antibody to human TABM was added and incubated at 37° C. for 90 minutes. After washing, a peroxidase labelled sheep anti-mouse was added.

EXAMPLE 13

Purification of the Mouse Anti-Human TABM Monoclonal Antibody

A streptococcal protein-G column (Pharmacia, Sweden) was used to isolate the monoclonal antibody to human TABM. The culture supernatant adjusted to pH7.2 or ascites diluted in PBS (pH 7.2) was filtered through a 0.45 $\mu$ filter and pumped through the column at approximately 1.5 ml per min. The column was washed with PBS pH 7.2, until the chart recorder returned to baseline. The monoclonal antibody was eluted with 0.1M glycine-HCl pH2.8 and neutralized with 1/10 volume of 1M TRIS pH 7.0 followed by dialysis overnight against PBS at 4° C. The antibody was collected and concentrated in an Amicon (Mass., USA) flow cell using a YM30 filter. The protein content was measured using the Biorad protein assay micromethod and bovine gamma globulin as the standard. Purified antibody and standard were diluted in PBS.

EXAMPLE 14

Polyacrylamide Gel Electrophoresis in SDS (SDS-PAGE)

Proteins were mixed 1:1 with SDS-PAGE sample buffer ±5% v/v $\beta_2$-mercaptoethanol and boiled 5 min. The proteins were then resolved in 8–25% w/v or 10–15% w/v polyacrylamide gradient gels using the PHAST (Pharmacia) system. Electrophoresed proteins were silver-stained. Molecular weights were determined by the mobilities of pre-stained (Biorad).

EXAMPLE 15

Immunoblotting

Proteins resolved by SDS-PAGE were electrophoretically transferred to a polyvinylpyrollidone (immobilon, Millipore) membrane. The membrane was blocked by incubation in 10 ml 5% w/v powdered milk for 2 hr at 37° C. The membrane was washed and then incubated overnight at 4° C. with 10 ml of 1:1000 monoclonal anti-TABM antibodies in wash buffer (3). Bound antibodies were detected by the addition of 10 ml alkaline phosphatase-conjugated goat anti-murine IgG (human IgG absorbed) antibodies and incubation at 4° C. for 2 hrs. The membrane was then washed for 1 hr and CSPD chemiluminescent substrate (Boehringer-Mannheim, Indianapolis, Ind.) was added to the membrane according to the manufacturer's instructions. Kodak X-ray film was overlaid on the membrane and the exposure was held 1 hr at ambient temperature, 1 hr at 37° C. Following exposure the film was automatically developed.

EXAMPLE 16

Enzyme Linked Immunsorbent Assay (ELISA)

Generally, microtiter trays were coated with 100–1,000 ng/well protein and blocked with 1% w/v gelatin. A dilution of primary antibody (rabbit, mouse) in wash buffer were incubated 1–1.5 hr at 37° C., and after washing alkaline phosphatase conjugated goat and rabbit or mouse 1 g (whole molecule), antibody was incubated with the microtiter trays for 1–1.5 hr at 37° C. Bound antibody was visualized with p-nitrophenyl phosphate substrate.

The screening of fused cells for the production of specific antibody was carried out using the ELISA. A 96-well ELISA plate (Costar, Cambridge, Mass.) was coated with purified human TABM at 500 ng/well in 0.06M carbonate buffer, pH 9.5 and incubated overnight at room temperature. The plate was washed 5 times with PBS-0.05% v/v Tween-20 (PBS-Tw) and blocked with 1% w/w gelatin in carbonate buffer at 37° C. for 90 min. Fifty to 100 $\mu$l of culture supernatant from individual wells with hybrids was added. The samples were incubated at 37° C. for 90 min. followed by washing with PBS-Tw. A peroxidase conjugated sheep anti-mouse immunoglobulins (Silenus, Australia) was diluted 1/2000 in PBS-Tw-1% w/v gelatin and 100 $\mu$l placed per well. Incubation was carried out at 37° C. for 90 min, followed by washing. The reaction was developed with 3',3,5',5-tetramethylbenzidine (TMB) substrate (KPL, Mass.) at room temperature until an OD of approximately 2 was obtained. The reaction was stopped with 2M $H_2SO_4$ and the plate CD read at 450 nm.

EXAMPLE 17

Purification of Cohn Fraction III TABM

Because TABM have the electrophoretic mobility of alpha and (some) beta globulins (2) the inventors tested Cohn Fraction III and IV (gamma globulin fraction) proteins for TABM using the ELISA. Cohn Fraction III proteins tested positive for TABM, and TABM were not detected in the gamma globulin fraction.

To purify TABM, Cohn Fraction III proteins soluble in PBS/urea were precipitated with 43% $(NH_4)_2SO_4$, and the precipitated proteins were dissolved in PBS/urea and fractionated by chromatography in sephacryl S-300. Fractions corresponding to molecular weights<30,000–<600,000 were obtained, and each fraction was assayed by ELISA for TABM. Most TABM were detected when 50–100 ng of void volume (Fraction I>$10^6$ d) (Table 1) proteins were assayed. TABM were also detected when 500 ng sephacryl fraction II proteins were assayed. Immunoglobulins were also detected by ELISA in the void volume fraction. Void volume (Fraction I) proteins were reprecipitated with 43% w/v $(NH_2)_4SO_4$ and solubilised, sephacryl fraction I proteins were absorbed 2X with anti-human Ig, anti-human albumin antibodies conjugated to sepharose beads and then assayed by ELISA. The absorbed proteins tested position for TABM, and TcR α chain epitopes, but not β chain epitopes, TGF-β1 and 2 epitopes, but not human immunoglobulin or albumin (FIGS. 1A–C). As shown in FIG. 2, reduced Fraction I proteins resolved as Mr 28,000 proteins. Non-reduced proteins did not enter the gel.

EXAMPLE 18

Production of Monoclonal Antibodies

BALB/c mice were immunized with Cohn Fraction III TABM and sera assayed for anti-TABM antibodies by ELISA against these proteins. Mice that tested positive for anti-TABM antibodies were used as a source of spleen cells for fusion. Clones producing anti-TABM antibodies were subcloned. As shown in FIG. 3, culture supernatants from clone MG3C9-1A12 reacted well with 500 ng purified TABM, but did not react in ELISA with 500 ng IgG, IgM, human albumin, IgA, or TGF-β1, 2, 3 immunogenic peptides. Other clones (for example, 2B3) did not react with TABM. Clone MG3C9-1A12 was subcloned and assayed for anti-TABM antibody. As shown in FIGS. 4A and B, subcloned, monoclonal MG3C9-1A12 culture supernatant and ascitic fluid reacted strongly with TABM (FIG. 4A), and detected less than 50 ng TABM (FIG. 4B). ELISA using heavy chain-specific anti-murine Ig demonstrated that MG3C9-1A12 is IgG2b. In addition, the monoclonal antibody MG3C9-1A12 reacts with TABM in immunoglobulin depleted serum (FIG. 4C).

Serum from a patient with a high titer of TABM to benzoic acid conjugated to HSA (BA-HSA) (toluene is metabolised to benzoic acid) was adsorbed to sepharose beads conjugated with monoclonal MG3C9-1A12. The beads were washed and then eluted with pH 2.8 glycine. Serum molecules bound by monoclonal MG3C9-1A12 were characterised further by absorbtion to and elution from BA-BSA-sepharose beads. The eluate (benzoic acid-HSA binding) TABM obtained from the beads were coated to microtiter trays for ELISA with monoclonal antibodies to TABM or TcR. As shown by ELISA (FIG. 5), monoclonal MG3C9-1A12 bound to BA-HSA binding TABM. An antibody to Tcr Cα (but no anti-Tcr Cβ or Cδ) also bound to BA-HSA-specific TABM recognised by monoclonal MG3C9-1A12.

EXAMPLE 19

Monoclonal MG3C9-1A12 is Specific for Antigens in Human Serum Proteins and Extracts of T Lymphocytes Because the TABM used as immunogens for monoclonal antibody MG3C9-1A12 are derived from human serum, the inventors determined whether MC3C9-1A12 would bind to unfractionated serum. Dilutions of human serum, fetal bovine and sheep serum, and sera from the cynomologous monkey (*Macaca fusicularis*) and Rhesus monkeys were coated to microtiter trays, and as shown in FIG. 6, monoclonal MG3C9-1A1 2reacted with wells coated with 100 μl of 1:20,000–1:40,000 dilutions. The antibody reacted weakly to cynomologous serum, and more strongly to Rhesus monkey serum. However, the "titer" (1:5000) of TABM antibody (MG3C9-1A12) identified an Mr 28,000 molecular species in human serum and the purified TABM used to make the monoclonal antibody (FIG. 7).

To determined further the specificity of monoclonal MC3C9-1A12, Jurkat (T) and A-1 (B) cells were lysed with Triton X-100, and the lysates mixed with MG3C9-1A 12 sepharose beads. After incubation, the beads were washed and eluted with 0.2M $NaCO_3$. Aliquots of the eluate were reduced and resolved by SDS-PAGE. As shown in FIG. 8, Mr 23,000 Jurkat cellular proteins were eluted from monoclonal MG3C9-1A12 sepharose beads and B-cell proteins were not absorbed to the beads. In addition, MG3C9-1A12 did not bind to T or B lymphocytes as judged by immunofluorescent staining. Furthermore, FIG. 8B shows that B-cells do not contain surface TABM. In contrast, strong binding was shown for T-cells and TABM controls. Examples 20 to 29 relate to the isolation and characterization of a TABM specific for the hapten, benzoic acid-human serum albumin (BA-HSA).

In a patient with a high titre of TABM to BA-HSA, the inventors purified TABM to the antigen using a monoclonal antibody to TABM (see Examples 1–19). The purified TABM comprises a polymer, having monomeric units of molecular weight 28,000. TABM are associated with the cytokine TGF-β. The BA-HSA specific TABM (BA-TABM) also show an apparent cross-reactivity with both dinitrophenol and oxazolone conjugated to human serum albumin, and binds weakly to formaldehyde and trimellitic acid (TMA) conjugated to human serum albumin.

The TGF-β becomes activated when TABM bind to antigen. Although this TABM may suppress cell mediated immunity to specific chemicals, these other properties could result in symptom production.

EXAMPLE 20

Patient

The serum used to purify TABM specific for BA-HSA was obtained from a 22 year old female patient sensitive to toluene.

Following toluene exposure (15 ppm for 20 minutes) she reported fatigue, headache, lower back pain and poor concentration. Neuropsychological assessment demonstrated a decline in performance on tests evaluating immediate and delayed memory recall (Babcock Stores) and psychomotor coordination (Symbol Digit Test) following the toluene exposure.

The patient has reported adverse reactions to other chemicals at low levels of exposure with heachache, fatigue, impaired concentration, irritability and muscle pain. Chemicals provoking reactions included solvents, perfume and vehicle exhaust.

EXAMPLE 21

Purification of Serum TABM Specific for Benzoic Acid-HSA

One hundred milliliters of serum were collected from the patient and stored frozen until required. It was thawed, filtered ad saturated ammonium sulfate added to 43% w/v. The slurry was then centrifuged at 9000 rpm and the supernatant removed. The precipitate was dissolved in PBS pH 7.2 in approximately half the starting volume and dialysed against PBS overnight at 4° C. The extract was then passaged through a sepharose affinity column (Pharmacia) onto which protein-G purified mouse monoclonal antibody to human TABM (MG3C9-1A12) was coupled. The sample was pumped through the column, following by washing with PBS to remove unbound proteins. The serum 'total' TABM bound by the anti-human TABM antibody were eluted with pH 2.8 glycine, neutralized with TRIS and dialysed against PBS overnight at 4° C. The purification of antigen specific TABM to BA-HSA were recovered from a BA-HSA-sepharose affinity column. The antigen is referred to herein as BA-TABM. Before elution with pH 2.8 glycine, the column was thoroughly washed with PBS until the recorder returned to baseline. The BA-TABM were then dialysed into 100 mM TRIS, 150 mM NaCl pH 7.2 overnight at 4° C. The non-binding proteins were also collected and dialysed. All samples collected had n-octyl glucopyranoside (OG; ICN, Calif.) added to 30 mM then frozen in aliquots. A protein determination was done using the Biorad dye reagent and BSA as standard.

EXAMPLE 22

Purification of TABM from Cohn Fraction III

Human serum TABM previously isolated from Cohn Fraction III by gel filtration for the production of the monoclonal antibody (Examples 1–19), were used as a positive control in various experiments. These were labelled Cohn FIII-TABM.

EXAMPLE 23

Titration of BA-HSA Specific TABM with Anti-Human Antibody (MG3C9-1A12) (FIG. 9)

Different preparations of human TABM, human IgG (Intragam) for infusion (CSL, Melbourne), HSA (Calbiochem) and BSA (Sigma) were coated onto ELISA plates (Costar, Cambridge, Mass.) overnight at room temperature. The plate was washed 5 times with PBS-Tween (PT) and blocked with 200 µl 1% w/v HSA (CSL, Melbourne) in PBS for 90 minutes at 37° C. One hundred µl protein-G purified mouse monoclonal antibody (MG3C9-1A12) to human TABM (25× supernatant) was diluted 1/2000 in PBS-Tw-1% gelatin (PTG), added to the wells and incubated for 90 minutes at 37° C. The plate was washed 5 times and peroxidase conjugated sheep anti-mouse immunoglobulin G (Silenus, Australia) diluted 1/1000 in PTG was added to the wells and incubated for 90 minutes at 37° C. The reaction was developed with 3',3,5',5-tetramethylbenzidine (TMB) substrate (KPL, Mass.) at room temperature until an OD of approximately 2 was obtained. The reaction was stopped with 2M $H_2SO_4$ and the optical density read at 450 nm.

EXAMPLE 24

The Presence of TABM and IgG in Different TABM Preparations and Proteins Coated Directly onto ELISA Plates (FIG. 10)

Different TABM preparations and proteins were serially diluted and coated directly onto ELISA plates, overnight at room temperature. The presence of TABM were detected using the monoclonal anti-human TABM (1/2000, for 90 minutes at 37° C.) and peroxidase labelled sheep anti-mouse immunoglobulins, 1/4000 for 90 minutes at 37° C. IgG was detected using a peroxidase labelled sheep anti-human IgG (Silenus, Australia), 1/4000 for 90 minutes at 37° C. The reaction was completed as described above.

EXAMPLE 25

The Presence of Antigen Specific IgG in Different TABM and Protein Preparations (FIG. 11)

HSA and the haptens BA-HSA, DNP-HSA and FORM-HSA were coated onto ELISA plates at 250 ng/well, in carbonate buffer overnight at 4° C. Patient serum, 'total' TABM and BA-TABM were serially diluted and added to the antigens for 90 minutes at 37° C. After washing, peroxidase labelled sheep anti-human IgG was applied for 90 minutes at 37° C.

EXAMPLE 26

The Presence of Antigen Specific TABM in Different TABM and Protein Preparations (FIG. 12)

The hapten BA-HSA and HSA (control) were each plated at 200 ng/well. Patient serum, total TABM and BA-TABM preparations were serially diluted and added to the antigens and incubated for 90 minutes at 37° C. The presence of antigen specific TABM were detected using the mouse anti-human TABM antibody. Peroxidase labelled sheep anti-mouse immunoglobulins was then added and incubated for 90 minutes at 37° C.

EXAMPLE 27

Competitive Inhibition ELISA for TABM with a Panel of Haptens or Non-Hapten Molecules Against Plate Bound BA-HSA Antigen (FIGS. 13 and 14)

To determined the antigen specific reactivity of BA-TABM toward BA-HSA and other haptens, a competitive ELISA was used. The ELISA plate was coated with BA-HSA (250 ng/well) in carbonate buffer overnight at 4° C. The plate was washed and blocked with 1% w/v HSA in PBS for 90 minutes at 37° C. Serum from the patient with high levels of TABM to BA-HSA was used at a dilution of 1/400, in PBS. The competing antigens or haptens were serially diluted (½) in the diluted serum to give a range equivalent to 5000–312.5 ng per well. The antigens and haptens tested included human serum albumin (HSA), bovine serum albumin (BSA), BA-HSA, trinitrophenol conjugated to BSA (TNP-BSA) and formaldehyde conjugated to HSA (F-HSA). The serum and antigen/hapten mixtures were first pre-incubated for 40 minutes at 37° C. before adding to the BA-HSA coated ELISA plate. The plate was then incubated for 60 minutes at 37° C. After washing, mouse anti-human TABM was diluted (1/2000), added to the plate and incubated for 90 minutes at 37° C., followed by sheep anti-mouse immunoglobulins (1/1000). The assay was then completed as previously described. The same ELISA conditions were used with non-bound organic molecules, except that pre-incubation of competing molecules with BA-TABM and serum was for 60 minutes.

EXAMPLE 28

The Serial Dilution of BA-TABM and its Interaction With BA-HSA and Other Haptens (FIG. 15)

A panel of different hapten preparations were diluted in carbonate buffer and plated at 250 ng/well (with respect to HSA) and incubated overnight at 4° C. A serial dilution of the patient serum and the BA-TABM isolated from this serum were tested against this panel. The serum and the BA-TABM were serially diluted in PBS: $1/200$–$1/3200$ and 500–31.25 ng/ml, respectively. One hundred μl were added to wells and incubated at 37° C. for 90 minutes. This was followed by mouse anti-TABM ($1/2000$) at 37° C. for 90 minutes and peroxidase conjugated sheep anti-mouse immunoglobulins ($1/1000$) and completed as described above.

EXAMPLE 29

Results

Neuropsychological Tests

The results of neuropsychological test are shown in Table 2.

Protein determination on BA-TABM

The purified BA-TABM were collected in a final volume of 10.5 ml from a serum volume equivalent to 88 ml. (Partially purified monoclonal antibody bound TABM were left aside for comparative studies). The final concentration of BA-TABM was 103 μg/ml. The serum concentration of BA-TABM was 12.3 μg/ml.

Detection of TABM in Serum Fractions

To confirm the presence of TABM at different stages of isolation from serum, the TABM were serially diluted and plated. Purified human IgG was also included as a control. FIG. 9 shows that TABM were detected using the monoclonal antibody (MG3C9-1A12) to human TABM as expected. A typical titration curve was obtained. TABM were present in both preparations after affinity isolation and there was no reaction with human IgG.

Detection of IgG and TABM in Samples

TABM was detected using the mouse anti-human TABM antibody in the BA-HSA, MG3C9-1A12 positive 'total' TABM and Cohn fraction III preparations serially diluted and coated directly onto ELISA plates. TABM was not detected in the purified IgG, HSA or BSA samples (FIG. 10).

An anti-human IgG reacted strongly with purified IgG and not to BSA or HSA. However, there was some binding to the 'total' TABM preparation and perhaps very weak binding to the BA-TABM and Cohn fraction III. This cross reaction could be due to a common epitope on human TABM and IgG (FIG. 10).

To Determine the Presence of Antigen Specific IgG in Serum and Different TABM Fractions Antigen specific serum IgG binding and serum derived TABM preparations were tested against different antigens. FIG. 11A shows that the patient serum has IgG antibody to the haptens BA-HSA and DNP-HSA. In the BA-TABM specific for BA-HSA there was no antigen specific IgG detected (FIG. 11C). In the MG3C9-1A12 positive 'total' TABM, there may be a little IgG present to BA-HSA and DNP-HSA (FIG. 11B). However, this could be due to cross-reaction by the polyclonal anti-human IgG antibody with TABM molecules.

Titration of BA-TABM Against BA-HSA

A typical titration curve was obtained for the interaction of serially diluted BA-TABM against the hapten BA-HSA. There was no reaction with the HSA control. Concentrations of specific TABM of less than 100 ng/mL were detectable in the assay (FIG. 12). A similar curve for the MG3C9-1A12 positive 'total' TABM eluted from the mouse anti-human TABM affinity column was obtained. TABM specific to BA-HSA were also detected in the patient serum at dilution of $1/3200$.

Inhibition Studies on Binding of BA-TABM to BA-HSA

The pre-incubation of BA-TABM to plate bound BA-HSA or DNP-HSA inhibited the binding of BA-TABM to plate bound BA-HSA in a dose dependent manner. A typical titration curve was obtained (FIG. 13). Weaker inhibition was also observed with pre-incubation of BA-TABM with Form-HSA and TMA-BSA.

Inhibition Studies on Binding of BA-TABM to BA-HSA and Free Chemicals

BA-TABM was pre-incubated with the hapten BA-HSA and the unbound molecules benzoic acid, para-aminobenzoic acid and toluene to see whether TABM recognize small chemical molecules unbound to protein.

There was inhibition of the BA-TABM binding to plate bound BA-HSA by the competing BA-HSA (FIG. 14). There was no inhibition of BA-TABM by the free molecules. Similar results were obtained when BA-TABM was pre-incubated with DNP-lysine and o-cresol.

Reaction of BA-TABM with a Panel of Haptens

Not only did BA-TABM bind strongly to BA-HSA, but also to DNP-HSA and OX-HSA with comparable titres. There was also weaker binding to Form-HSA and TMA-HSA (FIG. 15). Serum TABM also showed strong binding to DNP-HSA and OX-HSA.

Examples 30 to 38 relate to the clinical and immunological responses in subjects sensitive to solvents.

To evaluate the role of immunological responses in chemical sensitivity, the inventors measured serum IgG and TABM levels specific for an antigen produced by conjugating benzoic acid (a major metabolite of toluene) to human serum albumin (BA-HSA). These measurements were performed in a group of patients clinically documented to be sensitive to toluene and a control group. The results indicate an association between an elevation in serum TABM specific for BA-HSA and symptoms of chemical sensitivity and suggest that measurement of TABM against haptens may be of value in assessing patients sensitive to chemicals.

EXAMPLE 30

Patients

Twenty toluene sensitive patients were studied (elevan female, nine male). Their average age was 39.5 years). Some patients had a history of adverse reactions to chemicals, including solvents. Others were only subsequently shown to be sensitive to chemicals. Presenting symptoms including fatigue, irritability, headache, musculosketetal pain and poor concentration. Additional symptoms were soreness of the throat, sleep disturbance, post-nasal drip and nausea. More than half the patients had a history of occupational exposure to petroleum based chemicals, particularly to solvents (Table 3).

Patients were considered to be sensitive to the solvent toluene on the basis of developing symptoms and cognitive impairment following a controlled exposure. Using a specially designed tested booth, they were challenged with toluene at a concentration of 15 parts per million for 20 minutes. Symptoms before and subsequent to the chemical exposure were recorded.

Neurobehavioural tests were used to evaluate cognitive functioning pre and post challenge. The tests chosen were similar to those previously shown to be effective in documenting symptoms associated with solvent exposure (4). Focal length was an additional measurement included in the battery to assess the often cited subjective response by patients of blurred vision.

The battery provided estimates of immediate and delayed verbal memory recall (Babcock stories (5)), information processing times (Simple Reaction Time), concentration and attention (Letter Cancellation adapted from Lezak (5), and STROOP Colour Word (6)), psychomotor coordination (Symbol Digit (7)), and visual acuity (Focal Length). The results of pre versus post challenge data were analysed using the Wilcoxon matched pairs signed ranks test.

For purposes of analysing data, the patients were classified in two groups, according to the duration of chemical exposure:

Group 1 (7 patients)—exposure range 14 to 25 years;

Group 2 (10 patients)—exposure range up to 13 years;

Only patients with substantial chemical exposure were considered.

A second classification was made in terms of the type of chemical exposure incurred: Group A (6 patients) were principally exposed to heavy metals and solvents. Group B (8 patients) were exposed to other miscellaneous chemicals including hair dyes and pesticides.

Evaluation of chemical exposure was based on:
1. Work history since leaving school;
2. Accommodation history, including proximity to industry, airports, petrochemical plants, major traffic routes, crops and orchards and frequency of pest control spraying;
3. Hobbies and other activities: frequency of home renovation, furniture restoration, car detailing and repair; cottage industries were considered under this heading;
4. The occupation and hobbies of other family members were assessed as potential sources of exposure to chemicals.

The intensity and duration of exposure and type of chemical were considered in the assessment of exposure to chemicals.

EXAMPLE 31

Controls

Sixteen control subjects were studied (eight females and eight males). The average age was 32 years. Control subjects had no history of adverse reactions to chemicals and were reportedly in good health. They were not troubled by persistent symptoms such as fatigue, headache, musculoskeletal pain or poor concentration. The had no significant history of solvent exposure.

EXAMPLE 32

Serum Samples

Blood was collected by venipuncture, allowed to clot and centrifuged to collect the serum. Serum was stored frozen in multiple aliquots.

EXAMPLE 33

Anti-human TABM Antiserum (R28)

The R28 antiserum is a polyclonal rabbit antiserum directed against human T-cell derived antigen specific binding molecules (TABM). It was prepared by isolating TABM from human serum by ammonium sulphate precipitation and ion exchange chromatography (8). Any contaminating immunoglobulin and albumin were removed by passage through an anti-human immunoglobulin and an anti-human albumin affinity column. The rabbit antiserum that was raised to TABM was also passed through a human immunoglobulin and albumin affinity columns to remove antibodies that could react with human IgG and albumin. There is no cross reactivity of R28 antibody with human IgG or IgM or albumin as tested by ELISA.

EXAMPLE 34

Antigen

In these experiments, the inventors used para-amino benzoic acid that was conjugated to human serum albumin (BA-HSA) as antigen (Immunosciences Lab Inc, Los Angeles) and was made by the diazotization method (9).

EXAMPLE 35

ELISA Assay

The BA-HSA was diluted in 0.06M carbonate buffer, pH 9.6 and 100 microliters (500 ng) dispensed into wells of NUNC Maxisorp ELISA plates (Nunc, Denmark). The plates were incubated overnight at 4° C. Following five washed with PBS-0.05% v/v Tween-20 (PBS-Tw), the plates were blocked with 200 $\mu$l of 1% w/v gelatin in carbonate buffer for 75 min at 37° C. After 5 washes, 100 $\mu$l of serum diluted 1/500 in PBS-Tw 1% w/v gelatin for determination of IgG or 1/20 for TABM was added to the wells and incubated for 90 min at 37° C. After washing the plates, 100 $\mu$l of 1/3000 sheep anti-human IgG-peroxidase (Silenus Laboratories, Australia) diluted in PBS-Tw 1% w/v gelatin was added per well and incubated for 90 min at 37° C. The colour reaction was generated by adding 100 $\mu$l of 3,3',5,5'-tetramethylbenzidine (TMB) substrate (KPL, Gaithersberg, Md.) per well and incubating at room temperature for the colour to develop. The reaction was stopped with 100 $\mu$l of 2M $H_2SO_4$. For TABM, rabbit anti-human TABM (R28 serum) was diluted 1/300, added to the wells and incubated for 90 min at 37° C. This was followed by 100 $\mu$l of 1/500 sheep anti-rabbit IgG peroxidase (Silenus Laboratories, Australia). After 90 min at 37° C. the reaction was developed and stopped as above. Control antigens included gelatin and HSA plated at 500 ng/well. All incubated were carried out in a humidified box. Plates were then read at 450 nm. All samples were tested in duplicate.

EXAMPLE 36

Standards

The ELISA assays were first run to determine optimum concentrations of all reagents, followed by evaluation of some serum samples. Serum samples with high activity (OD) were pooled (equal volumes), aliquoted and frozen. For each ELISA assay a fresh ampoule was serially diluted and used as an assay standard. Arbitrary units were assigned to each standard serum pool as follows: IgG to BA-HSA 100,000 U/ml; and TABM to BA-HSA 10,000 U/ml. Serial (½) dilutions of pooled standard serum were: IgG, 1/200–1/3200; and TABM, 1/20–1/640. The units of activity of each serum sample were determined after plotting standard curves using the Beckman Immunofit EIA/RIA analysis program (v 3.0).

EXAMPLE 37

Competitive Inhibition ELISA for Antigen Specificity

To determine the antigen specificity of a serum toward the BA-HSA hapten, a competitive ELISA was used. The ELISA plate was coated with BA-HSA (250 ng/well) in carbonate buffer overnight at 4° C. A serum from a patient with high levels of (R28+) TABM to BA-HSA was used at a dilution of 1/200. The competing antigens or haptens were serially diluted (½) in the serum to give a range equivalent to 5000–312.5 per well. The antigens and haptens tested included human serum albumin (HSA), bovine serum albumin (BSA), BA-HSA, trinitrophenol conjugated to BSA (TNP-BSA) and formaldehyde conjugated to HSA (F-HSA). The serum and antigen/hapten mixtures were first preincubated for 30 min at 37° C. before adding to the BA-HSA coated ELISA plate. The plate was then incubated for 60 min at 37° C. After washing R28 was diluted (1/400), added to the plate and incubated for 90 min at 37° C. The assay was then completed as previously described.

EXAMPLE 38

Results

Clinical Observations

Details on the patient group are listed in Table 3. Disability was clinically rated as mild, moderate or severe depending on severity of symptoms and interference with lifestyle, including whether employed or not. Severely affected patients were unable to work and those moderately affected required a major change in their work environment to remain employed. The severity of the reaction to toluene was rated 0 to +++. Typical symptoms produced on toluene challenge included fatigue, poor concentration, headache and muscle pains.

Neuropsychological Testing

The results of neuropsychological testing of patients are shown in Table 4. The test subjects showed a significant deterioration in performance post challenge on immediate and delayed memory tests (FIGS. 16 and 17) and, less notably, on digit-symbol (FIG. 18) and letter cancellation error tests (FIG. 19).

IgG Assay

There was no significant difference (p=0.535) in serum levels of antigen specific IgG to the hapten-HSA antigen (BA-HSA) between controls and patients (FIG. 20). However, in both groups a number of individuals showed low levels of IgG to the antigen.

TABM Assay

The patient group showed higher levels of TABM to the BA-HSA antigen than controls (FIG. 21), p=0.002. Out of a total of 36 assays on patients and controls, the 12 highest values for TABM were all from the patient group. As mentioned, the R28 antibody detects human TABM that bind antigen specifically.

The specificity of the TABM to BA-HSA was also tested. A serum positive for TABM specific to BA-HSA did not show binding to HSA, BSA, F-HSA, TNP-BSA, or the cows milk protein β-lactoglobulin as detected using the R28 antiserum. In a competitive binding ELISA, pre-incubation of the patient serum with BA-HSA inhibit binding to BA-HSA bound to the plate wells. The inhibition occurred in a dose dependent manner (FIG. 24). No inhibition of serum TABM binding to BA-HSA on the well was observed when the serum was pre-incubated with HSA, BSA, F-HSA or TNP-HSA. In these experiments the R28 antiserum was also treated to remove any rabbit IgG to BA-HSA by passage through a BA-HSA affinity column.

Association Between TABM Level and Clinical Severity

The TABM level correlated with clinical assessment of disability, p=0.008.

Comparison of TABM Score and Severity of Reaction to Toluene

There was no correlation between the severity of symptoms produced by toluene exposure and the TABM score, p=613.

Comparison of TABM Level and Changes in Performance on Neuropsychological Tests

Statistical analysis showed significant correlations between TABM and changes in both focal length and in STROOP (colour word) post challenge (Table 5 and FIG. 22). There was no correlation between TABM levels and other neuropsychological tests.

Comparison of TABM Levels and Chemical Exposure

TABM levels were higher in subjects with a longer history of chemical exposure (Group 1) p=0.0125 (FIG. 23). No other differences in TABM levels were evident in comparisons between the groups.

Comparison of Neuropsychological Tests with Groupings Related to Chemical Exposure Subjects with a longer history of exposure (Group 1) showed a greater deterioration of the STROOP (Colour Word) Test (p=0.017) indicating greater attention difficulties. Subjects with a shorter history of exposure (Group 2) showed a greater deterioration in performance on the Prose Memory (delayed) Score (p=0.017 ) and the Digit Symbol Test (p=0.039). The latter test assesses psychomotor co-ordination (Table 6). Subjects with a history of exposure to heavy metals and/or solvents (Group A) had a significantly lower Prose Memory (immediate) Score (p=0215) and shorter reaction time (p=0.0441) prior to their challenge, as compared to Group B (Table 7).

SUMMARY

Twenty patients were demonstrated to be sensitive to the solvent toluene when exposed to this chemical at a concentration of 15 parts per million for 20 minutes. Neuropsychological tests on patients assessed before and after toluene exposure showed impairment in cognitive functioning, with a deterioration in short and long term memory and psychomotor coordination. Total IgG and T-cell antigen binding molecules (TABM) were measured against an antigen prepared by conjugating para-amino benzoic acid to human serum albumin (BA-HSA) in the 20 patients and 16 controls. There was no significant difference in the IgG levels to the antigen, but the levels of TABM against the BA-HSA were significantly elevated in those subjects sensitive to toluene. There was no significant associations between the TABM levels and, a) poorer performance on the STROOP (colour word) test, b) shift in focal length after toluene exposure, c) clinical assessment of disability and d) longer history of chemical exposure. The measure of TABM against chemical haptens may be of value in assessing patients sensitive to chemicals.

Examples 39 to 47 relate to the measurement of TABM and IgG to mannan from *Candida albicans* in patients with recurrent thrush.

Numerous studies have indicated the importance of cell mediated immunity (Th1 response) in protection against *Candida albicans* infection, particularly at mucosal surfaces. This type of response also appears important in the prevention of vulvo-vaginal candidiasis. In patients susceptible to this type of Candida infection, studies indicate a local impairment of cell-mediated immunity to *Candida albicans,* even though the Th1 immune response to the yeast appears systemically intact.

*Candida albicans* is associated with numerous antigens. Certain antigens appear important in stimulating protective cell mediated immunity. Other antigens, particularly the carbohydrate mannan, are thought to be implicated in immune suppression.

The monoclonal antibody (MG3C9-1A12) described in Examples 1–19 is specific for human TABM. This antibody does not react with immunoglobulin G or albumin. An ELISA assay has been developed using the monoclonal antibody to measure TABM specific to whole Candida extract and to mannan prepared from *Candida albicans* using the Peat and CTAB (cetryltrimethylammonium bromide) methods. Serum levels of antigen specific TABM (and IgG) were measured in patients susceptible to vulvovaginal candidiasis and a control group.

EXAMPLE 39

Subjects

Women attending the Sexual Health Centre, Melbourne, Victoria and a family planning clinic were included in the study.

Controls had not had thrush for one or more years and thrush was not an ongoing problem.

EXAMPLE 40

Serum Samples

Institutional ethics approval was obtained for the study. Informed consent from the blood donors was obtained.

Ten milliliters of blood were collected by venipuncture into vacutainer tubes. The blood was allowed to clot at room temperature and centrifuged to recover the serum. The serum was frozen at −20° C. in multiple aliquots of 0.5–1 mL. A fresh aliquot of serum was used for each assay.

EXAMPLE 41

Candida Antigens

Two different preparations of mannan derived from *C. albicans* were used. The cetryltrimethylammonium bromide (CTAB) method involves complexing with the mannan which is subsequently isolated. Preparation of mannan (PEAT) involves degrading under alkaline conditions and precipitation with Fehling's solution. The mannans are a highly branched glycoprotein containing essentially mannose and less than 10% of the molecular weight is protein.

EXAMPLE 42

Monoclonal Antibody to Human TABM

The mouse monoclonal antibody (MG3C9-1A12) specifically recognises human TABM (see Examples 1–19). The monoclonal antibody preparation used in this study was purified from culture supernatant (25 fold) using Protein-G sepharose (Pharmacia) and is stored in PBS with sodium azide at 4° C.

EXAMPLE 43

ELISA Assays

Extensive ELISA experiments were carried out to determine the optimum conditions for the measurement of TABM and IgG levels to each of the Candida antigens.

EXAMPLE 44

Serum Standard for ELISA Assays

Equal volumes of serum from six patients with recurrent thrush were pooled, aliquoted in 0.2 ml volumes and stored frozen until required. The serum pool was serially diluted by ½ in PBS-Tw-1% w/w gelatin (PTG) for IgG and in PBS for TABM. A standard curve was generated after plotting optical density (OD) against arbitrary 'Units/ml' with respect to the dilution made. The dilution range of the serum standard and the number of arbitrary units assigned to the undiluted serum for each ELISA assay is as follows: TABM to CTAB and PEAT mannan,1/20–1/320 and 1,000 units/ml; TABM to Hollister-Stier skin test antigen, 1/25–1/3,200 and 5,000 Units/ml; IgG to CTAB and PEAT mannans,1/500–1/128,000 and $10^6$ Units/ml; and IgG to Hollister-Stier skin test antigen, 1/500–1/64,000 and $10^6$ Units/mL. All dilutions of the standard and samples were tested in duplicate. Each dilution was assigned the appropriate number of 'units/ml'. The units of activity of each serum sample were determined after plotting standard curves using the Beckman Immunofit EIA/RIA analysis program (v 3.0).

EXAMPLE 45

ELISA for Detection of Human Immunoglobulin G Specific to *Candida albicans* CTAB and PEAT Mannans The mannan preparations were diluted in PBS pH 7.4 and coated overnight at 37° C. on Falcon (Becton Dickinson, N.J.) 'pro-bind' plates. After washing with PBS-0.05% v/v Tween 20, (PBS-T), the plates were blocked with 1% w/v gelatin in carbonate buffer pH 9.6 for 90 min at 37° C. and rewashed. The standard serum pool was serially diluted as above. Serum samples were diluted 1/5000 in PTG and 100 ul added per well in duplicate and incubated for 90 min at 37° C. The plates were washed and 100 µl affinity purified peroxidase conjugated sheep anti-human immunoglobulins (Silenus, Australia) was added (1/10,000) and incubated for 90 min at 37° C. Following washing, 100 µl 3,3',5,5'-tetramethylbenzidine hydrochloride (TMB) substrate (KPL, Gaithersburg, Md.) was added and the reaction allowed to procede at room temperature until an optical density (O.D.) of approximately 2 was obtained. The reaction was stopped with 2M $H_2SO_4$ and the plates read at 450 nm.

EXAMPLE 46

ELISA for Detection of Human Immunoglobulin G Specific to Hollister-Stier *Candida albicans* Skin Test Antigen The antigen preparation was diluted in 0.06M carbonate buffer pH 9.6 and coated overnight at 4° C. on Costar (Cambridge, Mass.) E.I.A. plates. After washing with PBS-T, the plates were blocked with 1% w/v gelatin in carbonate buffer for 90 min at 37° C. and rewashed. The serum samples were diluted 1/2000 in PTG and 100 µl plated per well in duplicate and incubated for 90 min at 37° C. The plates were washed and 100 µl affinity purified peroxidase conjugated sheep anti-human immunoglobulins (1/5,000 in PTG) was added and incubated for 90 min at 37° C. Following washing, substrate was added and the reaction completed as above.

EXAMPLE 47

ELISA for Detection of Human TABM Specific to *Candida albicans* CTAB and PEAT Mannans

*Candida albicans* mannans were bound to Falcon ELISA plates as above. The plates were blocked with 1% w/v human serum albumin (HSA) in PBS and washed. Serum samples were tested at 1/50 dilution in PBS and 100 µl added per well and incubated. Protein-G purified mouse monoclonal anti-human TABM antibody was diluted 1/1,000 in PTG, and 100 μl added to the wells, incubated and washed. One hundred μl of affinity purified sheep anti-mouse immunoglobulins (Silenus, Australia) diluted 1/500 in PTG was added and incubated. The reaction was completed as above.

EXAMPLE 48

ELISA for Detection of Human TABM Specific for Hollister-Stier Candida Skin Test Antigen The antigen preparation was diluted in 0.06M carbonate buffer pH 9.6 and coated overnight at 4° C. on Costar E.I.A. plates. After washing with PBS-T, plates were blocked with 1% w/v gelatin in carbonate. Serum samples were tested at 1/200 dilution in PBS. Protein-G purified mouse monoclonal anti-human TABM antibody was diluted 1/1,000 in PTG, added to the wells, incubated and washed. An affinity purified sheep anti-mouse immunoglobulins was diluted 1/500 in PTG. The reaction was completed as above.

EXAMPLE 49

Results
Immunoglobulin G Levels to *Candida albicans* Antigens

A comparison of IgG levels between patients and controls to *C. albicans* CTAB and PEAT mannans showed a significant difference (P=0.048 and 0.032, respectively). There was no significant difference in IgG levels between patients and controls to the Hollister-Stier skin test preparation (P=0.0791).

TABM Levels to *Candida albicans* Antigens

TABM levels between patients and controls were significantly different to the CTAB mannan preparation (P=0.0291). There was no significant difference in levels to the PEAT mannan (P=0.0721) nor to the Hollister-Stier preparation (P=0.2166) between patients and controls.

Examples 50 to 57 relate to the action of TABM on sensory nerve endings.

It has been proposed that chemical sensitivity is due to the action of specific chemicals on afferent nerves. This could produce neurogenic information in tissues exposed to chemicals. The central nervous system and other tissues could also be affected by the relay of neural signals to the central nervous system and the antidromic propagation along other sensory nerves. The latter process is described as neurogenic switching.

The difficulty with this theory is that although many chemicals may stimulate afferent nerves by acting on irritant receptors, an additional action on nerve endings is required to explain the effects reported by chemically sensitive patients. Tolerance normally develops to the effects of chemical irritants. It has been further proposed that in chemically sensitive patients, there is mucosal injury, allowing greater access of chemicals to sensory nerve endings. Where chemical sensitivity is reported after a high chemical exposure, it is suggested that the mucosal barrier is disrupted. Although such an event perhaps causes adverse reactions to chemicals during the period immediately following a high chemical exposure, it seems unlikely to account for the long term problems experienced by chemically sensitive patients.

Immune sensitisation to chemicals is another possible consequence of chemical exposure. This process could result in the local release of inflammatory mediators and cytokines. Cytokines may act on sensory nerve endings with propagation of neural signals to the central nervous system. In the case of interleukin-1, the hypothalamus and centres involving the regulation of mood and pain are affected by this process.

In the following Examples, the inventors show that the cytokine TGF-β is associated with TABM purified from the serum of a patient sensitive to the solvent toluene. These TABM are specific to benzoic acid conjugated to human serum albumin (BA-HSA), benzoic acid being an important metabolite of toluene. It is further demonstrated that both TGF-β and the TABM enhance the release of neuropeptides from sensory nerves in a dose dependent manner and in both cases the effect is blocked by anti-TGF-β antibody. When the antigen BA-HSA is added, the effect of TABM may be enhanced or reduced, depending on the ratio between TABM and antigen.

This study may explain:

(a) how neurogenic inflammation could be produced in chemically sensitive patients with possible effects on the central nervous system; and (b) how the effects on sensory nerves may vary with chemical concentration, but not in a dose dependent manner.

A vacuum-induced blister model in the footpad of anaesthetised rats is used to induce an inflammatory response in naive skin by (a) electrical stimulation (ES) of the distal end of the cut sciatic nerve at 20 v, 5 Hz, 2 ms for 1 min or (b) superfusion of the sensory neuropeptide; substance P (SP) over the blister base.

EXAMPLE 50

Animals

Male outbred Sprague-Dawley rats with an average weight of 250–300 gm were used (n=6–8 per group). Anaesthesia was induced with pentobarbitone sodium (Nembutal, 60 mg/kg, i.p.). To ensure that rats remained under a constant stage of surgical anaesthesia additional doses (15 mg/kg) were administered during the experiment. The absence of an eyelash reflex was used as an indication of the level of unconciousness. At the end of the experiment, animals were killed by barbituate overdose (100 mg/kg).

EXAMPLE 51

Blister Induction and Experimental Set Up

A blister was induced on the hind footpad on the anaesthetised rat by applying a vacuum pressure of −40 kPa to the glabrous skin for approximately 30 mins, using a metal suction cap heated to 40° C. by an attached heating element.

When a blister was established, the surface epithelium was removed and a perspex chamber with inlet and outlet ports was fixed over the blister base. Perfusion of the drugs over the blister was maintained at 4 ml/h by a peristaltic pump (Microperpex S, LKB, Sweden). Both perfusion and body temperature were kept at 37° C.

An initial 15 min equilibration with Ringer's solution (NaCl 9.0 g, KCl 0.42 g, $CaCl_2$ 0.48 g, $NaHCO_3$ 0.2 g in 1000 ml $dH_2O$) was allowed before each experiment, during which time a stable baseline was established.

EXAMPLE 52

Antidromic Electrical Stimulation (for TGF-β)

The right sciatic nerve in the mid-thigh region of the anaesthetised rat was dissected free and cut as proximally as possible. The distal portion of the cut nerve was placed over bipolar platinum electrodes and immersed in liquid paraffin warmed to 37° C. and contained in a bath that was formed by raising the skin flaps of the wound. The distal end of the sciatic nerve was stimulated with a Grass S48 stimulator at 20 V, 5 Hz, 0.5 ms square waves for 1 min. These parameters were previously shown to stimulate sensory nerves with subsequent release of sensory peptides.

EXAMPLE 53

Peptide Perfusion

The experimental protocol consisted of a pre-stimulation period with Ringer's solution (two 10 min periods), followed by a 10 min perfusion of sodium nitroprusside (SNP) at 100 µM. The latter is a direct smooth muscle vasodilator that is used in the experiment to control for the variability in smooth muscle reactivity between rats. This was followed by two 10 min periods with Ringer's solution to re-stabilise the baseline. A three 10 min stimulation periods with either SP (1 µM) alone or in the presence of TABM (0.1 or 1.0 µg/ml).

Finally, there was a 10 min post-stimulation period with perfusion of Ringer's solution. TABM were perfused over the blister base during the second 10 min of re-establisation periods as well as during the three stimulation periods. In some experiments, TABM were perfused at 0.1 µg/ml for 20 min.

In experiments where the effect of antigen was tested, antigen (0.001 µg) was perfused for 10 min prior to and together with TABM and SP.

EXAMPLE 54

Measurement of Local Blood Flow

For measurement of local blood flow, a probe attached to a laser Doppler flowmeter (Periflux, PF2B, Perimed, Sweden) was inserted vertically through a third port in the perspex chamber above the blister base. Relative blood flow was recorded over time on a chart recorder and measured as the surface area under the response curve in $cm^2$ using a digital planimeter.

EXAMPLE 55

Materials

Substance P (Auspep, Australia) were dissolved in Ringer's solution. All other common chemicals and solvents were of analytical grade from various commercial sources.

EXAMPLE 56

Expression of Data and Statistical Analysis

Vasodilator responses were measured as the area under the response curve ($cm^2$) using a digital planimeter (Tamaya, Japan). For vascular responses to ES the area was measured for 20 min following stimulation. For SP response which is characterised by gradual tachyphylaxis, this was the area during the 30 min perfusion. For SNP responses that are characterised by maintained responses, this was the area under the curve during 10 min of perfusion. Results are expressed as mean±SEM. Statistical analyses were performed using one way analysis of variance (ANOVA) with a priori planned contrasts. SNP responses were used as a covariate. Type 1 error was set at $\alpha=0.05$ and p value of 0.05 was considered significant.

EXAMPLE 57

Results

The Vascular Response to ES in Capsaicin Pretreated Rats

Neonatal capsaicin pretreatment was conducted when rats were 3–4 days old. A single subcutaneous injection of 50 mg/kg capsaicin causes selective destruction of 80% of sensory C-fibres, these being termed capsaicin-pretreated rats. These rats were utilised to investigate the role of sensory nerves in different physiological responses. When the vascular response to ES was examined in capsaicin-pretreated rats, the response profile was characterised by quicker tachyphylaxis compared to control and the area of the response was only 11.7±1.1 $cm^2$.

Effect of TGF-β on the Vascular Response to Antidromic ES of the Sciatic Nerve

Electrical stimulation of the cut/exposed sciatic nerve resulted in an increase in local blood flow in base of blisters induced in naive skin. The increase was maintained for a period of over 20 minutes. The area under the response curve for 20 minutes was 18.1±0.9 $cm^2$. TGF-β (10 pg/ml) perfused over the blister base for 10 min prior to ES as well as during the post stimulation period, did not alter the baseline but enhanced the response from 18.1±0.9 $cm^2$ to 31.44±3.2 $cm^2$.

Effect of TGF-β on the Vascular Response to ES in Capsaicin-pretreated Rats

When TGF-β was used to 10 pg/ml it did not alter the baseline in these rats and it also had no effect on a subsequent response to ES. The response to ES in capsaicin-pretreated rats in presence of TGF-β was 12.1±1.0 compared to a ES response in the absence of TGF-β 11.7±1.1 $cm^2$. The fact that TGF-β at the concentration of 10 pg/ml did not alter the response to ES in capsaicin-pretreated rats while it significantly enhanced the response in control rats suggests that the response to TGF-β at this concentration is mediated via an action on sensory nerves.

Effect of TABM on the Vascular Response to SP, Enhancement by Antigen

Perfusion of SP (1 µM) alone over the base of a blister induced in naive skin resulted in a vasodilatation response that reached its maximum within 3–5 min of initiation of perfusion. The response gradually diminished and reached the basal level in 15–20 min despite continuous perfusion of SP for 30 min. Perfusion of TABM (0.1 & 1.0 µg/ml) over the blister base prior to and together with SP (1 µM) significantly enhanced the vasodilatation response to SP in a dose dependent manner from 44.1±3.9 $cm^2$ to 63.4±4.8 $cm^2$ & 84.5±4.6 $cm^2$, respectively. TABM alone had no effect on basal blood flow.

Effect of Duration of Exposure to TABM on the Vascular Response to SP

In another experiment TABM was perfused at 0.1 µg/ml either for 10 or 20 min over the blister base prior to and then together with SP (1 µM). Perfusion of TABM for 10 min enhanced the response to SP from 44.1±3.9 $cm^2$ to 63.4±4.8 $cm^2$. On the other hand, prolonged exposure of the blister base to TABM (20 min) greatly enhanced the response to 90.6±5.2 $cm^2$. This degree of enhancement is equivalent to that induced by the higher dose (1.0 µg/ml) which increased the response to 84.5±4.6 $cm^2$.

Effect of Antigen Pre-exposure on the Effect of TABM

Pretreatment with antigen (0.001 µg/ml for 20 min) on the inflammatory response to SP. Anti-TGF-β antibody reduced the response from 90.6±5.2 $cm^2$ to 49.5±3.8 $cm^2$.

Effect of anti-TGFβ antibody on the effect of TABM on the inflammatory response to SP Pretreatment with anti-TGFβ antibody (0.1 µg/ml) significantly inhibited the enhancing effect of TABM (0.1 µg/ml for 20 min) on the inflammatory response to SP. Anti-TGFβ antibody reduced the response from 90.6±5.2 $cm^2$ to 49.5±3.8 $cm^2$.

Examples 58 to 71 relate to the production of serum immunoglobulins and TABM specific for cow's milk antigens in adults intolerant to cow's milk.

While IgE-mediated reactions to foods are reasonably well understood, the role of adverse reactions to foods in clinical problems such as migraine, irritable bowel syndrome and the chronic fatigue syndrome remains controversial. Although a number of studies have reported the importance of diet in these disorders (10–16), other studies are in disagreement (17,18). These differing results may be due to methodological variations in the studies, and to difficulties in symptom assessment.

There have been a number of explanations advanced to explain delayed reactions to foods including pharmacological, psychosomatic and immunological reasons.

Although IgE antibody levels in various food stuffs have been determined in a number of disorders such as migraine (12), the measurement of IgG antibodies has been limited. Relatively little work has been done in measuring total IgG and IgG subclasses against common foods in adults (9). Also, there are difficulties in the interpretation of such data as it is unclear whether the production of IgG antibodies to foods is a physiological response.

There is little information available concerning the role of a T lymphocyte response to food antigens.

In the following Examples, the inventors measured serum IgG, IgG subclasses (IgG1, IgG2, IgG3, IgG4), IgE and TABM specific for three principal antigenic milk proteins; β-lactoglobulin, α-lactalbumin and casein in milk-intolerant patients and controls. TABM-specific for β-lactoglobulin (BL-TABM) in a milk-intolerant patient's serum were purified by affinity for β-lactoglobulin were found to be Mr 28,000, 46,000 polypeptides (after reduced) that are not recognized by antibodies to human immunologlobulin chains. Moreover, the non-denatured antigen affinity-purified TABM are associated with TGF-β1 and TGF-β2.

EXAMPLES

Patients

Fifteen milk-intolerant patients were studied (13 female, 2 male). The average age was 39.5 years. Patents had presented with a range of symptoms including abdominal pain, diarrhea, headache, musculoskeletal pain and fatigue. Two subjects had severe migraine. Milk intolerance was diagnosed on the basis of the development of symptoms after open challenge with half a liter of milk following symptom improvement on elimination diet. Patients were observed for up to 8 hours after the challenge and symptoms recorded for two days. Symptoms reported following the challenge and symptoms included headache, fatigue and musculoskeletal pain (Table 8). Patients had not ingested milk products for at least two weeks both prior to the milk challenge and when blood samples were taken.

The patient from whom blood was obtained to purify TABM was clinically intolerant to cow's milk. The ingestion of 250 ml of cow's milk produced numerous symptoms over the following 24–48 hours. Symptoms were noted within 1–2 hours of milk ingestion and included abdominal distension, abdominal pain, diarrhea, fatigue and agitation. Difficulty in concentration, mental unrest and sleep disturbance were also observed to occur. A skin prick test for cow's milk was negative and a lactose tolerance test was normal. The patient had presented with fatigue, sleep disturbance, headache, poor concentration and postnasal drip. With the use of elimination diet, she was also found to be intolerant to a number of other foods.

All subjects were skin prick-tested with the Hollister-Stier (Miles Inc., Elkhart, Ind.) whole cow's milk antigen.

EXAMPLE 59

Controls

Eleven control subjects were studied (9 female and 2 male). The average age was 37 years. Control subjects had negative skin prick tests to Hollister-Stier whole cow's milk extract and had no history of food intolerance, particularly to milk or cheese. Control subjects were in good health and had no history of migraine or of functional gastrointestinal symptoms. Controls had not ingested milk during the 3–4 hour period before blood samples were taken, and were not challenged with cow's milk.

EXAMPLE 60

Serum Samples

Blood samples were collected from milk intolerant patients and controls. The serum was collected and stored frozen at −70° C. in 0.5–1 ml aliquots. A fresh aliquot of serum was used for each ELISA assay.

EXAMPLE 61

Antigens

β-lactoglobulin (BL) (3 times crystallized and lyophilized), α-lactalbumin (AL) and α-s-casein (CA) were purchased from Sigma Chemical Co., St. Louis, Mo. They were all made up at 2 mg/ml in PBS pH 7.4 and stored frozen in aliquots at −20° C. Horse serum (HS) (Commonwealth Serum Laboratories, Melbourne, Australia) was used as a non-milk control antigen. A similar amount to the milk antigens was coated onto ELISA plates. HS was also present in the sample and antibody diluent.

EXAMPLE 62

Anti-TABM Antiserum

Polyclonal (rabbit) antisera (R28, R30) specific for human TABM were prepared against TABM from human serum isolated by ammonium sulphate precipitation and ion exchange chromatography (8). The antisera were absorbed with fetal calf serum, immunoglobulin IgG and IgM beads and albumin-sepharose beads to remove antibodies that could react with human immunoglobulins, albumin or bovine serum. There is no cross reactivity of the absorbed R28, or R30 antibody with human IgG, IgM, human or bovine albumin as tested by ELISA (8). The R28 antibody has been shown to bind to TABM specific for tetanus toxoid, and T-cell proteins (immunoblot), but does not bind to T lymphocyte membranes or B-cell proteins (8).

EXAMPLE 63

Antigen Capture Enzyme Linked Immunosorbent Assay (AG-ELISA)

Ag-ELISA was performed by a modification of that previously described (20–22). Maxisorp ELISA plates (Nunc, Denmark) were coated with 500 ng of milk protein in 100 µl of 0.06M carbonate buffer pH 9.6 overnight at 4° C. The plates were washed 5 times with PBS (pH 7.2) −0.05% v/v Tween-20 (PBS-Tw) and blocked with 200 µl per well of 4% v/v horse serum (HS) in carbonate buffer for 60 minutes at 37° C. The plates were washed and 100 µl of the serum samples diluted in PBS-Tw-4% v/v HS (anti-IgG, 1/1,000; IgG1, 1/100; IgG2, 1/100; IgG3, 1/100; IgG4, 1/200; IgE, 1/10; and TABM, 1/5) were added to the appropriate wells and incubated for 90 minutes at 37° C. The plates were washed and 100 µl of the primary antibody [rabbit anti-human IgG (DAKO, Denmark), 1/2, 500; mouse monoclonal anti-human IgG1, anti IgG2, 1/1,600; anti-IgG3, 1/800; anti-IgG4, 1/3200 (Nordic, Netherlands); rabbit anti-human IgE (Behring, Germany), 1/4,000; and R28 rabbi anti-human TABM 1/300] diluted in PBS-Tw-4% v/v HS were added to the appropriate wells and incubated for 90 minutes at 37° C. After washing, the enzyme conjugates, rabbit anti-mouse IgG peroxidase 1/400 (DAKO, Denmark) or sheep anti-rabbit IgG peroxidase, 1/400 (Silenus, Australia) were diluted in PBS Tw-4% v/v HS and 100 µl added to the wells. The plates were incubated at 37° C. for 90 minutes. After washing, 100 µl 3,3', 5,5'-tetramethyl benzidine (TMB) substrate (KPL, Gaithersburg, Md.)d was added to the wells and incubated at room temperature. The color reaction was stopped with 100 µl $H_2SO_4$ when the optical density (O.D.) of approximately 2, for immunmoglobulin levels and 0.5 for TABM was reached. Plates were read at 450 nm. All samples were tested in duplicate and the mean O.D. was used for all calculations.

EXAMPLE 64

ELISA Standards—Antibodies to Cow's Milk Proteins

A standard curve was produced using a serum pool from 50 children with at least a positive RAST to milk assessed using Kallestad antigen discs and the Kallestad Allercoat EAST kit (Sanofi Diagnostics Pasteur, Inc.). The serum pool was aliquoted and stored frozen at −70° C. For each assay, a fresh aliquot was thawed and serially diluted by ½. The undiluted pool was assigned an arbitrary number of units for each of the antibody assays as follows: IgG, $10^6$; IgG1, $10^5$; IgG2, $10^5$; IgG3, $10^5$; IgG4, $10^5$; and IgE, $10^4$. The standard dilution ranges for each assay were: IgG, 1/500–1/6,400; IgG1, 1/100–1/6,400; IgG2, 1/100–1/6,400; IgGe, 1/50–1/3,200; IgG4, 1/100–1/6,400; and IgE, 1/10–1/640.

EXAMPLE 65

ELISA Standards—TABM to Cow's Milk Proteins

Three separate serum pools were prepared as standards to determine TABM levels to β-lactoglobulin, α-lactalbumin and casein. The undiluted serum pools were assigned 100, 500, 1000 units/ml, respectively. Each of the standard serum pools consisted of an equal volume of serum from three patients that had a high TABM response to the particular antigen. The standards were serially diluted (½) from ⅕–1/320, and the appropriate number of units were assigned to correspond to the serially diluted standard. Patient serum samples were tested at a dilution of ⅕. This allowed for plotting a standard curve with arbitrary units (rather than a dilution value) against the O.D. The sample O.D. values were manually read off the standard curves as arbitrary units. Comparison of groups were performed using the Mann-Whitney U Test.

EXAMPLE 66

ELISA for Tumor Necrosis Factor

A sandwich ELISA method was used to determine TNF-α levels in culture supernatants. ELISA plates (Costar, Cambridge, Mass.) were coated overnight at 4° C. with a purified polyclonal goat anti-TNF-α capture antibody (R&D Systems, MN) in 0.06 M carbonate buffer pH 9.6. The plate was washed 5 times with PBS-0.05% v/v Tween (PBS-Tw) and blocked with 200 µl of 1% w/v gelatin. Recombinant TNF-α (NIBSC Hertfordshire, UK) was used as the standard and serially diluted by ½ from 2000 to 0.98 pg/ml. All standards and samples were tested in duplicate and incubated for 90 minutes at 37° C., followed by 5 washes with PBS+TW. Standards and samples (tested in duplicate) were incubated for 90 minutes at 37° C., and the plate was washed 5 times with PBS-Tw. The mouse monoclonal second antibody (R&D Systems, MN) was applied and incubated for 90 minutes at 37° C., and the plate washed 5 times. A peroxidase-conjugated sheep anti-mouse IgG antibody (Silenus, Australia) was applied for 90 minutes at 37° C. After washing, TMB was added. The reaction was incubated at room temperature unit an O.D. of approximately 2was reached and stopped with 2 M $H_2SO_4$. Plates were read at 450 nm, and the data analyzed using the Beckman Immunofit EIA/RIA analysis program (v 3.0).

EXAMPLE 67

ELISA Inhibition Assay (EIA) for TGF-β

Microtiter trays were coated 16 hours at room temperature with 10 ng/well TGF-β1, 2 or 3 peptides (Santa Cruz Biotechnologies, Santa Cruz, Calif.). One hundred µl of 1:1000 dilution of anti-TGF-β1, 2 or 3 was mixed with 10 µl wash buffer, 0.25–4 ng TGF-β1, 2 or 3 peptide. respectively, or 10–20 µl BL-TABM. After 1.5 hours, the trays were washed and a 1:1000 dilution of AP-goat anti-rabbit IgG added. After 1.5 hours at 37° C., the plates were washed and p-nitrophenyl phosphate substrate added, the optical density of each was determined after 15 minutes incubation. The percent inhibition of the antibody binding to solid phase TGF-β peptide by soluble peptide or BL-TABM was determined by $$\% \text{ inhibition} = \frac{\text{O.D. (A405)} + \text{soluble peptide or BL-TABM}}{\text{O.D. (A405)} + 10 \text{ µl wash buffer}} \times 100$$

A standard curve based on percent inhibition by 0.25–4 ng TGF-β peptide was prepared; and to compute ng of TGF-β in a sample, the percent inhibition obtained with samples was compared to that obtained with soluble antigenic peptides. The moles of inhibitory peptide was then computed as moles of TGF-β protein. Preliminary studies in this assay have demonstrated that 1 mole of protein=2.3 moles peptide. Therefore, the final calculation is $$\text{TGF-}\beta \text{ protein} = \frac{\text{moles TGF-}\beta \text{ in sample}}{2.3}$$

EXAMPLE 68

Purification of β-Lactoglobulin-Specific TABM (BL-TABM)

One hundred ml of blood was collected by venipuncture from a female with a previously determined high level of antigen-specific TABM to the cow's milk protein β-lactoglobulin. The blood was allowed to clot at room temperature, centrifuged, and the serum collected and stored frozen at −20° C. until required. Fifty-one ml of serum was precipitated with 43% w/v ammonium sulphate. The precipitate was collected after centrifuging at 9700 g for 20 minutes at 4° C. and dissolved in PBS. ½ starting volume. The solution was re-precipitated at 43% w/v ammonium sulphate, centrifuged, dissolved in PBS and dialyzed overnight against PBS at 4° C. The sample was collected and centrifuged to remove any precipitate, and mixed for 2hours at 4° C. by rotation with β-lactoglobulin-sepharose beads. (2 mg β-lactoglobulin per ml of sepharose). The mixture was then poured onto a sintered glass funnel and washed thoroughly with PBS. Molecules specific for β-lactoglobulin (TABM, IgG) were eluted with 0.2 M $NaHCO_3$, pH 9.6 and mixing by inversion for 20 minutes at 4° C. The eluate was collected and immediately neutralized (10% v/v) with 1 M TRIS, pH 7.0. This sample was dialyzed overnight at 4° C. against 100 mM TRIS-150 mM NaCl, pH 7.2. Removal of human immunoglobulin was accomplished by mixing with sepharose beads coupled with anti-human, IgG, IgA and IgM antibodies by inversion for 2 hours at 4° C. The β-lactoglobulin specific TABM was collected as the flow-through from the sintered glass funnel. The sample was concentrated using an Amicon stirred flow cell and YM-10 filter, n-octylglucoside (Sigma) was added to 30 mM. The sample was then sterilized through a 0.2 µfilter and stored at 4° C.

The 9.27 fold concentrate of β-lactoglobulin specific TABM will be referred to as: BL-TABM. A protein concentration of 435 µg/ml was determined using the Biorad assay and BSA as the standard.

EXAMPLE 69

Effect of BL-TABM on TNF-α Production by Peripheral Blood Mononuclear Cells (PBMNC)

Peripheral blood from a normal health (non-atopic) individual was collected by venipuncture and anti-coagulated with preservative-free heparin (Fisons Pty. Ltd., NWS). The blood was layered onto Ficoll (Pharmacia, Sweden) and centrifuged at 200 rpm for 20 minutes. The plasma was removed and the PBMNC isolated and washed 3times PBS. The PBMNC were suspended in RPMI-1640 with 10% v/v heat activated fetal calf serum (FCS), with penicillin and streptomycin (CSL, Melbourne), $2\times10^5$ cells were placed in duplicate in 96-well, round bottom tissue culture plates (NUNC, Denmark), in a final volume of 200 µl following additions of medium, E. coli-LPS (DIFCO), 0–250 µg/ml: BL-TABM, 0–54.38 µg/ml and β-lactoglobulin, 0–5 µg/ml. All additives were made up and diluted in culture medium. Controls included medium and BL-TABM diluent. Plates were incubated for 24 hours at 37° C. in a 5% v/v $CO_2$ incubator. Equal volumes of supernatant were collected from each well, pooled frozen until assayed for TNF-α by ELISA.

EXAMPLE 70

Polyacrylamide Gel Electrophoresis and Immunoblotting

Twelve µg TABM (20 µl) were mixed with 20 µl SDS-PAGE sample buffer ±5% v/v β-2-mercaptoethanol as described (21). The mixtures were boiled 5 minutes and 4µl (870 ng) loaded on a 10/15% w/v PHAST (Pharmacia, Piscataway, NJ) 10–15% w/v polyacrylamide gradient gel and electrophoresed in a PHASE analyzer. Resolved proteins were stained by silver stain or transferred to polyvinylpyrollidone membranes for immunoblotting (21). The membrane was incubated for 1–5 hours at 37° C. with 5% w/v powdered milk in PBS, washed and incubated 16 hours at 4° C. with 10 ml 1:500 dilution (in ELISA wash buffer) of R30 anti-human TABM, or 1:500 rabbit anti-human TGF-β-2 (Santa Cruz Biotechnologies, Santa Cruz, Calif.). The membrane was then washed 4 times and incubated with 10 ml of 1:1000 alkaline phosphatase goat anti-rabbit IgG. After incubation with anti-IgG, the membrane was washed 4 times and 5-bromo-4-chloro-3-indolyl phosphate/Nitro blue tetrazolium (NBT-BCIP) substrate was added.

EXAMPLE 71

Results
Immunoglobulin production to milk proteins

Patients intolerant to milk were challenged with 400–500 ml of cow's milk. The symptoms produced in the patient group by ingestion of milk are summarized in Table 8. These symptoms persisted for at least 8 hours, and in some cases up to 36 hours. For each antigen, specific IgG levels were higher in the patient group (FIG. 30) than the control group. Different patients provided the highest IgG levels for the particular antigen (seen patient numbers, FIG. 30). IgG1 values were significantly higher for β-lactoglobulin and casein (p=0.001) in the patient group. IgG2 levels were significantly higher for casein (p=0.048) in the patient group, but approached significant for β-lactoglobulin. IgG3 levels were not significantly higher in the patient group for each of the antigens. IgG4 levels were significantly raised in the patient group to β-lactoglobulin (p=0.035), and approached significance for α-lactalbumin (p=0.054). Serum samples showing high total IgG levels for particular antigens also showed a high level of one or more IgG subclass to that antigen.

IgE levels specific for casein were significantly higher in the patient group than in controls (p =0.013) Specific IgE levels were low and there was no association between positive skin tests and specific IgE levels in the patient group.

TABM Production to Milk Proteins

Typical titration curves to TABM specific for β-lactoglobulin were obtained for both serum and BL-TABM. A titration for TABM using serum from a milk intolerant patient (FIG. 31) demonstrated TABM binding to β-lactoglobulin. The titer for BL-TABM was considerably higher than for serum. Sera showing elevated TABM for milk proteins did not have high TABM for other antigens such as horse serum and benzoic acid conjugated to human serum albumin.

In the patient group, TABM levels were statistically higher for each antigen (FIG. 32). For each particular antigen, different members of the patient group provided the highest TABM levels. There was not a parallel rise between total IgG and TABM levels for particular sera. Also, four patients who did not show elevated IgG to β-lactoglobulin, α-lactoglobulin or casein, had high or intermediate levels of TABM to β-lactoglobulin or casein.

Isolation of TABM Specific for β-Lactoglobulin

To isolate β- lactoglobulin-specific TABM, 51 ml of serum from a patient with a high titer of β-lactoglobulin-specific TABM were mixed with sepharose beads conjugated with β-lactoglobulin. Approximately 2.4 mg (0.063% total protein) were eluted. As shown in FIG. 33, β-lactoglobulin-specific TABM were detected in the eluate. To characterise the TABM, 500 ng of the protein were reduced and resolved by electrophoresis in an SDS-polyacrylamide gradient gel. As shown in FIG. 34 reduced, β-lactoglobulin-specific TABM were resolved at Mr 28,000 and 46,000 polypeptides. These proteins were not observed in non-reduced proteins, but a faint Mr 110,000 band was observed.

Association of BL-TABM with TGF-β

To assay the functional activity of the affinity-purified BL-TABM, we determined the effects of BL-TABM on TNF-α production by normal PBMNC. The culture of PBMNC with increasing levels of BL-TABM induced increasing levels of TNF-α (FIG. 35). The addition of increasing levels of β-lactoglobulin potentiated this effect (FIG. 35A). The addition of LPS (a strong inducer of TNF-α) resulted in even higher amounts of TNFα produced (FIG. 35B).

Because TGF-β has been shown to induce and/or promote the production of TNF-α, the inventors reasoned that the TNF-potentiating activity of BL-TABM may be due to associated TGF-β. To test this hypothesis, affinity-purified BL-TABM were used in an ELISA Inhibition Assay to detect and quantitate TGF-β. As shown in FIG. 36, approximately 72.8 ng/ml TGF-β1,43.8 ng/ml TGF-β2, and 0 (<5 ng/ml) TGF-β3 were detected by EIA. Immunoblotting of non-reduced BL-TABM with anti-TGF-β2 antibodies (FIG. 37) revealed Mr 28,000 bands that are not detected by immunoblotting with R28. Moreover, R28 does not bind recombinant human TGF-β1 or 2 in ELISA.

In summary, the immune response to three cow's milk antigens, β-lactoglobulin (BLG), α-lactalbumin (AL) and casein (CA) was studied in 15 milk-intolerant adult patients and 11 adult controls. IgG, IgE, IgG subclasses (IgG1, IgG2, IgG3, IgG4) and T-cell derived antigen binding molecules (TABM) specific for each antigen were measured in both groups. In the patient group, a significant elevation of total IgG and TABM against each of the milk antigens was found as well as raised levels of IgG1 to BLG and CA, IgG4 to BLG and IgE to CA. TABM specific for BLG were isolated by affinity by BLG and found to be Mr 28,000–46,000 polypeptides functionally and physically associated with TGF-β1 and TGF-β2. These results indicated a Th2-type immune response to the milk antigens in milk-intolerant individuals as compared with the control group who show a pattern typical of anergy or deletion.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

TABLE 1

PURIFICATION OF TABM FROM COHN FRACTION III PROTEINS

| Fraction | Protein (mg) | MW Range | OD Anti-TABM 500 ng/well | OD Anti-TABM 50 ng/well | Percent of Total Protein |
|---|---|---|---|---|---|
| Unfractionated Cohn fraction III | 2604 | — | 2.0 | n.d. | 100 |
| (NH$_4$)$_2$SO$_4$ | 965 | — | 2.0 | n.d. | 37 |
| Sephacryl I | 80.6 | >600,000 | 2.0 | 2.0 | 3.1 |
| Sephacryl II | 145 | 100,000–300,000 | 1.2 | 0.6 | 15 |
| Sephacryl III | 322 | 40,000–100,000 | 0 | 0 | 12.3 |
| Sephacryl IV | 442 | <30,000 | 0 | 0 | 16.9 |
| Sephacryl I. anti-Ig HSA absorbed | 1.85 | — | 2.0 | 2.0 | 0.19 |

Anti-Ig and anti-HSA absorbed.

TABLE 2

| | Before Toluene Challenge | After Toluene Challenge |
|---|---|---|
| Prose: | | |
| Immediate Recall | 11 items | 6 items |
| Delayed Recall | 10.5 items | 6.5 items |
| Reaction Time: | 212 msec | 219 msec |
| Symbol Digit: | 50 items | 32 items |
| Letter Cancellation: | 71% correct (6'12") | 63% correct (5'40") |
| Stroop:* | | |
| Words | 73 | 75 |
| Colours | 94 | 90 |
| Colour word | 161 | 161 |

*Time in secs to read 100 words of varying levels of difficulty.

TABLE 3

Patient details and sensitivity to toluene following controlled exposure

| NO | AGE | SEX | OCCUPATION | CLINICAL DISABILITY (MILD, MODERATE, SEVERE) | CLINICAL REACTION TO TOLUENE (0-->+++) | CHANGES ON NEUROPSYCHO-LOGICAL TESTING (0-->+++) |
|---|---|---|---|---|---|---|
| 1 | 45 | M | FACTORY WORKER | MODERATE | ++ | +++ |
| 2 | 38 | F | OFFICE WORKER | MODERATE | ++ | ++ |
| 3 | 44 | F | ASSSEMBLER-PROCESS WORKER | MILD | + | ++ |
| 4 | 50 | F | WORKER AT PETROLEUM DEPOT | SEVERE | ++ | ++ |
| 5 | 36 | F | LAWYER | MODERATE | ++ | ++ |
| 6 | 19 | F | STUDENT | MOOERATE | ++ | +++ |

TABLE 3-continued

Patient details and sensitivity to toluene following controlled exposure

| NO | AGE | SEX | OCCUPATION | CLINICAL DISABILITY (MILD, MODERATE, SEVERE) | CLINICAL REACTION TO TOLUENE (0-->+++) | CHANGES ON NEUROPSYCHO-LOGICAL TESTING (0-->+++) |
|---|---|---|---|---|---|---|
| 7 | 18 | M | STUDENT | MODERATE | ++ | ++ |
| 8 | 30 | M | WORKER IN PRINTING SECTION | MODERATE | ++ | + |
| 9 | 49 | F | LABORATORY ASSISTANT | SEVERE | +++ | ++ |
| 10 | 38 | M | WORKED WITH SOLVENTS | SEVERE | ++ | ++ |
| 11 | 44 | F | OFFICE WORKER | MODERATE | ++ | ++ |
| 12 | 46 | F | PROCESS WORKER | SEVERE | +++ | +++ |
| 13 | 52 | M | TEACHER | MODERATE | ++ | + |
| 14 | 41 | M | WORKED WITH SOLVENTS | MODERATE | ++ | ++ |
| 15 | 27 | M | PRINTER | MODERATE | ++ | ++ |
| 16 | 47 | M | TEACHER | MODERATE | ++ | + |
| 17 | 53 | M | TEACHER | SEVERE | ++ | +++ |
| 18 | 38 | M | SPRAY PAINTER | MODERATE | ++ | ++ |
| 19 | 35 | F | HOME DUTIES | MODERATE | ++ | +++ |
| 20 | 43 | F | LABORATORY ASSISTANT | MILD | ++ | ++ |

TABLE 4

Results of neuropsychological testing of toluene sensitive patients.

| Test | No. Cases | Pre Challenge Mean (Range) | Post Challenge Mean (Range) | p Value |
|---|---|---|---|---|
| Prose Memory (immediate) (No. Items recalled) | 18 | 10.61 (7–14.5) | 7.36 (3–12) | 0.0003* |
| Prose Memory (delayed) (No. Items recalled) | 18 | 12.80 (6–19.5) | 8.77 (5–14.5) | 0.0009* |
| Reaction Time (millisecs) | 17 | 207.80 (158–264) | 238.40 (146–414) | 0.0614 |
| Letter Cancellation Time (Mins) | 16 | 4.77 (3.48–6.12) | 4.79 (3.36–6.18) | NS |
| Letter Cancellation (% Correct) | 16 | 82.31 (52–99) | 77.56 (50–98) | 0.0380* |
| Digit Symbol (No. of correct items) | 20 | 45.00 (30–69) | 40.00 (25–57) | 0.0099* |
| Focal Length (cms) | 13 | 28.53 (14–45) | 29.53 (14–48) | NS |
| STROOP (word) (No. seconds/100 words) | 16 | 61.81 (35–190) | 58.93 (32–165) | NS |
| STROOP (colour) (No. seconds/100 words) | 16 | 70.06 (38–150) | 74.43 (29–195) | NS |
| STROOP (colour-word) (No. seconds/100 words) | 15 | 120.06 (32–175) | 119.73 (18–164) | NS |

*Statistically significant ($p < 0.05$); NS, not significantly different, (Mann Whitney UTest).

TABLE 5

Comparison of TABM levels with changes in Focal length and performance on STROOP (colour word) test pre and post toluene challenge.

| Test | p Value | Correlation Coefficient† |
|---|---|---|
| Focal Length (cms) | 0.0208* | 0.6310 |
| STROOP (colour word) | 0.0465* | 0.5209 |

*Significant difference ($p < 0.05$) using the Wilcoxon Sum of Ranks Test. †Spearman correlation Test.

TABLE 6

The median change in scores after exposure to toluene.

| Test | Group 1 14–25 Yrs, n = 7 Median (Range) | Group 2 Up to 13 Yrs, n = 10 Median (Range) | p Value |
|---|---|---|---|
| Prose Memory-delayed, (No. items recalled). | 3 (−3.0–4.5) | 7 (1–11) | 0.017* |
| Digit Symbol Test, (No. of correct items). | 1 (−7–5) | 7 (−7–19) | 0.039* |
| STROOP Colour Word, (No. seconds/100 words). | 17 (3–42) | −2 (−31–9) | 0.017* |

*Significant difference ($p < 0.05$). using the Mann Whitney U-Test.

TABLE 7

The median value of patient responses pre toluene exposure, with respect to type of chemical exposure.

| Test (Pre-exposure) | Group A, n = 6 Median (Range) | Group B, n = 8 Median (Range) | p Value |
|---|---|---|---|
| Prose Memory-Immediate, (No. items recalled). | 9.3 (7.0–11.5) | 12.0 (9.5–14.5) | 0.0215* |
| Reaction Time, (milliseconds). | 197 (183–223) | 230 (190–264) | 0.0441* |

*Significant difference (p < 0.05), using the Mann Whitney U-Test.

TABLE 8

Summary of the symptoms produced after milk challenge in the patient group.

| PATIENT STUDY NO. | AGE | SEX | SYMPTOM RATING* 0–→+++ | | | | | TIME OF SYMPTOM ONSET (MIN) | SKIN TEST (MM) |
| | | | GIT | RT | SKIN | CNS | MS | | |
|---|---|---|---|---|---|---|---|---|---|
| 3  | 31 | F | +  | +  | 0 | + + | 0   | 30  | 0 |
| 4  | 56 | F | 0  | +  | 0 | + + | 0   | 120 | 0 |
| 5  | 32 | F | 0  | +  | 0 | +   | +   | 30  | 3 |
| 9  | 50 | F | 0  | 0  | 0 | + + | +   | 120 | 3 |
| 10 | 36 | M | + +| 0  | 0 | +   | 0   | 30  | 0 |
| 11 | 33 | F | 0  | +  | 0 | + + | + + | 30  | 0 |
| 12 | 41 | F | 0  | + +| 0 | + + | 0   | 240 | 0 |
| 14 | 58 | M | 0  | 0  | 0 | + + | 0   | 15  | 3 |
| 15 | 30 | F | +  | +  | 0 | + + | 0   | 180 | 4 |
| 16 | 24 | F | +  | 0  | 0 | + + | 0   | 180 | 0 |
| 17 | 32 | F | 0  | + +| 0 | + + | 0   | 15  | 3 |
| 18 | 55 | F | 0  | 0  | + | + + | 0   | 180 | 0 |
| 19 | 25 | F | 0  | + +| 0 | + + | +   | 15  | 0 |
| 24 | 51 | F | +  | +  | 0 | + + +| 0  | 15  | 0 |
| 25 | 41 | F | +  | +  | 0 | + + | 0   | 60  | 0 |

*GIT: abdominal pain, diarrhea, distension; RT: nasal stuffiness, post-nasal drip, sore throat; SKIN: itch; CNS: fatigue, headache, sleep distrubance, poor concentration, irritability; MS: muscoskeletal. All patients had symptoms referable to the CNS, and 5 were weakly positive in skin testing.

BIBLIOGRAPHY

1. Kohler G and Milstein C Nature 256: 495–497, 1975.
2. Dibrino M, Ravindran B, and Cone R E, Clin. Immunol. Immunopath. 59: 271–287, 1991.
3. Cone R E, Wang Y, and Malley A. J. Interferon Cytokine Res. 18: 55–67. 1997.
4. Russell R W, Flattau P E, Pope A M, (eds) Behavioural Measures of Neural Toxicity. Report of a symposium. National Academy Press. 1990.
5. Lesak M D, Neuropsychological Assessment (second ed). New York: Oxford University Press, 1993.
6. Golden C J. STROOP colour word test manual Chicago, Stoelting Company, 1978.
7. Smith A, Symbol Digit Modality Test Manual Los Angeles: Western Psychological Service, 1982.
8. DiBrino M, Ravindra B, Clone R Clin. Immunol. Immunopathol. 59: 271–297, 1991.
9. Vojdani A, Ghoneum M, Brautbar N, Toxical. Ind. Health 8: 239–253, 1992.
10. Alun-Jones V, McLaughlan P, Shorthouse M, Workman E, and Hunter J. Lancet 2: 1115–1117, 1982
11. Grant E, Lancet 1: 966–969, 1979.
12. Munro J, Carini C, and Brostoff J, Lancet 1: 719–721, 1984.
13. Eggar J, Wilson J, Carter C. Turner M, and Soothill J. Lancet 2: 865–869, 1983.
14. Martelleti P, Sutherland J, Anastasi E, Di Mario U, and Gracovazzo, M. Headache 29: 664–670, 1989.
15. Straus S, Dale J, Wright R and Metcalfe D. J. Allergy Clin. Immunol. 78: 308–320, 1986.
16. Manu P, Matthews D, and Lane T. Int. J. Eat. Disord. 13: 203–209, 1993.
17. Pearson D, Rix K, and Bently S, Lancet 1: 1259–1261, 1983.
18. Lessof M. Clin. Exp. Allergy 23: 971–972, 1993.
19. Urbanke R, and Kemeny M. IgG and IgG subclasses-response to dietary antigens in patients with immediate and non-immediate food allergy. In. "Food Allergy' Nestle Nutrition Workshop Series" E. Schmidt (ed. pp 71–80, Raven Press Ltd., New York, 1988)
20. Urbanski M, and Cone R E, J. Immunol. 148: 2840–2844, 1992.
21. Urbanksi M, and Cone R E, Cell. Immunol. 153: 131–141, 1994.
22. Wang Y, O'Rourke J, and Cone R E, Intern. Immunol. 9: 211, 1997.

What is claimed is:

1. The hybridoma cell line on deposit with the American Type Culture Collection as Accession No. HB-12589.

2. A monoclonal antibody MG3C9-1A12, which is produced by the hybridoma cell line on deposit with the American Type Culture Collection as Accession No. HB-12589.

3. An antigen-binding fragment of monoclonal antibody MG3C9-1A12, wherein the monoclonal antibody MG3C9-1A12 is produced by the hybridoma cell line on deposit with the American Type Culture Collection as Accession No. HB-12589.

4. A monoclonal antibody labeled with a reporter molecule capable of producing a detectable signal, wherein the monoclonal antibody is the MG3C9-1A12 monoclonal antibody produced by the hybridoma cell line on deposit with the American Type Culture Collection as Acession No. HB-12589.

5. A composition comprising the monoclonal antibody MG3C9-1A12 of claim 2, the antigen-binding fragment of monoclonal antibody MG3C9-1A12 of claim 3, or the monoclonal antibody labeled with a reporter molecule capable of producing a detectable signal of claim 4, and one or more pharmaceutically acceptable carriers or diluents.

* * * * *

UNITED STATES PATENT AND TRADEMARK OFFICE
CERTIFICATE OF CORRECTION

PATENT NO. : 6,485,970 B1
DATED : November 26, 2002
INVENTOR(S) : Cone et al.

It is certified that error appears in the above-identified patent and that said Letters Patent is hereby corrected as shown below:

Column 2,
Line 32, delete "specifally" and replace with -- specifically --.

Column 3,
Line 42, delete "MG33C9" and replace with -- MG3C9 --
Line 65, delete "MG-b 3C9-1A12" and replace with -- MG3CP-1A12 --.
Lines 66 and 67, delete "serem" and replace with -- serum --.

Column 4,
Line 6, delete "MG3C9-1A12+TABM" and replace with -- MG3C9$^+$TABM --.
Line 53, delete "lysdates" and replace with -- lysates --.

Line 62, delete "■ JURKAT" and replace with -- JURKAT--.

Line 63, delete "■ TABM" and replace with -- TABM--.

Column 5,
Line 48, delete "antigent" and replace with -- antigen --.
Line 66, delete "as" and replace with -- was --.

Column 8,
Line 27, delete "BL-TABm" and replace with -- BL-TAB --.
Lines 34 and 36, insert a line between lines 34 and 36 so that it appears as an equation $$\frac{O.D.\ anti\text{-}TGF\text{-}\beta + BL\text{-}TABM x 100}{O.D.\ anti\text{-}TGF\text{-}\beta}$$

Column 9,
Line 64, delete "polyclongal" and replace with -- polyclonal --.

Column 10,
Line 14, delete "for".

Column 12,
Line 55, delete "(i.e. radiosotopes)" and replace with -- (i.e. radioisotopes) --.

UNITED STATES PATENT AND TRADEMARK OFFICE
CERTIFICATE OF CORRECTION

PATENT NO.    : 6,485,970 B1
DATED         : November 26, 2002
INVENTOR(S)   : Cone et al.

It is certified that error appears in the above-identified patent and that said Letters Patent is hereby corrected as shown below:

Column 14,
Line 4, delete "cynate" and replace with -- cyanate --.
Line 29, delete "4nitrophenol" and replace with -- 4-nitrophenol --.
Line 33, delete "N-bromosuccinimde" and replace with -- N-bromosuccinimide --.
Line 46, delete "omithine," and replace with -- ornithine, --.

Column 15,
Line 8, delete "L-N-methylhustidine" and replace with -- L-N-methylhistidine --.
Line 11, delete "L-N-methylysine" and replace with -- L-N-methyllysine --.
Line 37, delete "D-α-methylisoleucine" and replace with -- D-α-methylleucine --.
Line 66, delete "D-N-methyltryosine Dnmtrr" and replace with
-- D-N-methyltyrosine Dnmtyr --.

Column 19,
Line 12, delete "matabolite" and replace with -- metabolite --.

Column 20,
Line 49, delete "a".

Column 22,
Line 50, delete "on" and replace with -- one --.
Line 50, delete "were" and replace with -- was --.

Column 23,
Line 66, after "pre-stained" insert -- standard proteins --.

Column 24,
Line 26, delete "were" and replace with -- was --.
Line 44, delete "noglobulins" and replace with -- noglobulin --.
Line 66, delete "<30,000-<600,000" and replace with -- <30,000 - <600,000 --.

Column 26,
Line 1, delete "MG3C9-1A1 2reacted" and replace with -- MG3C9-1A12 reacted --.
Line 10, delete "MG3C9-1A 12" and replace with -- MG3C9-1A12 --.
Line 65, delete "ad" and replace with -- and --.

UNITED STATES PATENT AND TRADEMARK OFFICE
CERTIFICATE OF CORRECTION

PATENT NO. : 6,485,970 B1
DATED : November 26, 2002
INVENTOR(S) : Cone et al.

It is certified that error appears in the above-identified patent and that said Letters Patent is hereby corrected as shown below:

Column 30,
Line 39, delete "(elevan" and replace with -- (eleven --.

Column 32,
Line 21, delete "washed" and replace with -- washes --.
Line 40, delete "incubated" and replace with -- incubations --.

Column 34,
Line 24, delete "(p=0215)" and replace with -- (p=0.0215) --.

Column 39,
Line 16, delete "baseline. A" and replace with -- baseline and --.
Line 21, delete "re-establisation" and replace with -- re-stabilisation --.

Column 41,
Line 30, delete "EXAMPLES" and replace with -- EXAMPLE 58 --.
Line 34, delete "Patents" and replace with -- Patients --.

Column 43,
Line 4, delete "Md.)d" and replace with -- Md.) --.

Column 44,
Line 1, delete "2was" and replace with -- 2 was --.

Signed and Sealed this

Thirteenth Day of May, 2003

JAMES E. ROGAN
*Director of the United States Patent and Trademark Office*